United States Patent
Ury et al.

(10) Patent No.: US 10,586,612 B2
(45) Date of Patent: Mar. 10, 2020

(54) CLOUD-LIKE MEDICAL-INFORMATION SERVICE

(71) Applicant: ActX, Inc., Seattle, WA (US)

(72) Inventors: Andrew Gray Ury, Seattle, WA (US); Michael Arlt, Seattle, WA (US)

(73) Assignee: ActX, Inc., Seattle, WA (US)

( * ) Notice: Subject to any disclaimer, the term of this patent is extended or adjusted under 35 U.S.C. 154(b) by 1390 days.

(21) Appl. No.: 14/195,559

(22) Filed: Mar. 3, 2014

(65) Prior Publication Data

US 2015/0248525 A1     Sep. 3, 2015

Related U.S. Application Data

(60) Provisional application No. 61/771,639, filed on Mar. 1, 2013.

(51) Int. Cl.
*G16H 10/60* (2018.01)
*G06F 16/245* (2019.01)
(Continued)

(52) U.S. Cl.
CPC ........... *G16H 10/60* (2018.01); *G06F 16/245* (2019.01); *G06F 19/324* (2013.01); *G06Q 50/24* (2013.01); *G16B 50/00* (2019.02); *H04L 63/08* (2013.01)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS 5,664,109 A * 9/1997 Johnson ................ G06F 19/322
                                                              705/2
9,842,188 B2 * 12/2017 Stern ....................... G06Q 10/10
(Continued)

FOREIGN PATENT DOCUMENTS

| KR | 10-2003-0030690 A | 4/2003 |
| KR | 10-2011-0054926 A | 5/2011 |
| KR | 2012-158621 A1 | 11/2012 |

OTHER PUBLICATIONS

Supplementary European Search Report, dated Jul. 15, 2016.

*Primary Examiner* — Sheetal R Paulson
(74) *Attorney, Agent, or Firm* — Olympic Patent Works PLLC

(57) ABSTRACT

The current document is directed to methods and systems for organizing, storing, searching, aggregating, and distributing large quantities of biological information obtained for individual patients. In one described implementation, the knowledge and information is stored, in data-storage facilities within cloud-computing-like systems, as clinical actions, biological elements, and variants that are logically linked together to form network-like data structures. Individual patient data and clinical-knowledge databases, including the network-like clinical-knowledge data structures, are hosted in cloud-computing-like data centers along with a variety of services that receive and process queries from users, medical-service providers, and electronic-health-record-based applications and that return requested information to the requesting entities. Despite the enormous amounts of patient data and clinical knowledge that may be stored in the cloud-computing-like data centers, certain implementations of the currently disclosed systems return responses to medical-information queries in under a second, with other implementations providing even faster query-processing turn-around times.

21 Claims, 55 Drawing Sheets

(51) Int. Cl.
*G06Q 50/24* (2012.01)
*G16B 50/00* (2019.01)
*G06F 19/00* (2018.01)
*H04L 29/06* (2006.01)

(58) Field of Classification Search
CPC ........ G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00
See application file for complete search history.

(56) References Cited

U.S. PATENT DOCUMENTS

| | | |
|---|---|---|
| 2003/0039362 A1* | 2/2003 | Califano ............. G06F 21/6254 380/283 |
| 2011/0047169 A1 | 2/2011 | Leighton |
| 2011/0119088 A1* | 5/2011 | Gunn ..................... G06Q 50/24 705/3 |
| 2011/0126197 A1* | 5/2011 | Larsen .................. H04L 9/3213 718/1 |
| 2011/0189165 A1 | 8/2011 | Roses |
| 2011/0289134 A1 | 11/2011 | De Los Reyes |
| 2012/0059668 A1 | 3/2012 | Baldock |
| 2012/0089420 A1 | 4/2012 | Hoffman |
| 2012/0173585 A1 | 7/2012 | Pan et al. |
| 2014/0244300 A1* | 8/2014 | Bess ..................... G06F 19/322 705/3 |
| 2015/0163206 A1* | 6/2015 | McCarthy ........... G06F 21/6227 713/171 |

* cited by examiner

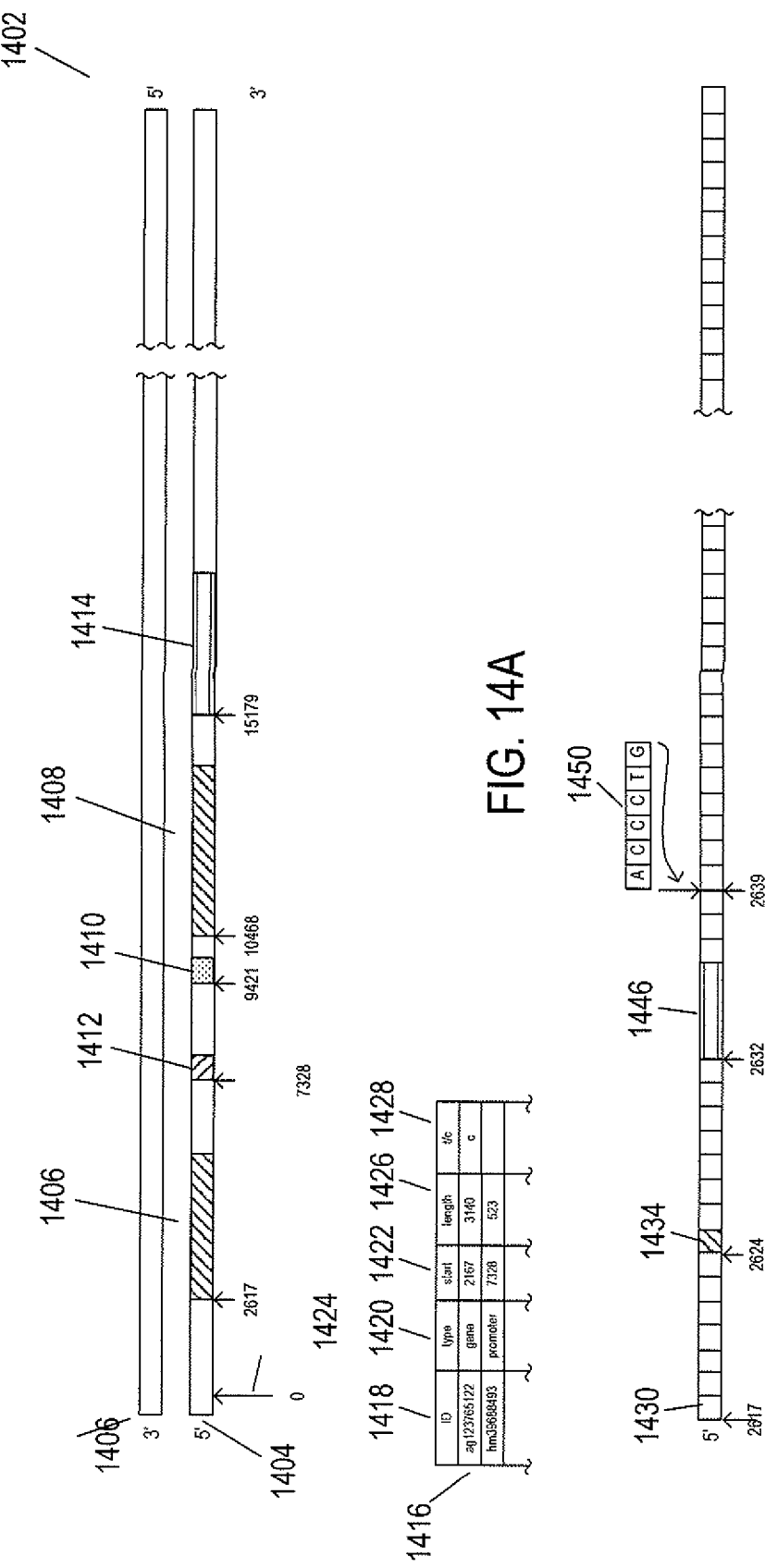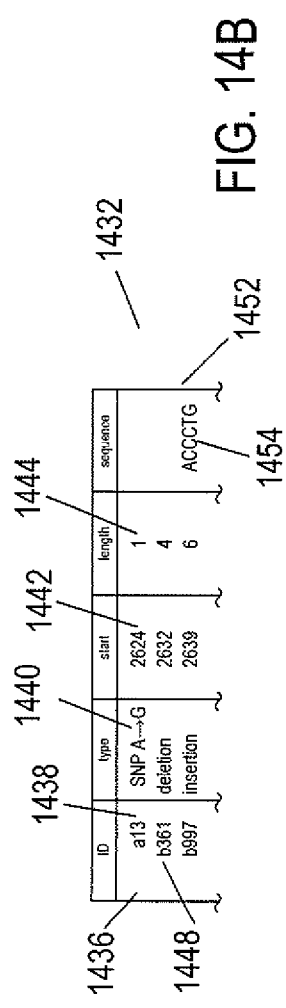
FIG. 14A
FIG. 14B public/private key encryption select two distinct prime numbers $p$ and $q$
$n = pq$
$\varphi(n) = (p-1)(q-1)$
select $e$: $1 < e < \varphi(n)$ and $gcd(e, \varphi(n)) = 1$
compute $d$: $(d*e) \bmod \varphi(n) = 1$
$k_e = (e,n)$    (public key)
$K_d = (d,n,p,q)$, $(d,p,q)$, or $(d,n)$    (private key)

to encrypt $M$
    $M \rightarrow m$: $0 < m < n$
    $C \leftarrow (OAEP(m))^e \pmod{n}$
to decrypt $C$
    $m = OAEP^{-1}(C^d \pmod{n})$
    $M \leftarrow m$ digital signature to sign:
    $m$Hash = hash($M$)
    $EM$ = transform ($m$Hash)
    signature = $EM^d \bmod n$ = DEC($EM, k_d$)
to verify:
    $m$Hash = hash($M$)
    $EM'$ = signature$^e$ (mod $n$) = ENC(signature, $k_e$)
    $m$Hash' = transform$^{-1}$($EM'$)
    when $m$Hash = $m$Hash', signature is verified symmetric-key encryption
Symmetric key $k$
$C \leftarrow ENC(M, k)$
$M \rightarrow DEC(C, k)$

HMAC $HMAC(K,m) = H((K \oplus opad) \| H((K \oplus ipad) \| m))$
where:
    $H$ is a cryptographic hash function;
    $K$ is a secret key;
    $m$ is message;
    $\|$ is the concatenation operation;
    $\oplus$ is XOR; and
    $opad$ and $ipad$ are block-long constants.

FIG. 31

CLOUD-LIKE MEDICAL-INFORMATION SERVICE

CROSS-REFERENCE TO RELATED APPLICATION

This application claims the benefit of Provisional Application No. 61/771,639, filed Mar. 1, 2013.

TECHNICAL FIELD

The current document is directed to electronic information storage and distribution and, in particular, to methods and systems for efficiently providing clinical information, including patient-specific genomics information, from a cloud-like information-storage facility to patients, clinicians, medical-service providers, researchers, and electronic-health-records-based applications.

BACKGROUND

During the past 75 years, enormous progress has been made in many fundamental fields of science and technology. In particular, computer science and related sciences and technologies have advanced from simple programs runs on primitive, mechanical computing apparati and early vacuum-tube-based electronic computer systems to modern, complex, highly distributed systems of electronic computers that support many different types of applications and services. The development of extremely fast, multi-processor, distributed computer systems, high-capacity mass-storage devices and systems, virtualization technologies, and the Internet now enable developers, from a single control panel displayed on a remote personal computer, to configure and launch cloud-computing-based data centers containing thousands of virtual servers supporting the execution of many thousands of applications. The development of secure-computing-networking protocols and reliable transaction-processing technologies allow these cloud-computing-based data centers to concurrently carry out enormous numbers of secure transactions with remote users distributed across the world. Even relatively modest personal computers feature mass-storage devices capable of storing terabytes of data. In addition, the emergence of smart phones and tablet devices allows users to connect to cloud-computing facilities through mobile phones and table devices, greatly expanding the reach and accessibility of computing technologies to users.

Basic fields of scientific inquiry, including physics, chemistry, and biology, rapidly developed during the 1700's and 1800's before entering an era of exponential progress in the late 1800's until the present time. The structure of deoxyribonucleic acid ("DNA") was initially proposed only in the mid 1950's, but quickly led to the elucidation of the genetic code in the 1960's and the development of modern molecular biology and biotechnology in the latter portion of the $20^{th}$ century. Modern technologies have now made it possible to produce an entire genetic sequence for an individual patient in days or even hours for a cost that will soon be less than a thousand dollars. These technologies are expected to result in broad-based utilization of personal genomics in clinical medicine. Similar advancements are expected to allow the proteins, lipids, polysaccharides, ribonucleic-acid molecules ("RNA"), and other biomolecules to be characterized for individual patients and used for medical diagnosis and treatment. Currently, large research efforts are devoted to characterizing and understanding the microbiome, the complement of microorganisms hosted by human beings that carry out many necessary functions for their human hosts and that greatly affect the health of human beings.

It has long been recognized that progress in the use of genomics, proteomics, transcriptomics, and other broad fields of biopolymer characterization for clinical diagnosis and treatment will necessarily depend on development of computational methods and systems for organizing, storing, searching, aggregating, and distributing the vast quantities of biological information that are becoming accessible for individual patients by modern technologies. While computer-based technologies are already widely used in life-sciences-research and clinical applications, new developments and methods are sought for harnessing the knowledge and information becoming available for individual patients for use by researchers, clinicians, and medical-service providers.

SUMMARY

The current document is directed to methods and systems for organizing, storing, searching, aggregating, and distributing large quantities of biological information obtained for individual patients. In one described implementation, the knowledge and information is stored, in data-storage facilities within cloud-computing-like systems, as clinical actions, biological elements, and variants that are logically linked together to form network-like data structures. Individual patient data and clinical-knowledge databases, including the network-like clinical-knowledge data structures, are hosted in cloud-computing-like data centers along with a variety of services that receive and process queries from users, medical-service providers, and electronic-health-record-based applications and that return requested information to the requesting entities. Despite the enormous amounts of patient data and clinical knowledge that may be stored in the cloud-computing-like data centers, certain implementations of the currently disclosed systems return responses to medical-information queries in under a second, with other implementations providing even faster query-processing turnaround times.

BRIEF DESCRIPTION OF THE DRAWINGS

FIGS. 14A-B illustrate information encoding within a double-stranded DNA polymer and types of variant sequences encountered in natural DNA.

FIG. 31 summarizes various different encryption-based techniques referred to in the following discussions.

DETAILED DESCRIPTION

The current document is directed to methods and systems that store and organize large amounts of patient data and clinical knowledge and that, through a query/response interface, use the stored and organized patient data and clinical knowledge to provide reliable, data-based- and science-based responses to numerous types of information queries. In the following discussion, a method and system that stores and organizes genomics information for patients and that processes and responds to genomics-based queries is described, as one example of the more general methods and systems to which the current document is directed. The following discussion is divided into a number of subsection: (1) a description of computer hardware and software platforms that underlie the currently disclosed systems; (2) a brief description of DNA and genomics data; (3) a detailed description of the network-like data structure used for storing clinical knowledge, including clinical genomics knowledge; (4) a description of secure-computing aspects of the currently disclosed system; and (5) an example of the types of queries that can be processed by the currently disclosed system.

Hardware and Networking Platforms

Figure 1:
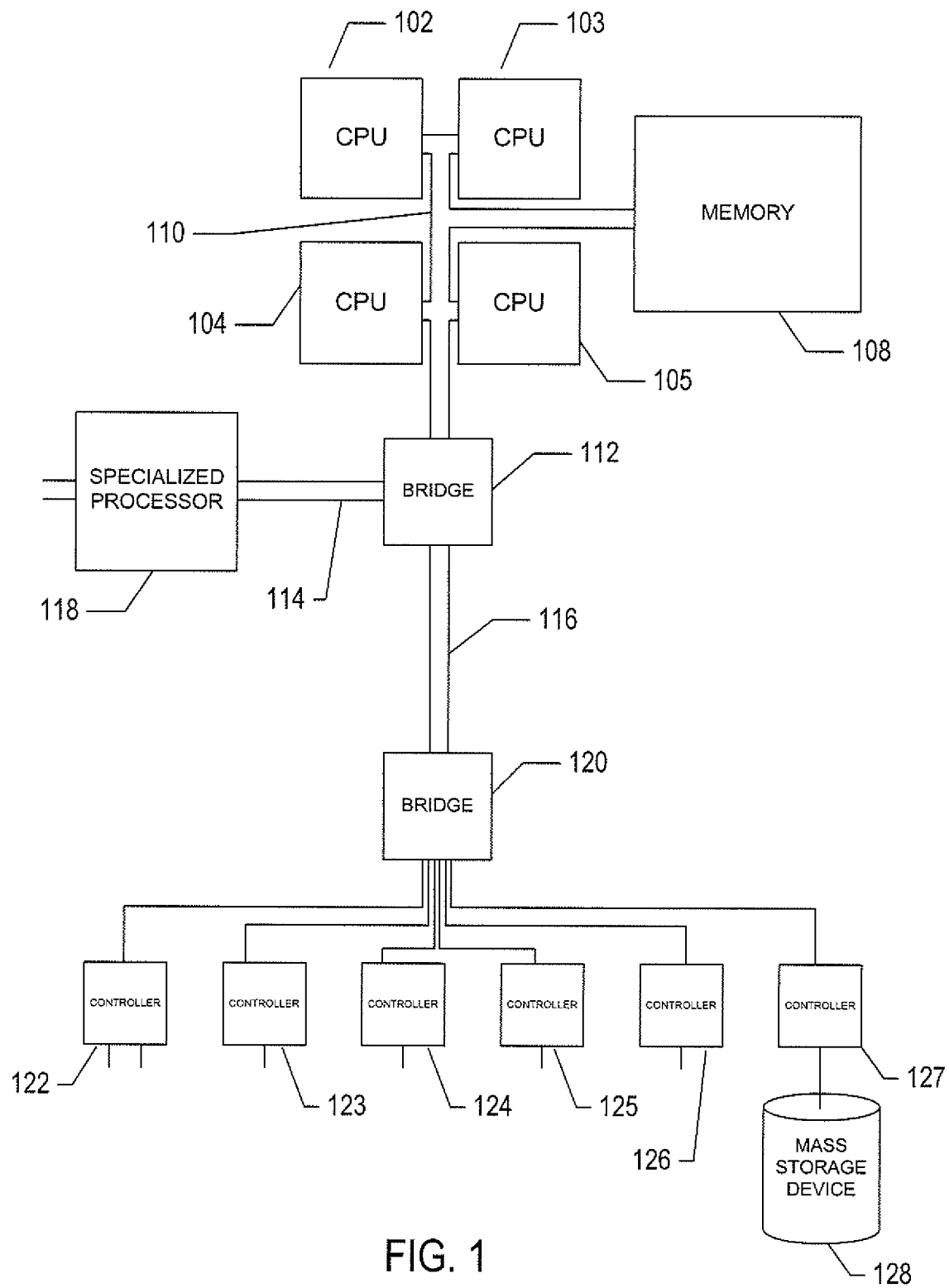
FIG. 1 provides a general architectural diagram for various types of computers and other processor-controlled devices.

FIG. 1 provides a general architectural diagram for various types of computers and other processor-controlled devices. The high-level architectural diagram may describe a modern computer system, such as a personal computer or server. The computer system contains one or multiple central processing units ("CPUs") 102-105, one or more electronic memories 108 interconnected with the CPUs by a CPU/memory-subsystem bus 110 or multiple busses, a first bridge 112 that interconnects the CPU/memory-subsystem bus 110 with additional busses 114 and 116, or other types of high-speed interconnection media, including multiple, high-speed serial interconnects. These busses or serial interconnections, in turn, connect the CPUs and memory with specialized processors, such as a graphics processor 118, and with one or more additional bridges 120, which are interconnected with high-speed serial links or with multiple controllers 122-127, such as controller 127, that provide access to various different types of mass-storage devices 128, electronic displays, input devices, and other such components, subcomponents, and computational resources.

Figure 2:
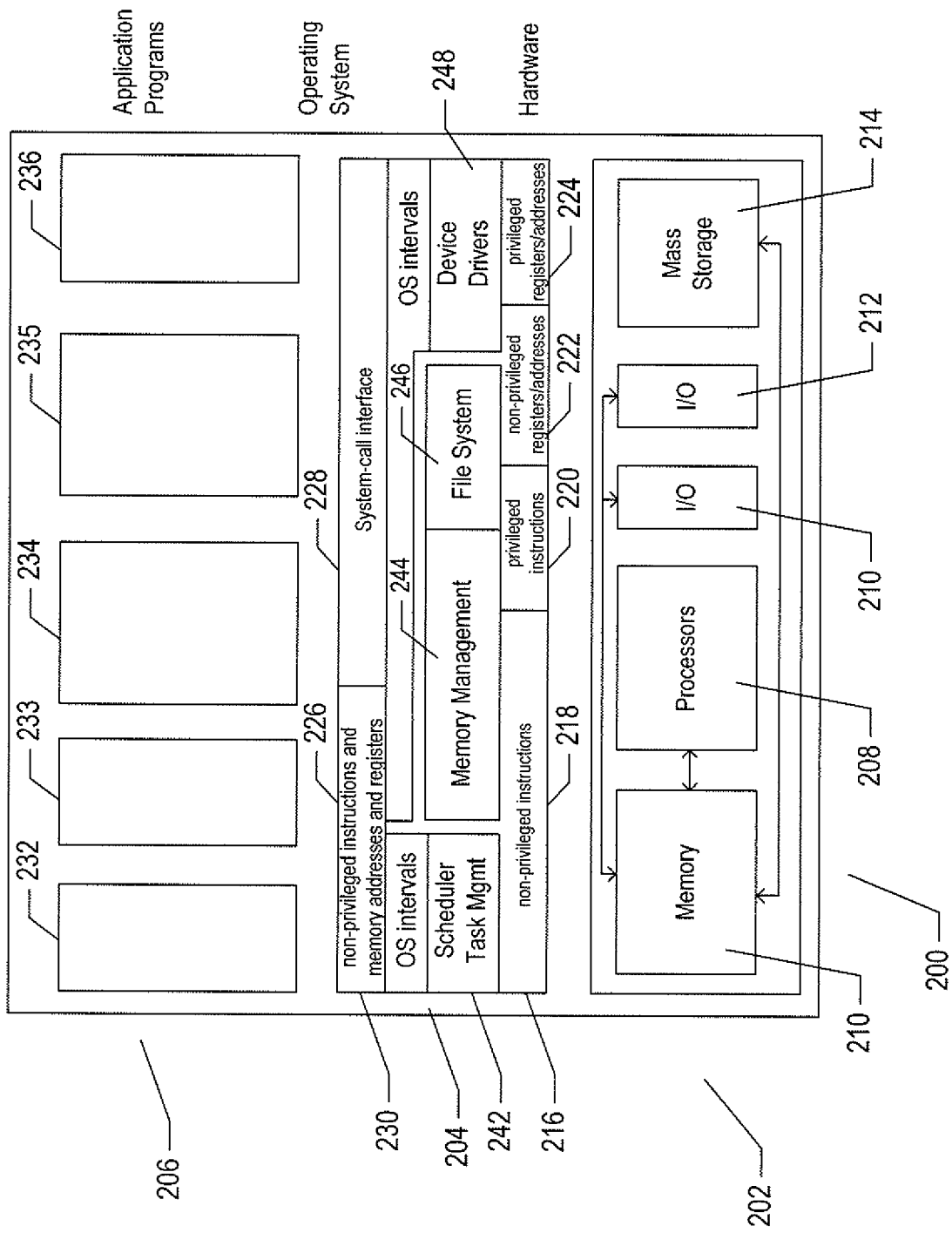
FIG. 2 illustrates generalized hardware and software components of a general-purpose computer system.

FIG. 2 illustrates generalized hardware and software components of a general-purpose computer system. The computer system 200 is often considered to include three fundamental layers: (1) a hardware layer or level 202; (2) an operating-system layer or level 204; and (3) an application-program layer or level 206. The hardware layer 202 includes one or more processors 208, system memory 210, various different types of input-output ("I/O") devices 210 and 212, and mass-storage devices 214. Of course, the hardware level also includes many other components, including power supplies, internal communications links and busses, specialized integrated circuits, many different types of processor-controlled or microprocessor-controlled peripheral devices and controllers, and many other components. The operating system 204 interfaces to the hardware level 202 through a low-level operating system and hardware interface 216 generally comprising a set of non-privileged computer instructions 218, a set of privileged computer instructions 220, a set of non-privileged registers and memory addresses 222, and a set of privileged registers and memory addresses 224. In general, the operating system exposes non-privileged instructions, non-privileged registers, and non-privileged memory addresses 226 and a system-call interface 228 as an operating-system interface 230 to application programs 232-236 that execute within an execution environment provided to the application programs by the operating system. The operating system, alone, accesses the privileged instructions, privileged registers, and privileged memory addresses. By reserving access to privileged instructions, privileged registers, and privileged memory addresses, the operating system can ensure that application programs and other higher-level computational entities cannot interfere with one another's execution and cannot change the overall state of the computer system in ways that could deleteriously impact system operation. The operating system includes many internal components and modules, including a scheduler 242, memory management 244, a file system 246, device drivers 248, and many other components and modules.

Figure 3:
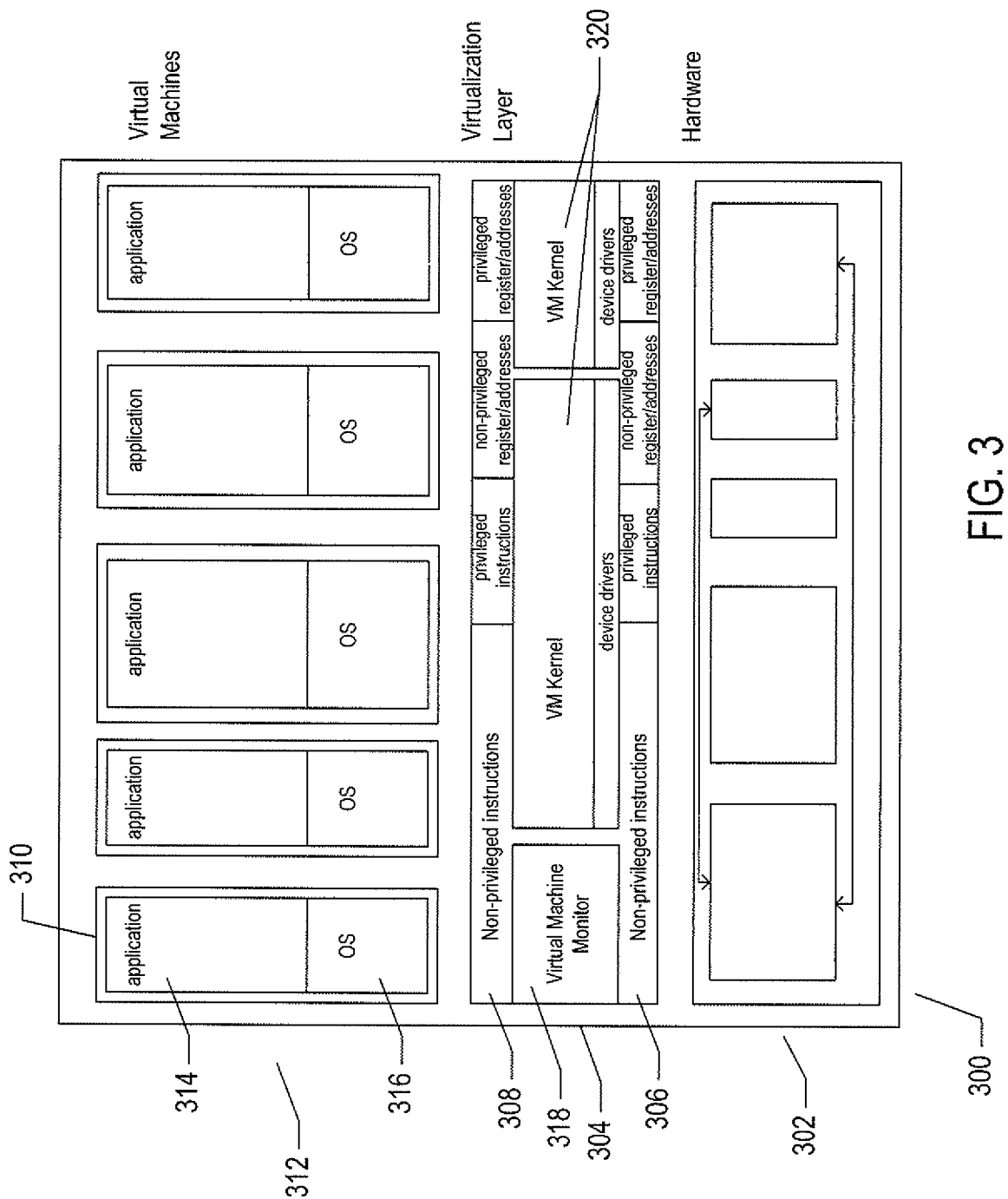
FIG. 3 illustrates generalized hardware and software components of a general-purpose computer system that includes a virtualization layer.

FIG. 3 illustrates generalized hardware and software components of a general-purpose computer system that includes a virtualization layer. FIG. 3 uses the same illustration conventions as used in FIG. 2. In particular, the computer system 300 in FIG. 3 includes the same hardware layer 302 as the hardware layer 402 shown in FIG. 2. However, rather than providing an operating system layer directly above the hardware layer, as in FIG. 2, the virtualized computing environment illustrated in FIG. 3 features a virtualization layer 304 that interfaces through a virtualization-layer/hardware-layer interface 306, equivalent to interface 216 in FIG. 2, to the hardware. The virtualization layer provides a hardware-like interface 308 to a number of virtual machines, such as virtual machine 310, executing above the virtualization layer in a virtual-machine layer 312. Each virtual machine includes one or more application programs or other higher-level computational entities packaged together with an operating system, such as application 314 and operating system 316 packaged together within virtual machine 310. Each virtual machine is thus equivalent to the operating-system layer 204 and application-program layer 206 in the general-purpose computer system shown in FIG. 2. Each operating system within a virtual machine interfaces to the virtualization-layer interface 308 rather than to the actual hardware interface 306. The virtualization layer partitions hardware resources into abstract virtual-hardware layers to which each operating system within a virtual machine interfaces. The operating systems within the virtual machines, in general, are unaware of the virtualization layer and operate as if they were directly accessing a true hardware interface. The virtualization layer ensures that each of the virtual machines currently executing within the virtual environment receive a fair allocation of underlying hardware resources and that all virtual machines receive sufficient resources to progress in execution. The virtualization-layer interface 308 may differ for different operating systems. For example, the virtualization layer is generally able to provide virtual hardware interfaces for a variety of different types of computer hardware. This allows, as one example, a virtual machine that includes an operating system designed for a particular computer architecture to run on hardware of a different architecture. The number of virtual machines need not be equal to the number of physical processors or even a multiple of the number of processors. The virtualization layer includes a virtual-machine-monitor module 318 that virtualizes physical processors in the hardware layer to create virtual processors on which each of the virtual machines executes. For execution efficiency, the virtualization layer attempts to allow virtual machines to directly execute non-privileged instructions and to directly access non-privileged registers and memory. However, when the operating system within a virtual machine accesses virtual privileged instructions, virtual privileged registers, and virtual privileged memory through the virtualization-layer interface 308, the accesses may result in execution of virtualization-layer code to simulate or emulate the privileged resources. The virtualization layer additionally includes a kernel module 320 that manages memory, communications, and data-storage machine resources on behalf of executing virtual machines. The kernel, for example, may maintain shadow page tables on each virtual machine so that hardware-level virtual-memory facilities can be used to process memory accesses. The kernel may additionally include routines that implement virtual communications and data-storage devices as well as device drivers that directly control the operation of underlying hardware communications and data-storage devices. Similarly, the kernel virtualizes various other types of I/O devices, including keyboards, optical-disk drives, and other such devices. The virtualization layer essentially schedules execution of virtual machines much like an operating system schedules execution of application programs, so that the virtual machines each execute within a complete and fully functional virtual hardware layer.

Figure 4:
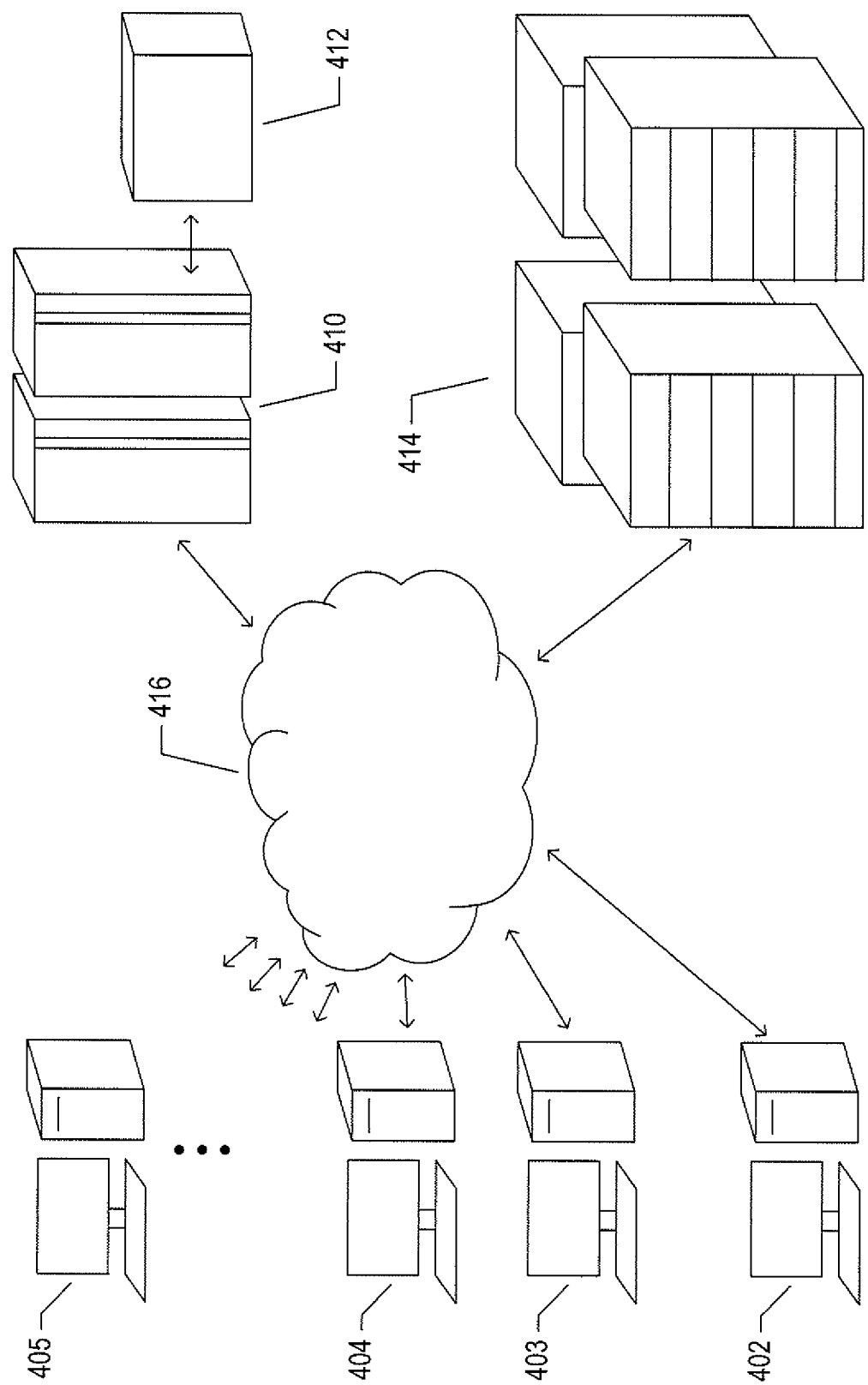
FIG. 4 illustrates an Internet-connected distributed computer system.

FIG. 4 illustrates an Internet-connected distributed computer system. FIG. 4 shows a typical distributed system in which a large number of PCs 402-405, a high-end distributed mainframe system 410 with a large data-storage system 412, and a large computer center 414 with large numbers of rack-mounted servers or blade servers all interconnected through various communications and networking systems that together comprise the Internet 416. Such distributed computing systems provide diverse arrays of functionalities. For example, a PC user sitting in a home office may access hundreds of millions of different web sites provided by hundreds of thousands of different web servers throughout the world and may access high-computational-bandwidth computing services from remote computer facilities for running complex computational tasks.

Figure 5:
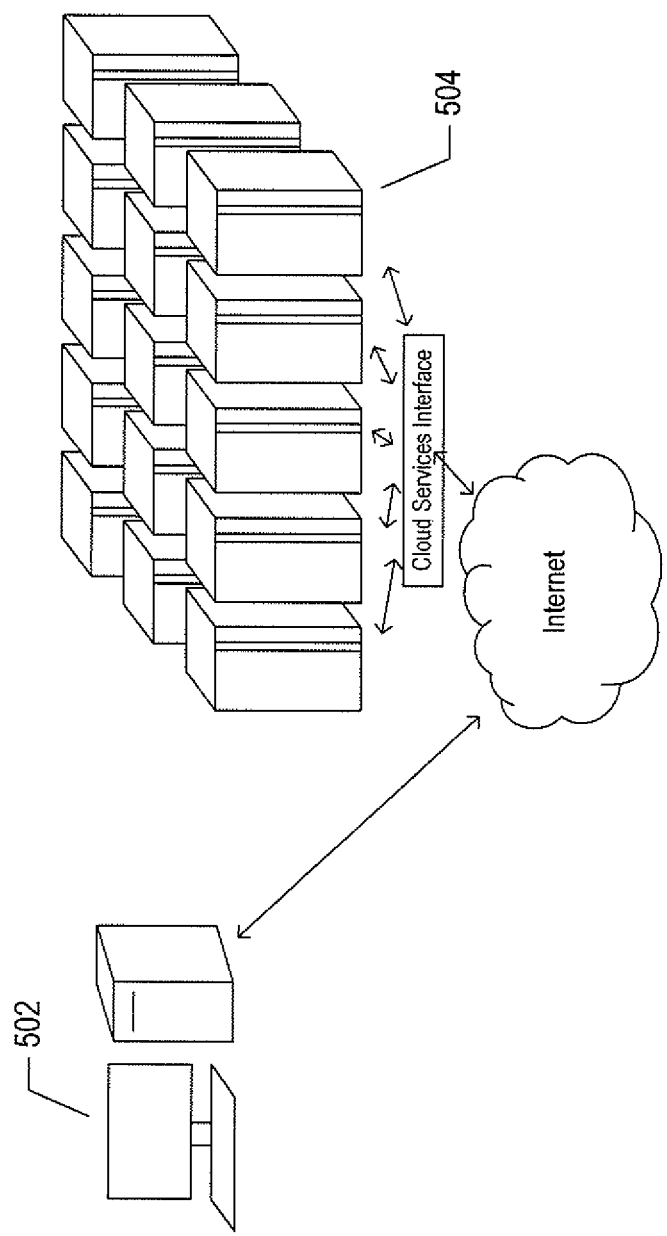
FIG. 5 illustrates cloud computing.

FIG. 5 illustrates cloud computing. In the recently developed cloud-computing paradigm, computing cycles and data-storage facilities are provided to organizations and individuals by cloud-computing providers. In FIG. 5, a user using a personal computer 502 accesses a service provided by an organization that has implemented server-side applications to execute in a public cloud 504. The organization can configure virtual computer systems and even entire virtual data centers and can launch execution of server-side application programs on the virtual computer systems and virtual data centers in order to carry out any of many different types of computational tasks Cloud-computing facilities are intended to provide computational bandwidth and data-storage services much as utility companies provide electrical power and water to consumers. Cloud computing provides enormous advantages to organizations which do not wish to purchase, manage, and maintain in-house data centers. Such organizations can dynamically add and delete virtual computer systems from their virtual data centers within public clouds in order to track computational-bandwidth and data-storage needs, rather than purchasing sufficient computer systems within a physical data center to handle peak computational-bandwidth and data-storage demands. Moreover, organizations can completely avoid the overhead of maintaining and managing physical computer systems, including hiring and periodically retraining information-technology specialists and continuously paying for operating-system and database-management-system upgrades. Furthermore, cloud-computing interfaces allow for easy and straightforward configuration of virtual computing facilities, flexibility in the types of applications and operating systems that can be configured, and other functionalities that are useful even for owners and administrators of private cloud-computing facilities used by a single organization. In the current document, the adjective "cloud-like" is used to mean that the noun or phrase modified by the adjective "cloud-like" is based on, or implemented within, either a commercial cloud-computing facility or a private data center that includes multiple servers and one or more data-storage facilities and that can be accessed by remote user devices in order for users to submit requests to the commercial cloud-computing facility or a private data center and receive responses from the commercial cloud-computing facility or a private data center. Furthermore, a cloud-like system may be a geographically distributed system comprising multiple commercial cloud-computing facilities, multiple private data centers, or a combination of commercial cloud-computing facilities and private data centers.

Figure 6:
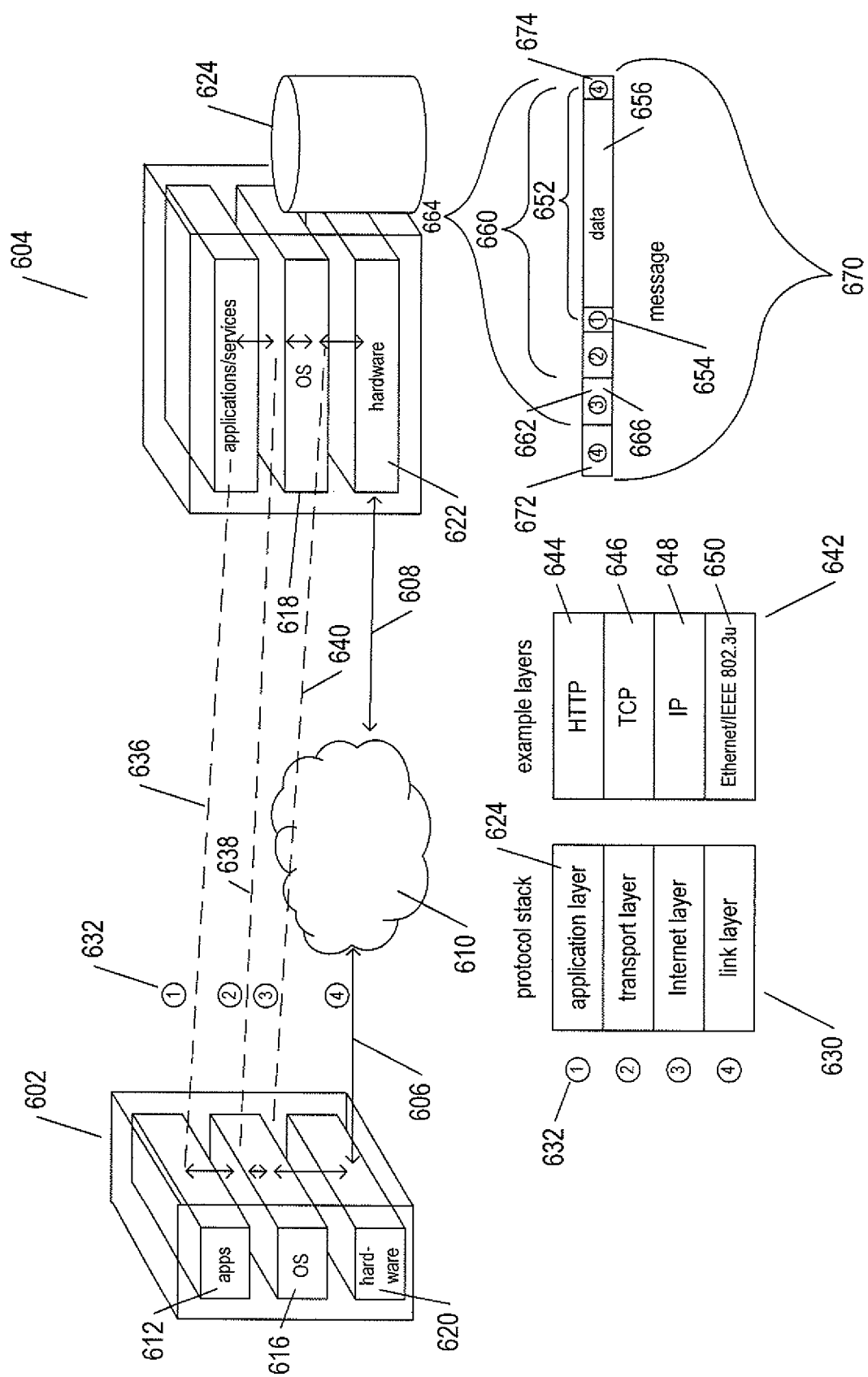
FIG. 6 illustrates electronic communications between a client and server computer.

FIG. 6 illustrates electronic communications between a client and server computer. In FIG. 6, a client computer 602 is shown to be interconnected with a server computer 604 via local communication links 606 and 608 and a complex distributed intermediary communications system 610, such as the Internet. This complex communications system may include a large number of individual computer systems and many types of electronic communications media, including wide-area networks, public switched telephone networks, wireless communications, satellite communications, and many other types of electronics-communications systems and intermediate computer systems, routers, bridges, and other device and system components. Both the server and client computers are shown to include three basic internal layers including an applications layer 612 in the client computer and a corresponding applications and services layer 614 in the server computer, an operating-system layer 616 and 618, and a hardware layer 620 and 622. The server computer 604 is additionally associated with an internal, peripheral, or remote data-storage subsystem 624. The hardware layers 620 and 622 may include the components discussed above with reference to FIG. 1 as well as many additional hardware components and subsystems, such as power supplies, cooling fans, switches, auxiliary processors, and many other mechanical, electrical, electromechanical, and electro-optical-mechanical components. The operating system 616 and 618 represents the general control system of both a client computer 602 and a server computer 604. The operating system interfaces to the hardware layer through a set of registers that, under processor control, are used for transferring data, including commands and stored information, between the operating system and various hardware components. The operating system also provides a complex execution environment in which various application programs, including database management systems, web browsers, web services, and other application programs execute. In many cases, modern computer systems employ an additional layer between the operating system and the hardware layer, referred to as a "virtualization layer," that interacts directly with the hardware and provides a virtual-hardware-execution environment for one or more operating systems.

Client systems may include any of many types of processor-controlled devices, including tablet computers, laptop computers, mobile smart phones, and other such processor-controlled devices. These various types of clients may include only a subset of the components included in a desktop personal component as well components not generally included in desktop personal computers.

Electronic communications between computer systems generally comprises packets of information, referred to as datagrams, transferred from client computers to server computers and from server computers to client computers. In many cases, the communications between computer systems is commonly viewed from the relatively high level of an application program which uses an application-layer protocol for information transfer. However, the application-layer protocol is implemented on top of additional layers, including a transport layer, Internet layer, and link layer. These layers are commonly implemented at different levels within computer systems. Each layer is associated with a protocol for data transfer between corresponding layers of computer systems. These layers of protocols are commonly referred to as a "protocol stack." In FIG. 6, a representation of a common protocol stack 630 is shown below the interconnected server and client computers 604 and 602. The layers are associated with layer numbers, such as layer number "1" 632 associated with the application layer 634. These same layer numbers are used in the depiction of the interconnection of the client computer 602 with the server computer 604, such as layer number "1" 632 associated with a horizontal dashed line 636 that represents interconnection of the application layer 612 of the client computer with the applications/services layer 614 of the server computer through an application-layer protocol. A dashed line 636 represents interconnection via the application-layer protocol in FIG. 6, because this interconnection is logical, rather than physical. Dashed-line 638 represents the logical interconnection of the operating-system layers of the client and server computers via a transport layer. Dashed line 640 represents the logical interconnection of the operating systems of the two computer systems via an Internet-layer protocol. Finally, links 606 and 608 and cloud 610 together represent the physical communications media and components that physically transfer data from the client computer to the server computer and from the server computer to the client computer. These physical communications components and media transfer data according to a link-layer protocol. In FIG. 6, a second table 642 aligned with the table 630 that illustrates the protocol stack includes example protocols that may be used for each of the different protocol layers. The hypertext transfer protocol ("HTTP") may be used as the application-layer protocol 644, the transmission control protocol ("TCP") 646 may be used as the transport-layer protocol, the Internet protocol 648 ("IP") may be used as the Internet-layer protocol, and, in the case of a computer system interconnected through a local Ethernet to the Internet, the Ethernet/IEEE 802.3u protocol 650 may be used for transmitting and receiving information from the computer system to the complex communications components of the Internet. Within cloud 610, which represents the Internet, many additional types of protocols may be used for transferring the data between the client computer and server computer.

Consider the sending of a message, via the HTTP protocol, from the client computer to the server computer. An application program generally makes a system call to the operating system and includes, in the system call, an indication of the recipient to whom the data is to be sent as well as a reference to a buffer that contains the data. The data and other information are packaged together into one or more HTTP datagrams, such as datagram 652. The datagram may generally include a header 654 as well as the data 656, encoded as a sequence of bytes within a block of memory. The header 654 is generally a record composed of multiple byte-encoded fields. The call by the application program to an application-layer system call is represented in FIG. 6 by solid vertical arrow 658. The operating system employs a transport-layer protocol, such as TCP, to transfer one or more application-layer datagrams that together represent an application-layer message. In general, when the application-layer message exceeds some threshold number of bytes, the message is sent as two or more transport-layer messages. Each of the transport-layer messages 660 includes a transport-layer-message header 662 and an application-layer datagram 652. The transport-layer header includes, among other things, sequence numbers that allow a series of application-layer datagrams to be reassembled into a single application-layer message. The transport-layer protocol is responsible for end-to-end message transfer independent of the underlying network and other communications subsystems, and is additionally concerned with error control, segmentation, as discussed above, flow control, congestion control, application addressing, and other aspects of reliable end-to-end message transfer. The transport-layer datagrams are then forwarded to the Internet layer via system calls within the operating system and are embedded within Internet-layer datagrams 664, each including an Internet-layer header 666 and a transport-layer datagram. The Internet layer of the protocol stack is concerned with sending datagrams across the potentially many different communications media and subsystems that together comprise the Internet. This involves routing of messages through the complex communications systems to the intended destination. The Internet layer is concerned with assigning unique addresses, known as "IP addresses," to both the sending computer and the destination computer for a message and routing the message through the Internet to the destination computer. Internet-layer datagrams are finally transferred, by the operating system, to communications hardware, such as a network-interface controller ("NIC") which embeds the Internet-layer datagram 664 into a link-layer datagram 670 that includes a link-layer header 672 and generally includes a number of additional bytes 674 appended to the end of the Internet-layer datagram. The link-layer header includes collision-control and error-control information as well as local-network addresses. The link-layer packet or datagram 670 is a sequence of bytes that includes information introduced by each of the layers of the protocol stack as well as the actual data that is transferred from the source computer to the destination computer according to the application-layer protocol.

Figure 7:
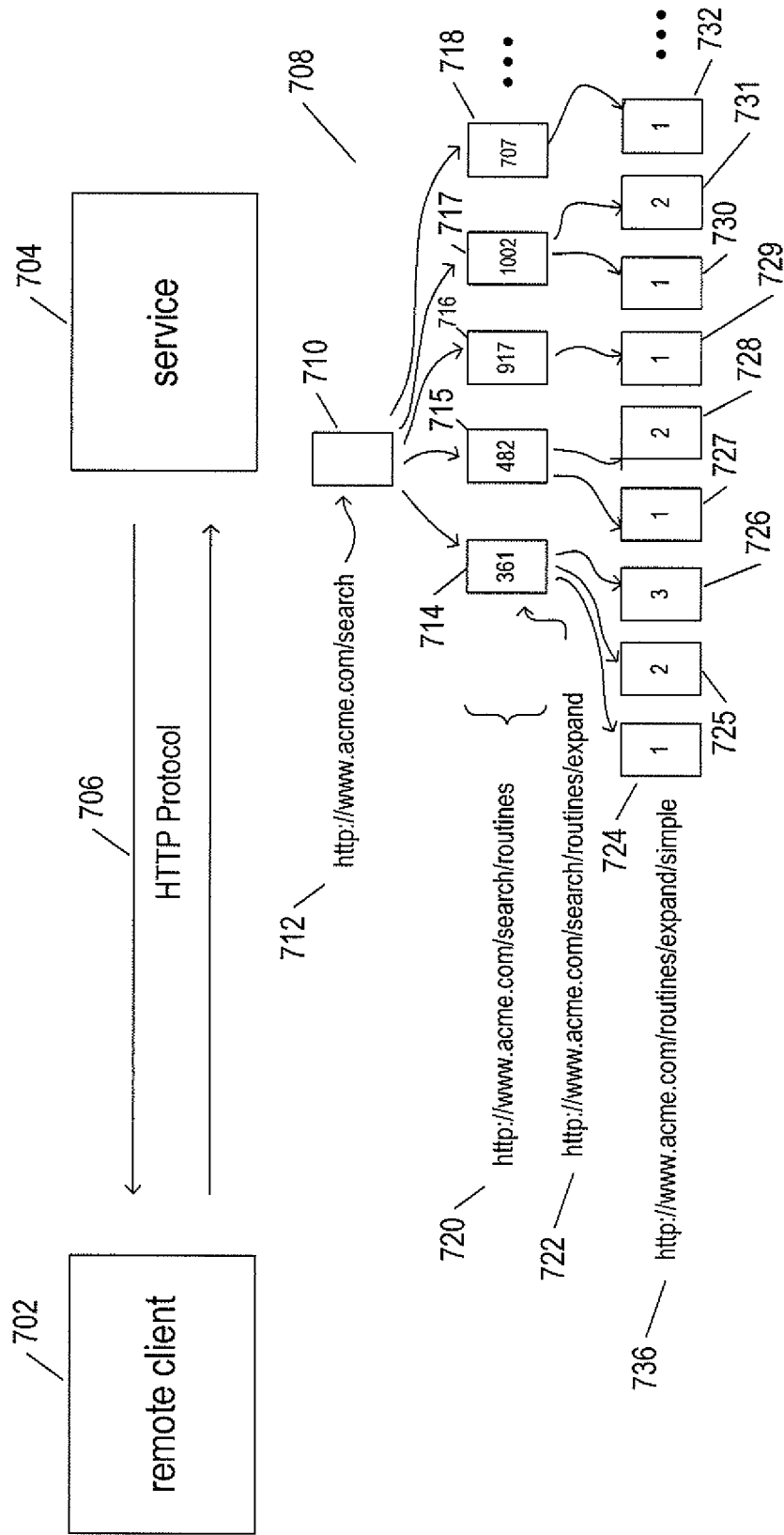
FIG. 7 illustrates the role of resources in RESTful APIs.

Next, the RESTful approach to web-service APIs is described, beginning with FIG. 7. FIG. 7 illustrates the role of resources in RESTful APIs. In FIG. 7, and in subsequent figures, a remote client 702 is shown to be interconnected and communicating with a service provided by one or more service computers 704 via the HTTP protocol 706. Many RESTful APIs are based on the HTTP protocol. Thus, the focus is on the application layer in the following discussion. However, as discussed above with reference to FIG. 6, the remote client 702 and service provided by one or more server computers 704 are, in fact, physical systems with application, operating-system, and hardware layers that are interconnected with various types of communications media and communications subsystems, with the HTTP protocol the highest-level layer in a protocol stack implemented in the application, operating-system, and hardware layers of client computers and server computers. The service may be provided by one or more server computers, as discussed above in a preceding section. As one example, a number of servers may be hierarchically organized as various levels of intermediary servers and end-point servers. However, the entire collection of servers that together provide a service are addressed by a domain name included in a uniform resource identifier ("URI"), as further discussed below. A RESTful API is based on a small set of verbs, or operations, provided by the HTTP protocol and on resources, each uniquely identified by a corresponding URI. Resources are logical entities, information about which is stored on one or more servers that together comprise a domain. URIs are the unique names for resources. A resource about which information is stored on a server that is connected to the Internet has a unique URI that allows that information to be accessed by any client computer also connected to the Internet with proper authorization and privileges. URIs are thus globally unique identifiers, and can be used to specify resources on server computers throughout the world. A resource may be any logical entity, including people, digitally encoded documents, organizations, services, routines, and other such entities that can be described and characterized by digitally encoded information. A resource is thus a logical entity. Digitally encoded information that describes the resource and that can be accessed by a client computer from a server computer is referred to as a "representation" of the corresponding resource. As one example, when a resource is a web page, the representation of the resource may be a hypertext markup language ("HTML") encoding of the resource. As another example, when the resource is an employee of a company, the representation of the resource may be one or more records, each containing one or more fields, that store information characterizing the employee, such as the employee's name, address, phone number, job title, employment history, and other such information.

In the example shown in FIG. 7, the web servers 704 provides a RESTful API based on the HTTP protocol 706 and a hierarchically organized set of resources 708 that allow clients of the service to access information about the customers and orders placed by customers of the Acme Company. This service may be provided by the Acme Company itself or by a third-party information provider. All of the customer and order information is collectively represented by a customer information resource 710 associated with the URI "http://www.acme.com/customerInfo" 712. As discussed further, below, this single URI and the HTTP protocol together provide sufficient information for a remote client computer to access any of the particular types of customer and order information stored and distributed by the service 704. A customer information resource 710 represents a large number of subordinate resources. These subordinate resources include, for each of the customers of the Acme Company, a customer resource, such as customer resource 714. All of the customer resources 714-718 are collectively named or specified by the single URI "http://www.acme.com/customerInfo/customers" 720. Individual customer resources, such as customer resource 714, are associated with customer-identifier numbers and are each separately addressable by customer-resource-specific URIs, such as URI "http://www.acme.com/customerInfo/customers/361" 722 which includes the customer identifier "361" for the customer represented by customer resource 714. Each customer may be logically associated with one or more orders. For example, the customer represented by customer resource 714 is associated with three different orders 724-726, each represented by an order resource. All of the orders are collectively specified or named by a single URI "http://www.acme.com/customerInfo/orders" 736. All of the orders associated with the customer represented by resource 714, orders represented by order resources 724-726, can be collectively specified by the URI "http://www.acme.com/customerInfo/customers/361/orders" 738. A particular order, such as the order represented by order resource 724, may be specified by a unique URI associated with that order, such as URI "http://www.acme.com/customerInfo/customers/361/orders/1" 740, where the final "1" is an order number that specifies a particular order within the set of orders corresponding to the particular customer identified by the customer identifier "361."

In one sense, the URIs bear similarity to path names to files in file directories provided by computer operating systems. However, it should be appreciated that resources, unlike files, are logical entities rather than physical entities, such as the set of stored bytes that together compose a file within a computer system. When a file is accessed through a path name, a copy of a sequence of bytes that are stored in a memory or mass-storage device as a portion of that file are transferred to an accessing entity. By contrast, when a resource is accessed through a URI, a server computer returns a digitally encoded representation of the resource, rather than a copy of the resource. For example, when the resource is a human being, the service accessed via a URI specifying the human being may return alphanumeric encodings of various characteristics of the human being, a digitally encoded photograph or photographs, and other such information. Unlike the case of a file accessed through a path name, the representation of a resource is not a copy of the resource, but is instead some type of digitally encoded information with respect to the resource.

In the example RESTful API illustrated in FIG. 7, a client computer can use the verbs, or operations, of the HTTP protocol and the top-level URI 712 to navigate the entire hierarchy of resources 708 in order to obtain information about particular customers and about the orders that have been placed by particular customers.

FIGS. 8A-D illustrate four basic verbs, or operations, provided by the HTTP application-layer protocol used in RESTful applications. RESTful applications are client/server protocols in which a client issues an HTTP request message to a service or server and the service or server responds by returning a corresponding HTTP response message. FIGS. 8A-D use the illustration conventions discussed above with reference to FIG. 7 with regard to the client, service, and HTTP protocol. For simplicity and clarity of illustration, in each of these figures, a top portion illustrates the request and a lower portion illustrates the response. The remote client 802 and service 804 are shown as labeled rectangles, as in FIG. 7. A right-pointing solid arrow 806 represents sending of an HTTP request message from a remote client to the service and a left-pointing solid arrow 808 represents sending of a response message corresponding to the request message by the service to the remote client. For clarity and simplicity of illustration, the service 804 is shown associated with a few resources 810-812.

Figure 8A:
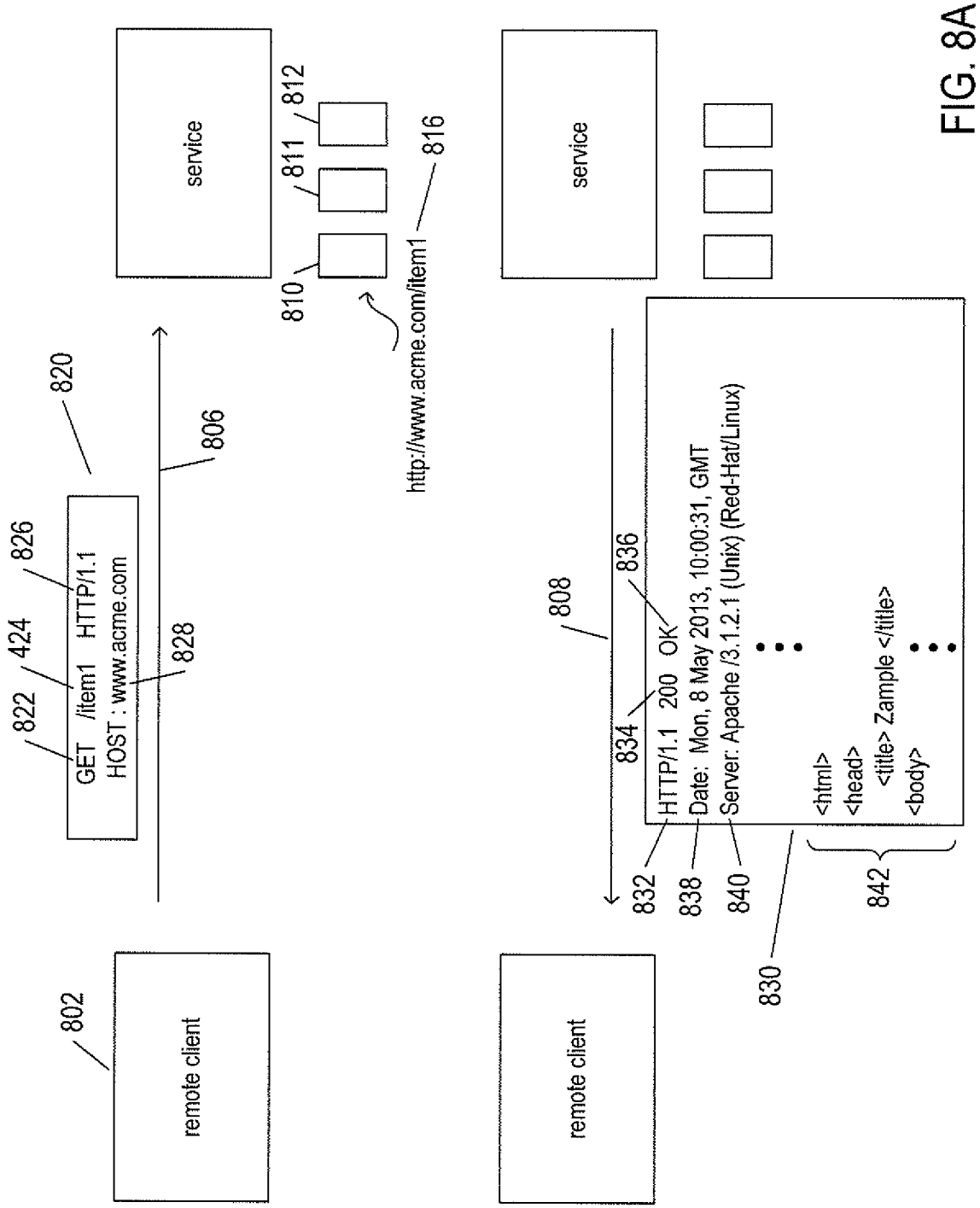
FIGS. 8A-D illustrate four basic verbs, or operations, provided by the HTTP application-layer protocol used in RESTful applications.

FIG. 8A illustrates the GET request and a typical response. The GET request requests the representation of a resource identified by a URI from a service. In the example shown in FIG. 8A, the resource 810 is uniquely identified by the URI "http://www.acme.com/item1" 816. The initial substring "http://www.acme.com" is a domain name that identifies the service. Thus, URI 816 can be thought of as specifying the resource "item1" that is located within and managed by the domain "www.acme.com." The GET request 820 includes the command "GET" 822, a relative resource identifier 824 that, when appended to the domain name, generates the URI that uniquely identifies the resource, and in an indication of the particular underlying application-layer protocol 826. A request message may include one or more headers, or key/value pairs, such as the host header 828 "Host:www.acme.com" that indicates the domain to which the request is directed. There are many different headers that may be included. In addition, a request message may also include a request-message body. The body may be encoded in any of various different self-describing encoding languages, often JSON, XML, or HTML. In the current example, there is no request-message body. The service receives the request message containing the GET command, processes the message, and returns a corresponding response message 830. The response message includes an indication of the application-layer protocol 832, a numeric status 834, a textual status 836, various headers 838 and 840, and, in the current example, a body 842 that includes the HTML encoding of a web page. Again, however, the body may contain any of many different types of information, such as a JSON object that encodes a personnel file, customer description, or order description. GET is the most fundamental and generally most often used verb, or function, of the HTTP protocol.

Figure 8B:
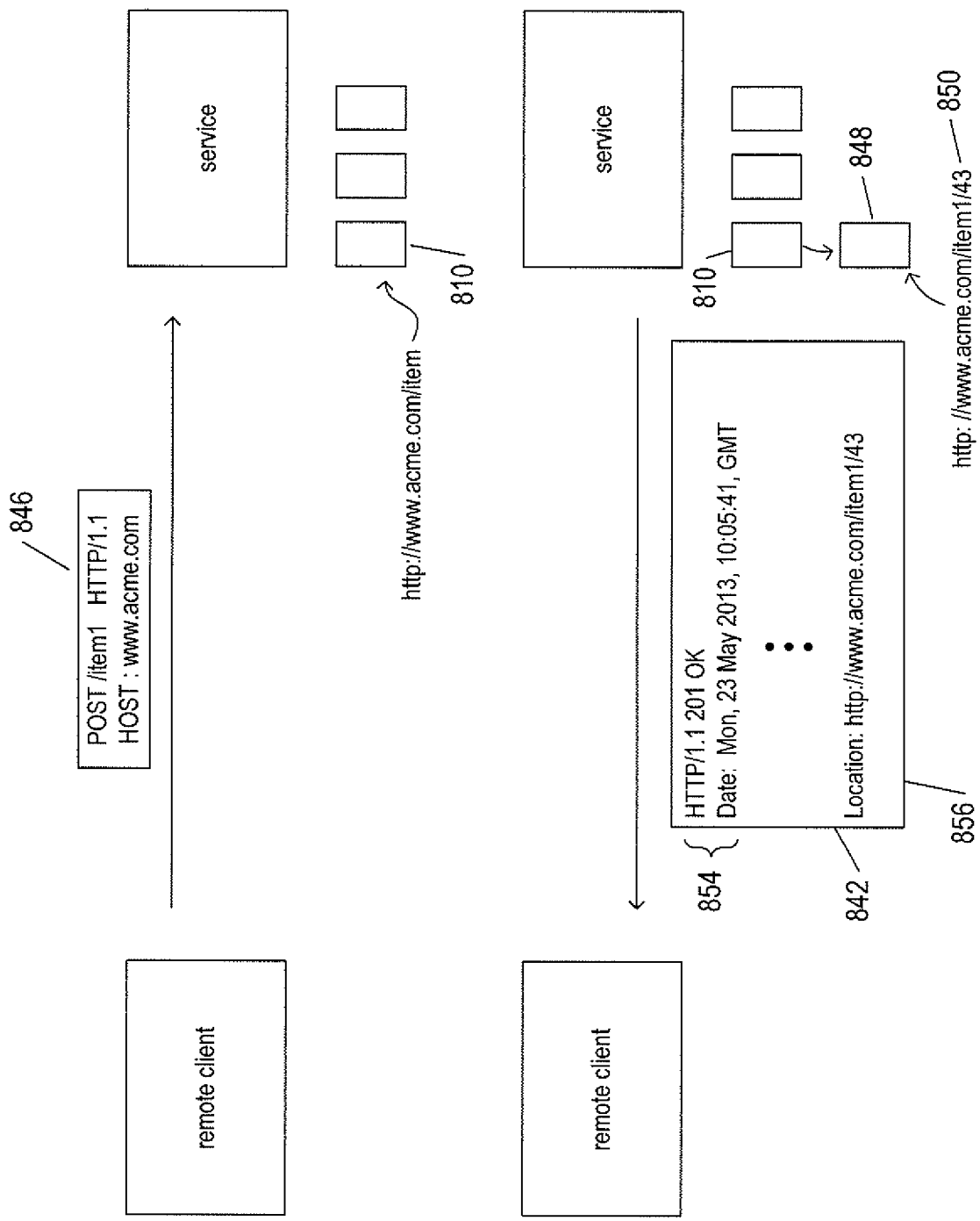

FIG. 8B illustrates the POST HTTP verb. In FIG. 8B, the client sends a POST request 846 to the service that is associated with the URI "http://www.acme.com/item1." In many RESTful APIs, a POST request message requests that the service create a new resource subordinate to the URI associated with the POST request and provide a name and corresponding URI for the newly created resource. Thus, as shown in FIG. 8B, the service creates a new resource 848 subordinate to resource 810 specified by URI "http://www.acme.com/item1," and assigns an identifier "36" to this new resource, creating for the new resource the unique URI "http://www.acme.com/item1/36" 850. The service then transmits a response message 852 corresponding to the POST request back to the remote client. In addition to the application-layer protocol, status, and headers 854, the response message includes a location header 856 with the URI of the newly created resource. According to the HTTP protocol, the POST verb may also be used to update existing resources by including a body with update information. However, RESTful APIs generally use POST for creation of new resources when the names for the new resources are determined by the service. The POST request 846 may include a body containing a representation or partial representation of the resource that may be incorporated into stored information for the resource by the service.

Figure 8C:
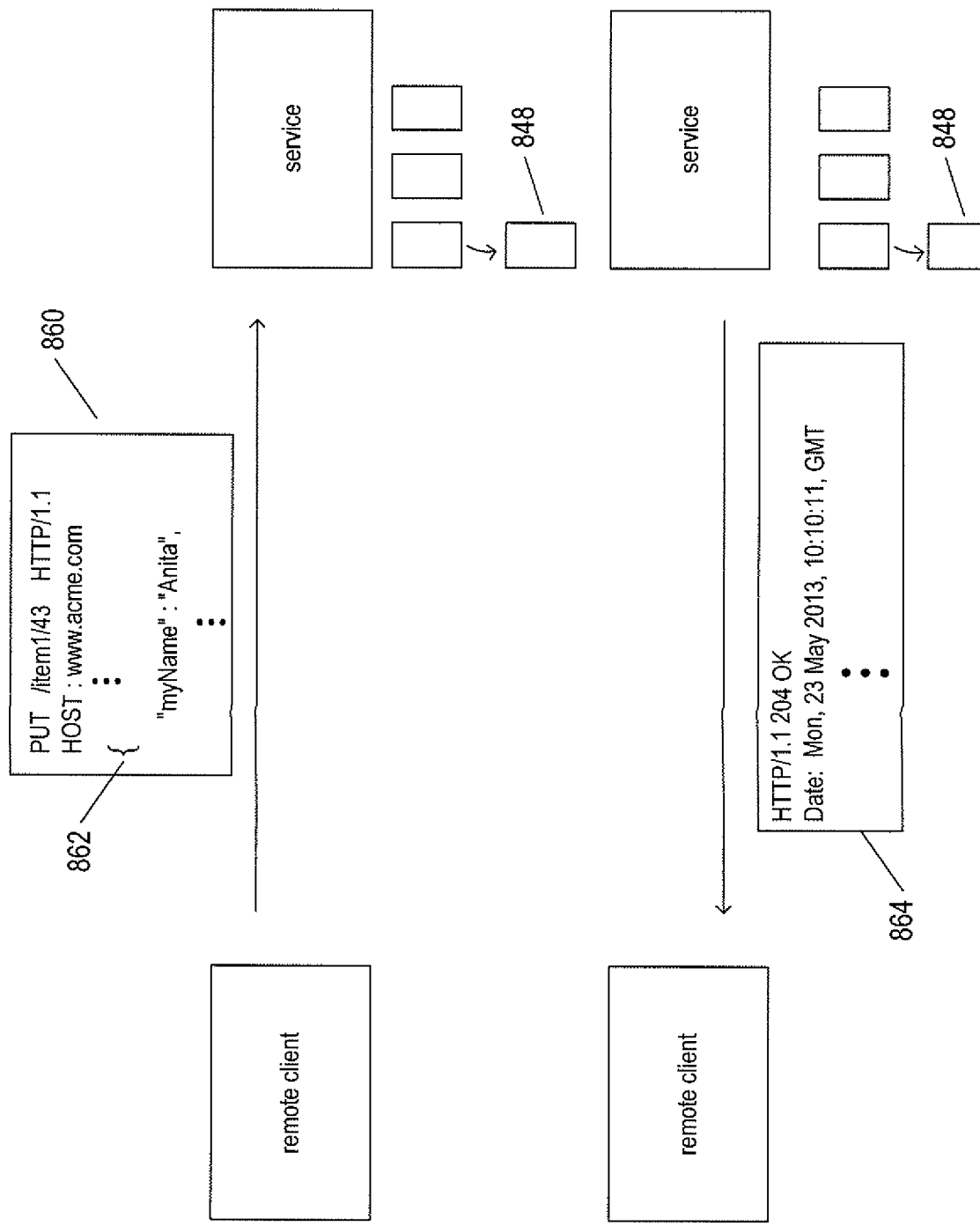

FIG. 8C illustrates the PUT HTTP verb. In RESTful APIs, the PUT HTTP verb is generally used for updating existing resources or for creating new resources when the name for the new resources is determined by the client, rather than the service. In the example shown in FIG. 8C, the remote client issues a PUT HTTP request 860 with respect to the URI "http://www.acme.com/item1/36" that names the newly created resource 848. The PUT request message includes a body with a JSON encoding of a representation or partial representation of the resource 862. In response to receiving this request, the service updates resource 848 to include the information 862 transmitted in the PUT request and then returns a response corresponding to the PUT request 864 to the remote client.

Figure 8D:
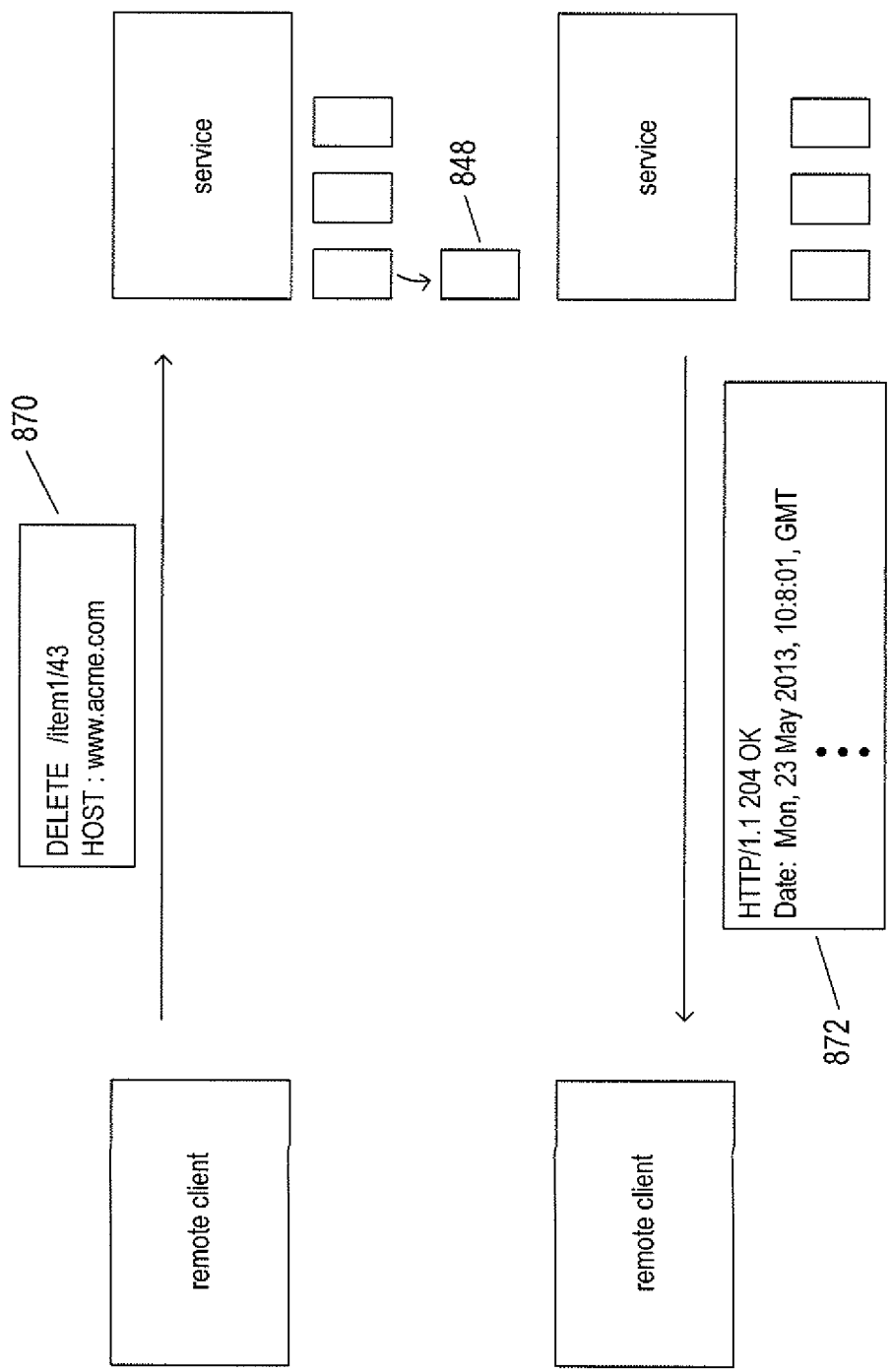

FIG. 8D illustrates the DELETE HTTP verb. In the example shown in FIG. 8D, the remote client transmits a DELETE HTTP request 870 with respect to URI "http://www.acme.com/item1/36" that uniquely specifies newly created resource 848 to the service. In response, the service deletes the resource associated with the URL and returns a response message 872.

A service may return, in response messages, various different links, or URIs, in addition to a resource representation. These links may indicate, to the client, additional resources related in various different ways to the resource specified by the URI associated with the corresponding request message. As one example, when the information returned to a client in response to a request is too large for a single HTTP response message, it may be divided into pages, with the first page returned along with additional links, or URIs, that allow the client to retrieve the remaining pages using additional GET requests. As another example, in response to an initial GET request for the customer info resource (710 in FIG. 7), the service may provide URIs 720 and 736 in addition to a requested representation to the client, using which the client may begin to traverse the hierarchical resource organization in subsequent GET requests.

Overview of DNA and Genomics Information

Figure 9:
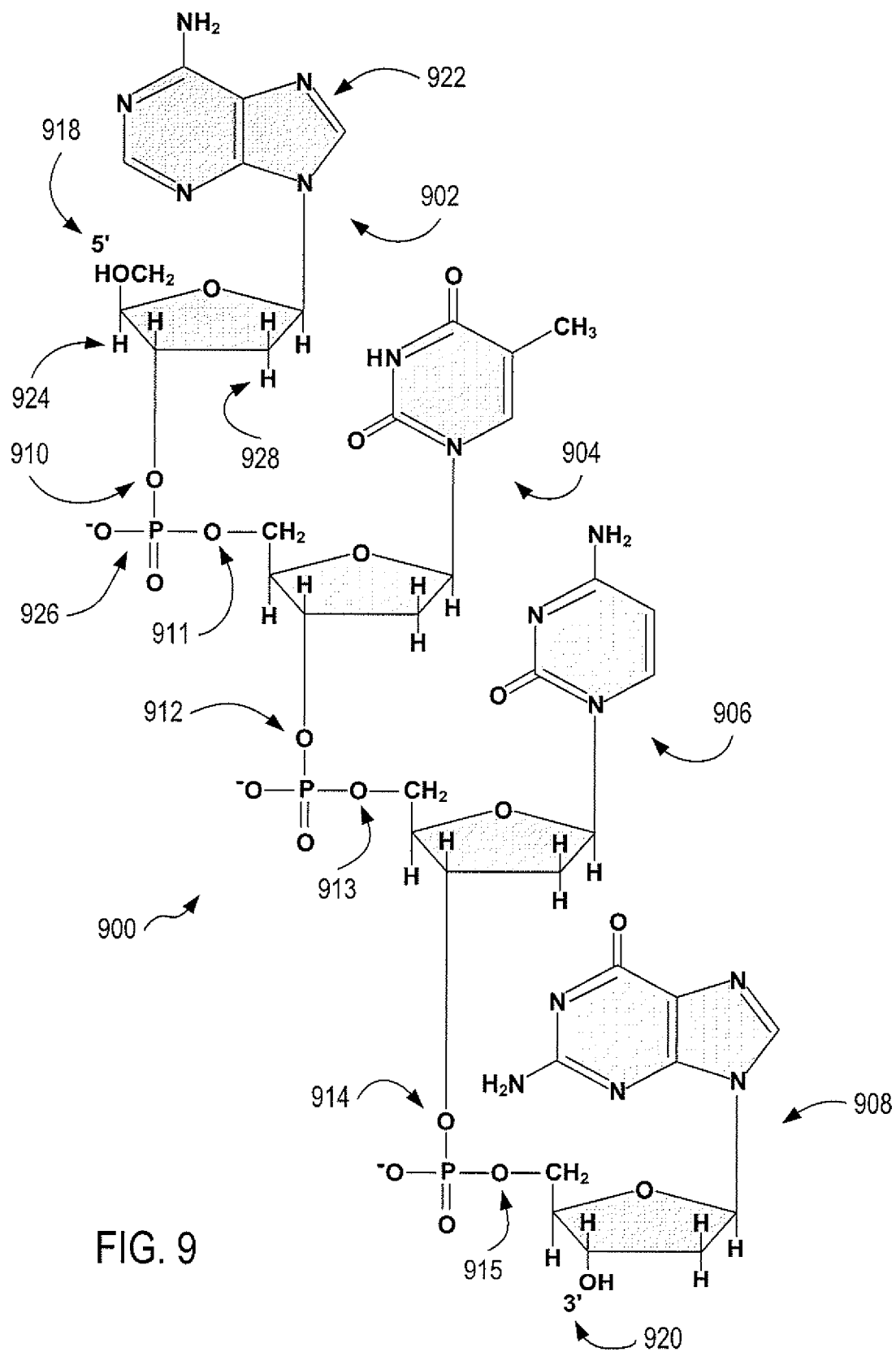
FIG. 9 illustrates a short DNA polymer.

FIG. 9 illustrates a short DNA polymer. Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 902; (2) deoxy-thymidine 904; (3) deoxy-cytosine 906; and (4) deoxy-guanosine 908. When phosphorylated, subunits of DNA and RNA molecules are called "nucleotides" and are linked together through phosphodiester bonds 910-915 to form DNA and RNA polymers. A linear DNA molecule, such as the oligomer shown in FIG. 9, has a 5' end 918 and a 3' end 920. A DNA polymer can be chemically characterized by writing, in sequence from the 5' end to the 3' end, the single letter abbreviations for the nucleotide subunits that together compose the DNA polymer. For example, the oligomer 900 shown in FIG. 9 can be chemically represented as "ATCG." A DNA nucleotide comprises a purine or pyrimidine base (e.g. adenine 922 of the deoxy-adenylate nucleotide 902), a deoxy-ribose sugar (e.g. deoxy-ribose 924 of the deoxy-adenylate nucleotide 902), and a phosphate group (e.g. phosphate 926) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 928 in a DNA nucleotide. RNA polymers contain uridine nucleosides rather than the deoxy-thymidine nucleosides contained in DNA. The pyrimidine base uracil lacks a methyl group (930 in FIG. 9) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

Figure 10A:
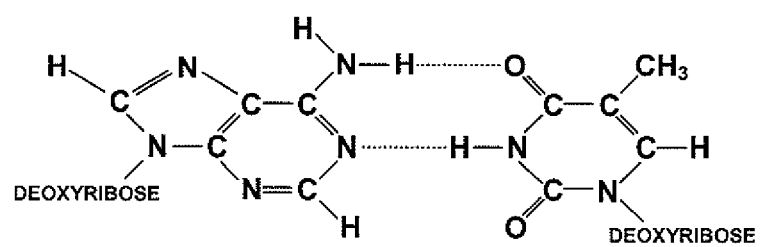
FIGS. 10A-B illustrate hydrogen bonding between the purine and pyrimidine bases of two anti-parallel DNA strands.
Figure 10B:
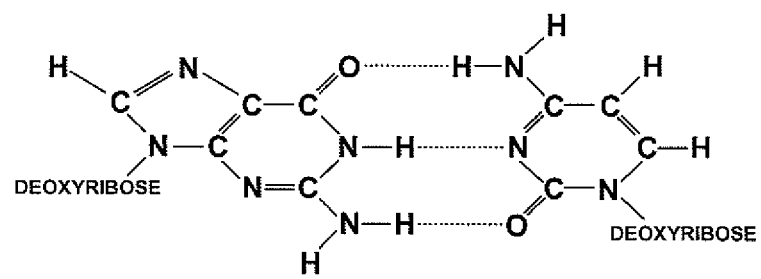

FIGS. 10A-B illustrate the hydrogen bonding between the purine and pyrimidine bases of two anti-parallel DNA strands. FIG. 10A shows hydrogen bonding between adenine and thymine bases of corresponding adenosine and thymidine subunits, and FIG. 10B shows hydrogen bonding between guanine and cytosine bases of corresponding guanosine and cytosine subunits. Note that there are two hydrogen bonds 1002 and 1003 in the adenine/thymine base pair, and three hydrogen bonds 1004-1006 in the guanosine/cytosine base pair, as a result of which GC base pairs contribute greater thermodynamic stability to DNA duplexes than AT base pairs. AT and GC base pairs, illustrated in FIGS. 10A-B, are known as Watson-Crick ("WC") base pairs.

Figure 11:
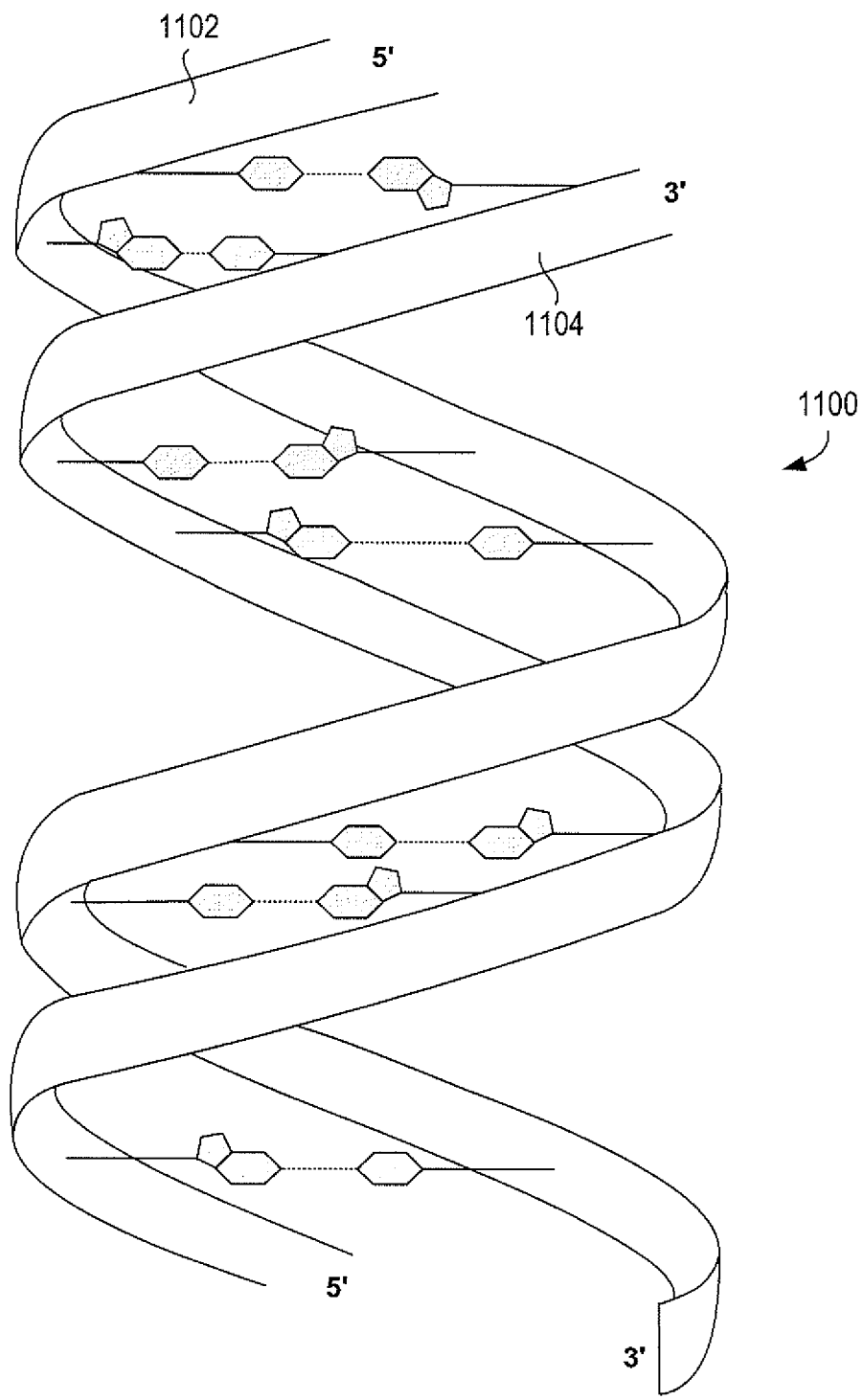
FIG. 11 illustrates a short section of a DNA double helix 300 comprising a first strand 302 and a second, anti-parallel strand 304.

Two DNA strands linked together by hydrogen bonds forms the familiar helix structure of a double-stranded DNA helix. FIG. 11 illustrates a short section of a DNA double helix 1100 comprising a first strand 1102 and a second, anti-parallel strand 1104. The ribbon-like strands in FIG. 11 represent the deoxyribose and phosphate backbones of the two anti-parallel strands, with hydrogen-bonding purine and pyrimidine base pairs, such as base pair 1106, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA. Generally, purine/pyrimidine non-WC base pairings contribute little to the thermodynamic stability of a DNA duplex, but generally do not destabilize a duplex otherwise stabilized by WC base pairs. However, purine/purine base pairs may destabilize DNA duplexes.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to regions of DNA duplex. Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

The DNA in living organisms occurs as extremely long double-stranded DNA polymers known as chromosomes. Each chromosome may contain millions of base pairs. The base-pair sequence in a chromosome is logically viewed as a set of long subsequences that include regulatory regions to which various biological molecules may bind, structural regions consisting of repeated short sequences, and genes. A gene generally encodes the amino-acid sequence of a protein, with base-pair triples, referred to as "codons," within the exon region of a gene coding for specific amino acids within the protein.

When cells divide, the double-stranded chromosomes are replicated in a process logically equivalent to separating the two DNA strands of a chromosome and synthesizing a new, complementary strand for each of the two separated strands, resulting in two chromosomes, each containing an original strand and a newly synthesized strand. DNA synthesis is carried out by enzymes called "DNA polymerases." These enzymes polymerize nucleotide triphosphate monomers into a DNA polymer complementary to a DNA polymer that serves as a template for the DNA polymerases.

Genes are transcribed in an organism by an RNA polymerase to produce messenger RNA molecules ("mRNA") that, in turn, serve as templates for translation of the base-pair sequence of the mRNA into protein molecules. The amino-acid sequence of protein molecules is thus determined by the base-pair sequence of the messenger RNA, which is, in turn, complementary to, and determined by, the base-pair sequence within a corresponding gene.

In general, the organisms within a species commonly share the DNA sequences of the genes contained within their chromosomes. However, slight variations of gene sequences occur within the individuals of each species. These slight variations are reflected in the biochemical and physical characteristics of individuals of the species. Hair color, eye color, growth patterns, disease susceptibility, metabolism, and many other characteristics that vary among individuals of a species are attributable to variations in gene sequences. In addition, non-protein-coding regions of the genome are also shared, in some cases as conservatively or more conservatively as protein-coding regions, and, in other cases, less conservatively. Sequence differences in non-protein-coding regions between individuals may also lead to observably different traits and characteristics of the individuals. For example, genes are generally associated with DNA regulatory sequences that provide a basis for transcriptional control of gene expression. A change in a regulatory sequence may as effectively lead to low concentrations or the absence of a protein as a serious mutation in the gene encoding the protein.

Figure 12:
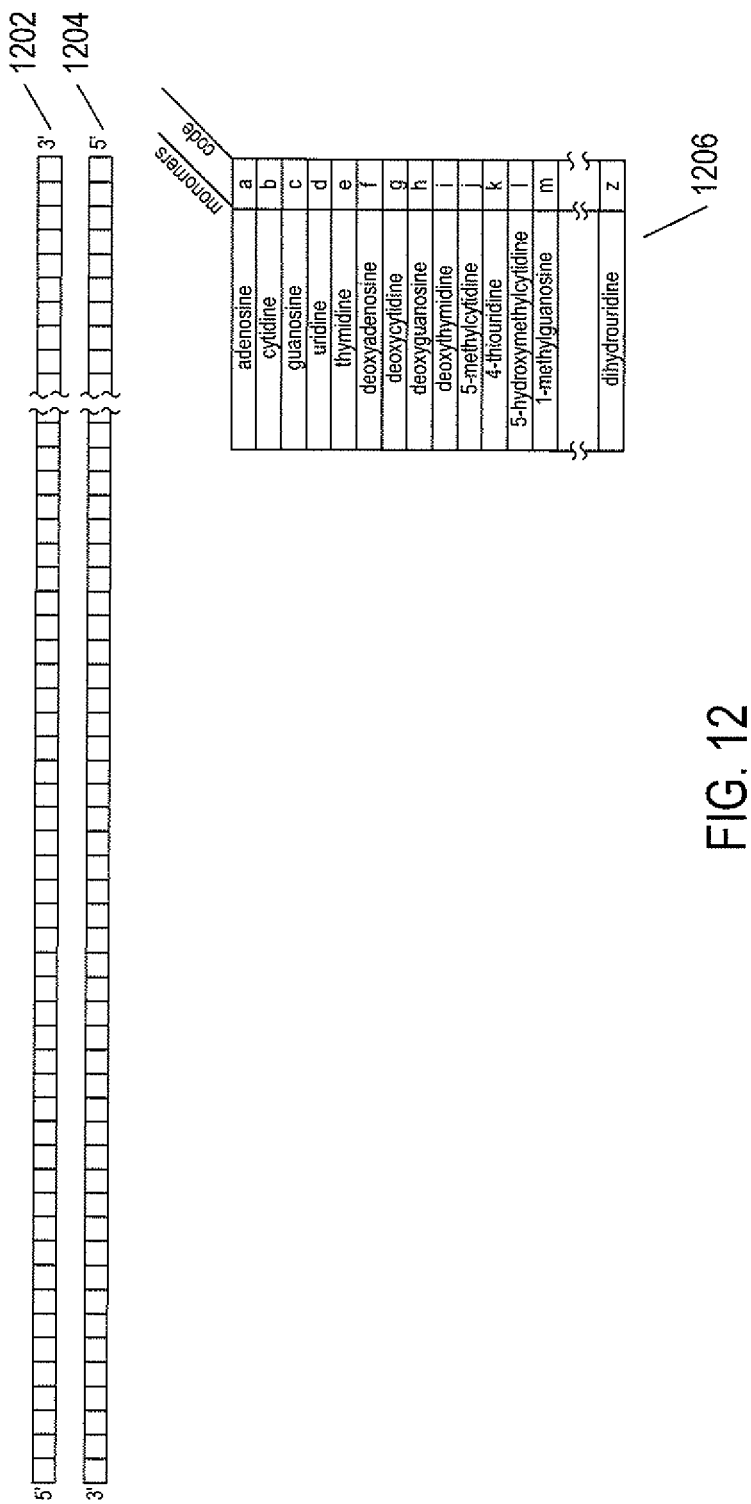
FIG. 12 illustrates the representation of the base sequence of a double-stranded DNA polymer.

FIG. 12 illustrates the representation of the base sequence of a double-stranded DNA polymer. The double-stranded polymer includes a 5'-to-3' forward strand 1202 and a 3'-to-5' reverse strand 1204, with the identity of the nucleotides in each strand represented by a code within a byte or word data-storage unit. In this representation, the forward strand and reverse strand are essentially each represented by an array of bytes or words, each code standing for a monomer that occurs at a position within the double-stranded DNA polymer equivalent to the position of the code within the array. Two codes with the same index represent a base pair that, in the actual DNA polymer, generally comprises complementary nucleotides with bases bound together via hydrogen bonds, as discussed above. The representation also includes a table 1206 that lists different possible monomers along with their corresponding numerical codes. Although, in general, DNA contains deoxyadenosine, deoxycytidine, deoxyguanosine, and deoxythymidine monomers, DNA polymers may additionally contain the RNA monomers adenosine, cytidine, guanosine, and uridine as well as many additional monomers that result from various chemical modifications of the standard DNA and RNA monomers.

Figure 13:
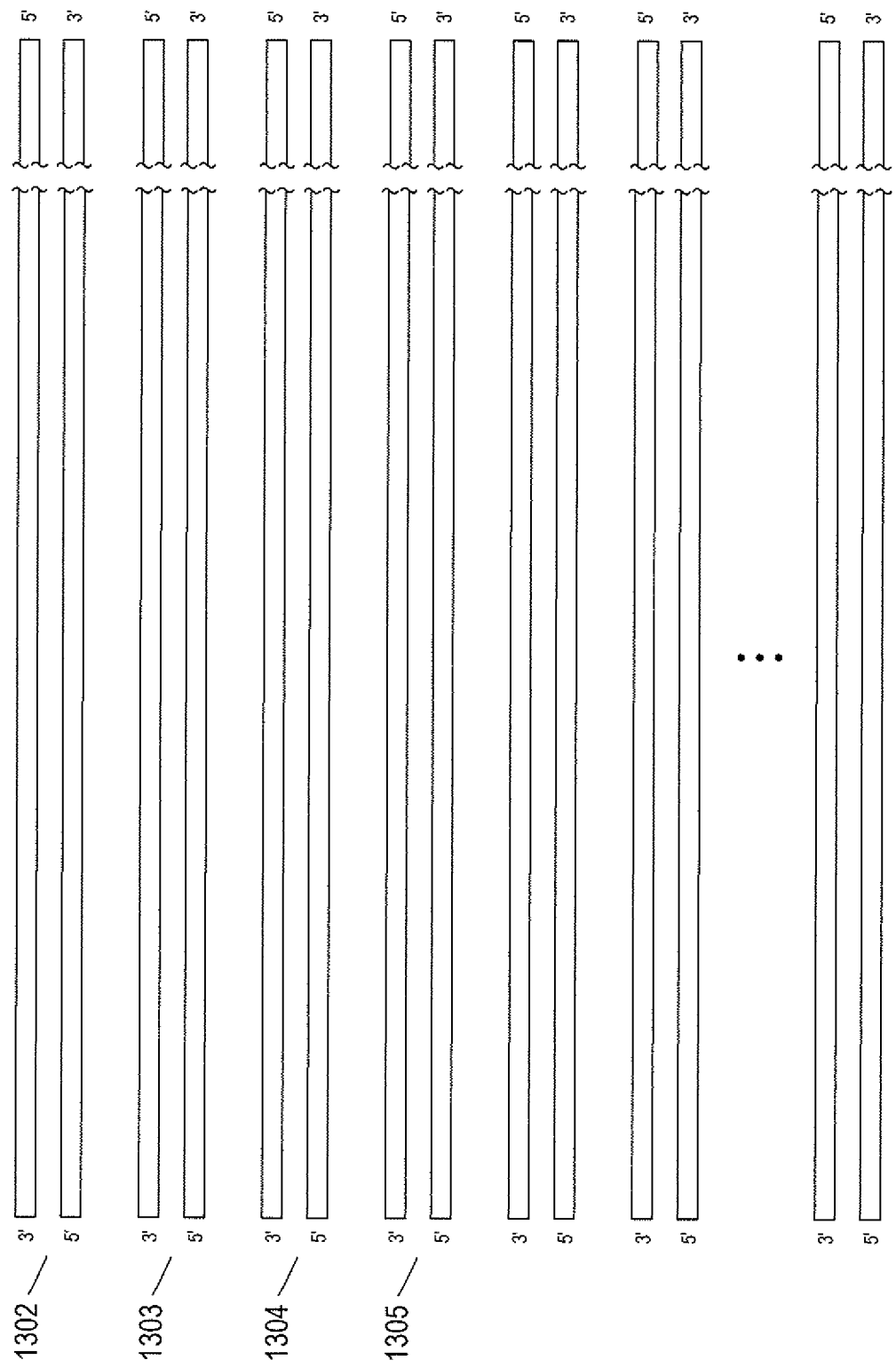
FIG. 13 shows the representation of an entire genome for an organism, such as a human being.

In eukaryotes, genetic information is contained in chromosomes. Each chromosome is a very long double-stranded DNA polymer associated with a large number of proteins. Human cells contain 23 pairs of chromosomes: 22 pairs are the same in both females and males and are called "autosomes." The $23^{rd}$ pair corresponds to the sex chromosomes with either two X chromosomes in females or an X chromosome and a Y chromosome in males. For each pair of chromosomes, one chromosome is inherited from the mother and the other chromosome of the pair is inherited from the father. FIG. 13 shows the representation of an entire genome for an organism, such as a human being. The representation includes a pair of double-stranded DNA polymers for each of the 22 chromosomes and one double-stranded DNA polymer for each sex chromosome. For example, in FIG. 13, double-stranded DNA polymers 1302 and 1303 may together represent chromosome 1, double-stranded DNA polymers 1304 and 1305 may represent chromosome 2, and so on. Because the forward strand is complementary to the reversed strand, and vice-versa, for many purposes, it would be sufficient to store the representation of the sequence of one of the two strands of a double-stranded DNA, since the other strand can be computationally generated from the storage strand.

FIGS. 14A-B illustrate information encoding within a double-stranded DNA polymer and types of variant sequences encountered in natural DNA. In FIG. 14A, a double-stranded DNA polymer 1402 is shown as a forward strand 1404 and a reverse strand 1406. Various types of regions are shown along the forward strand 1404 with different types of cross-hatching and patterns. Two regions 1406 and 1408 are genes. Genes represent encodings for the amino-acid sequences of protein polymers. Each successive group of three nucleotide monomers within the amino-acid coding portions of a gene encode a single amino acid. Genes are transcribed into mRNA transcripts which are then generally edited and then processed, or translated, into protein polymers. Transcript editing may involve removing intron regions and splicing together the remaining exons. Proteins function as enzymes that catalyze chemical reactions within an organism, as structural elements of cells, as transporter and carrier molecules, as regulatory elements involved in controlling gene transcription, and in a variety of additional roles. When a gene is transcribed, one of the two strands of the DNA double-stranded polymer is read, in the 3'-to-5' direction, by an RNA polymerase, which generates a corresponding RNA transcript in the 5'-to-3' direction. The strand that is transcribed is referred to as the "template" strand while the other strand is referred to as the "coding" strand, since the mRNA polymer produced by the RNA polymerase has the same directionality and a sequence equivalent to the sequence of the coding strand. In a double-stranded DNA-polymer chromosome, the template for a particular gene may be on either of the forward 1404 or reverse 1406 strands, but it is always on the same strand for that gene. In other words, a gene may be transcribed in either of two different directions, but each gene is always transcribed in the same direction. In addition to genes, DNA double-stranded polymers may include other types of subsequences, including promoter subsequences, such as subsequence 1410, that are involved in the initiation of transcription, enhancer subsequences, such as enhancer 1412, that may increase the frequency of transcription, and non-protein-encoding sequences, such as subsequence 1414, that may be transcribed to produce ribozymes and other RNA polymers involved in a variety of different types of cellular processes. In order to classify the different types of information-encoding regions, or subsequences, within a double-stranded DNA polymer, a table, such as table 1416, may be used to list each DNA region and associated function. In the examples shown in FIG. 14A, the table has five columns corresponding to five fields for each entry, or row. These fields include: (1) ID 1418, an alphanumeric identifier for the subsequence; (2) type 1420, a numeric indication of the type of the subsequence, such as gene, promoter, enhancer, and various different types of non-protein-coding sequences; (3) start 1422, a starting position, using nucleotides as unit of distance, representing an offset from a zero or reference position 1424; (4) length 1426, the length of the subsequence in nucleotides; and (5) t/c 1428, an indication, for genes, whether the sequence is the coding sequence or template sequence for the gene. This final column is used, in particular, when the sequence of only one of the two strands of the double-stranded polymer are stored in a sequence database. Of course, there are many alternative ways of encoding and storing DNA sequence information for double-stranded DNA polymers of chromosomes.

FIG. 14B shows the subsequence, in the 5'-to-3' direction, for gene 1406 discussed in FIG. 14A. Each cell in the array-like representation, such as the first cell 1430, represents a nucleotide monomer. It is often the case that the sequence of a gene observed in different individuals may differ from one individual to another. Normally, a reference sequence for one individual or a composite sequence assembled from multiple individuals is stored, in its entirety, in a genome-sequence database. Genetic data for individual patients can then be stored as a list of variations, or variants, with respect to the reference sequence. There are many types of variations in gene sequences that naturally occur. These include base changes, insertions, and deletions. In FIG. 14B, table 1432 represents variations in a gene observed for a patient with respect to a reference sequence for the gene. The nucleotide 1434 at position 2624 is different, in the particular patient, than the nucleotide present at that location in the reference sequence. This type of base change is referred to as a "single nucleotide polymorphism," or "SNP," and can be entered into table 1432 as a row or entry, such as the first row or entry 1436 which specifies the SNP 1434 using an alphanumeric identifier, ID 1438, for the SNP, an indication of the type of SNP, or identity of the base change 1440, the starting point of the variation 1442, in nucleotide units from a reference point, and the length of the variation, in this case one nucleotide 1444. Another type of variation may be the deletion of one or more bases. In FIG. 14B, the gene sequence for the individual patient includes a four-base deletion 1446 that begins at nucleotide 2632. Row 1448 in table 1432 represents this deletion. Another type of variation is an insertion. In the example gene sequence shown in FIG. 14B, there is a six-nucleotide insertion 1450 that occurs prior to the referenced nucleotide at position 2638. This insertion is represented in the table by a third row 1452 that, in addition to an ID, type, starting point, and length, includes an indication of the inserted, or added, nucleotide subsequence 1454. Again, as with the encodings of the different types of information units along a DNA double-stranded polymer discussed with reference to FIG. 14A, there are many different ways of listing the variations in a gene that occur in individual patients. As one example, the starting points for the deletions, insertions, and SNPs may be encoded relative to the first nucleotide of the gene rather than relative to the reference starting point for the chromosome containing the gene. Rather than using only sequences for the forward or reverse strand, sequences for all or portions of both the reference and forward strands may be used, both for the reference sequence and the variants, with additional columns/fields indicating to which of the two strands the tabular information relates. Additional columns/fields may be used to indicate the chromosome and gene to which a variant belongs, in the case of table 1432, and the chromosome to which various types of regions belong, in the case of table 1416. There are many additional types of variations, including changes in the nucleotide of two or more successive positions, chromosomal relocations, inversions of portions of a DNA polymer, and other such variations. There are also different ways for choosing the reference or zero points for nucleotide positions both within chromosomes and within genes. When multiple conventions are employed within a given genetic database, then additional column/field information may be added to tables in order to indicate the particular convention used for a particular entry.

Cloud-Like Medical-Information Systems and Clinical-Knowledge Data Structures

Figure 15:
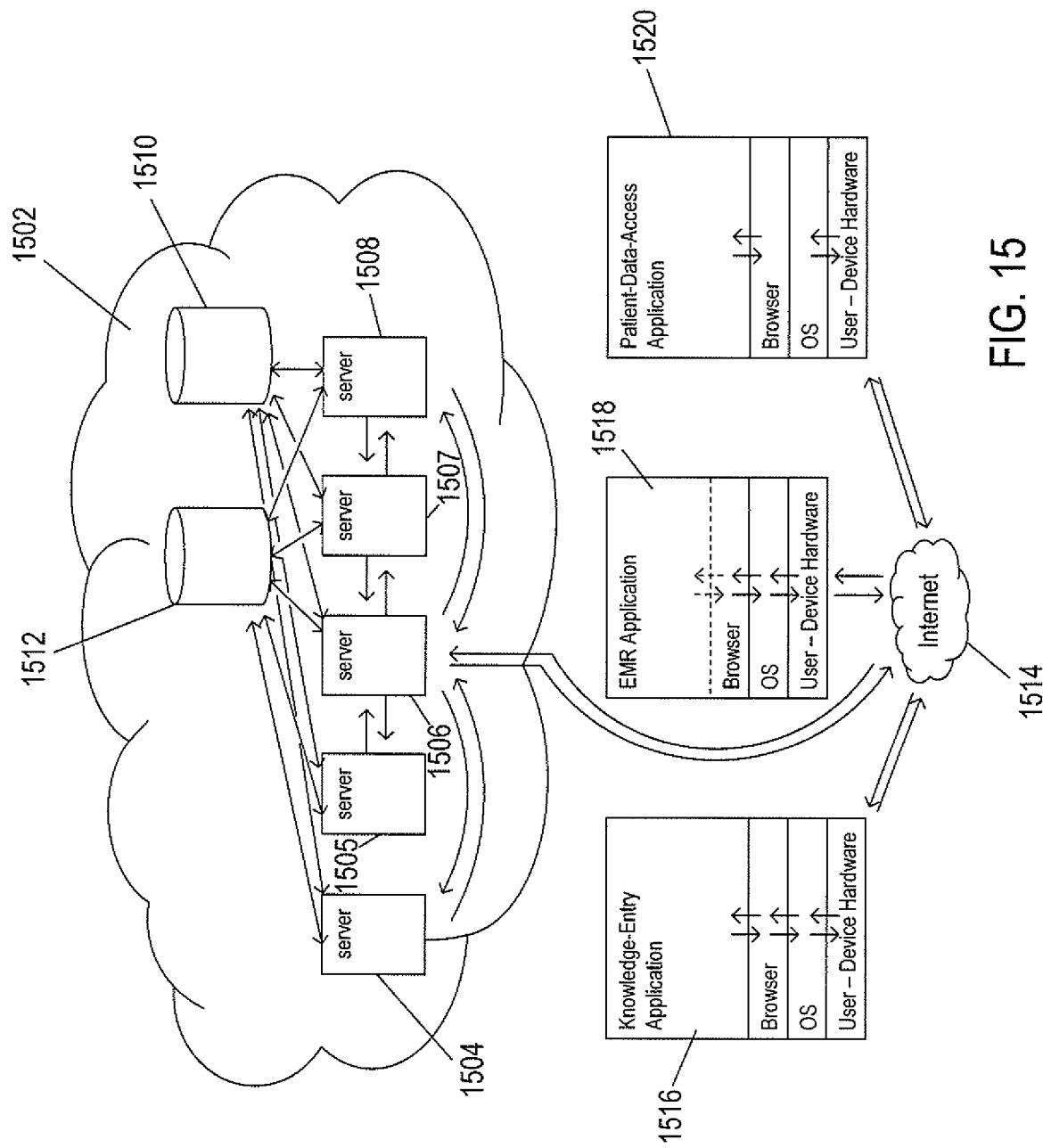
FIG. 15 provides a high-level illustration of one implementation of a cloud-like medical-information system to which the current document is directed.

FIG. 15 provides a high-level illustration of one implementation of a cloud-like medical-information system to which the current document is directed. The cloud-like medical-information system 1502 is implemented within a cloud-like data center comprising multiple virtual servers 1504-1508 that provide a variety of different services as well as cloud-like data-storage facilities 1510 and 1512. A request-processing service, implemented in one or more virtual servers 1506, receives, through the Internet 1514, various types of requests from various types of users and user applications and requests processing of the requests by calling additional services implemented on multiple virtual servers 1504-1505 and 1507-1508 within the cloud-like medical-information system. The cloud-like data-storage facilities 1510 and 1512 store network-like clinical-knowledge data structures, genomic variant data for individual patients, additional patient information, and a variety of administrative and account-management information. Applications that access the cloud-like medical-information service on behalf of various types of users include knowledge-entry applications 1516, electronic-health-record ("EHR") applications 1518, and various types of patient-data-access applications 1520. Knowledge-entry applications include applications used by scientists, researchers, and clinicians to input and edit various types of clinical knowledge stored within the data facilities of the cloud-like medical-information system. EHR applications may include various types of applications used by medical-service providers and medical-service organizations, home-health systems, pharmacy systems, applications directly used by patients, and other systems that access and/or store medical information included in electronic health records.

As one example, geneticists may use genomics-information-entry applications to enter information about variants, reference genomes, information elements within reference genomes, and clinical information related to genomics information, such as characterizations of various diseases, physiological impacts, and pathologies associated with particular genetic variants, information about potential treatments and screening methods, including risk reduction and treatment and screening effectiveness, associated with particular genetic variants, information about potential variations in the effectiveness, dosing, or adverse effects of pharmaceuticals in patients with particular genetic variations, and other such information. The information may be entered in many different forms to accommodate the wide variety of variation in genomic data, and may be accompanied by citations to medical and scientific journals and links to a variety of other information sources. The cloud-like medical-information system can tolerate receiving information in many forms and using many different notation conventions, both in input scientific information as well as in queries, because the cloud-like medical-information system includes internal logic for normalizing and standardizing terminology and phraseology in order to facilitate accurate searching and retrieval and to avoid unnecessary redundancy in stored data. EHR applications may include a wide variety of different types of clinical applications used by medical-service providers. For example, during or at the end of an office visit or consultation, a physician may enter data into one or more electronic health records, via an EHR application, in order to describe what the physician observed and to record actions taken by the physician, such as prescribing of medications, ordering of tests, and referrals to specialists. As information is entered into the application, such as information related to creating a prescription or reviewing existing prescriptions, the EHR application may make a call to the cloud-like medical-information service to request that the cloud-like medical-information service compare genetic variants associated with the patient to medication-related clinical knowledge in order to identify any potential problems or conditions that might arise for the patient due to the patients gene variants. The response from the cloud-like medical-information service may then be displayed to the physician by the EHR application, should potential problems be identified, allowing the physician to alter the medications prescribed to the patient or select alternative treatment methods. As another example, as the physician enters a description of a diagnosis or planned treatment, which may be translated into various medical codes, the EHR application may request the cloud-like medical-information service to compare the patient's gene variants with the clinical knowledge maintained by the cloud-like medical-information service in order to find any genomic indications that would support or argue against the diagnosis or planned therapy. As a third example, a physician may view a patient's genomic profile, associated actionable medical risks, and recommendations stored by the cloud-like medical-information service.

These are but three of many different possible types of requests that may be made by EHR applications to the cloud-like medical-information service. Patient-data-access applications may allow patients to view their own gene-variant information and other such medical information stored within the cloud-like medical-information service on behalf of the patient. In addition, the patient may be allowed to access certain portions of the clinical knowledge stored and maintained by the cloud-like medical-information service. Other patient-data-access applications may allow physicians and other medical-service providers to request and receive information related to a patient as well as portions of the stored clinical knowledge. In all cases, as discussed in more detail below, access to information stored by the cloud-like medical-information service requires user authentication and authorization and all information exchanges, both between the cloud-like medical-information service and remote clients as well as between virtual servers and data-storage facilities within the cloud-like medical-information service are protected by multiple levels of security, including encryption, secure communications protocols, and digital signatures. Only those medical-services providers authorized by a patient, for example, can access patient data and an authorized medical-services provider can only access that portion of a patient's data authorized for access by that medical-services provider by the patient. Request/response transactions between external, remote users in the cloud-like medical-information service are communicated using REST/HTTP-based protocols, in one implementation.

In the case of EHR applications, it is a design specification of the medical-information services that responses to requests be received by requesting EHR applications in under one second. Otherwise, embedding queries to the cloud-like medical-information service within EHR applications may introduce unacceptable delays in EHR processing. The design for the currently described implementation of the cloud-like medical-information service has been significantly shaped and structured as a result of this query/response time constraint. This time constraint is particularly significant when the amount of clinical-knowledge data constantly being made available by scientific research is considered along with additional constraints, including the constraint of employing secure communications to communicate with the cloud-like medical-information service.

Figure 16A:
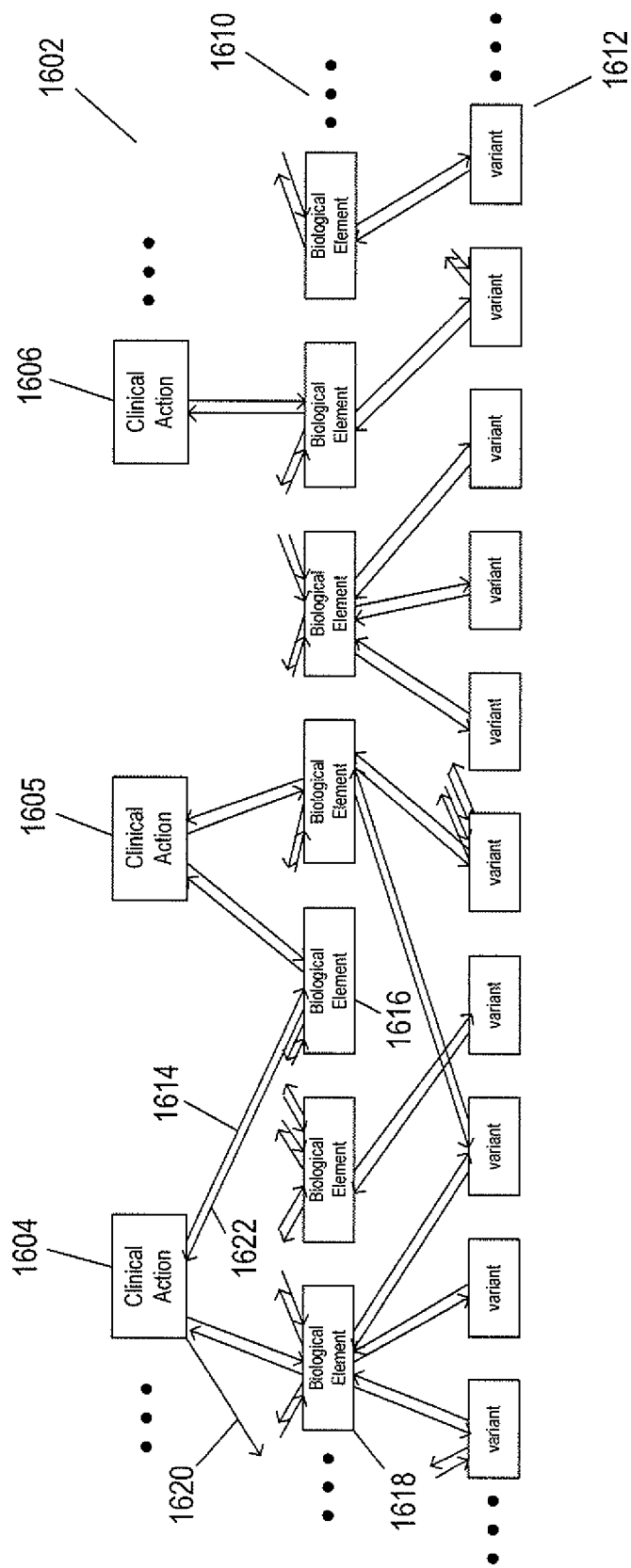
FIGS. 16A-B illustrate, at a high level, the network-like clinical-knowledge data structure that stores clinical knowledge that is used by the cloud-like medical-information service to process queries with respect to individual patients.
Figure 16B:
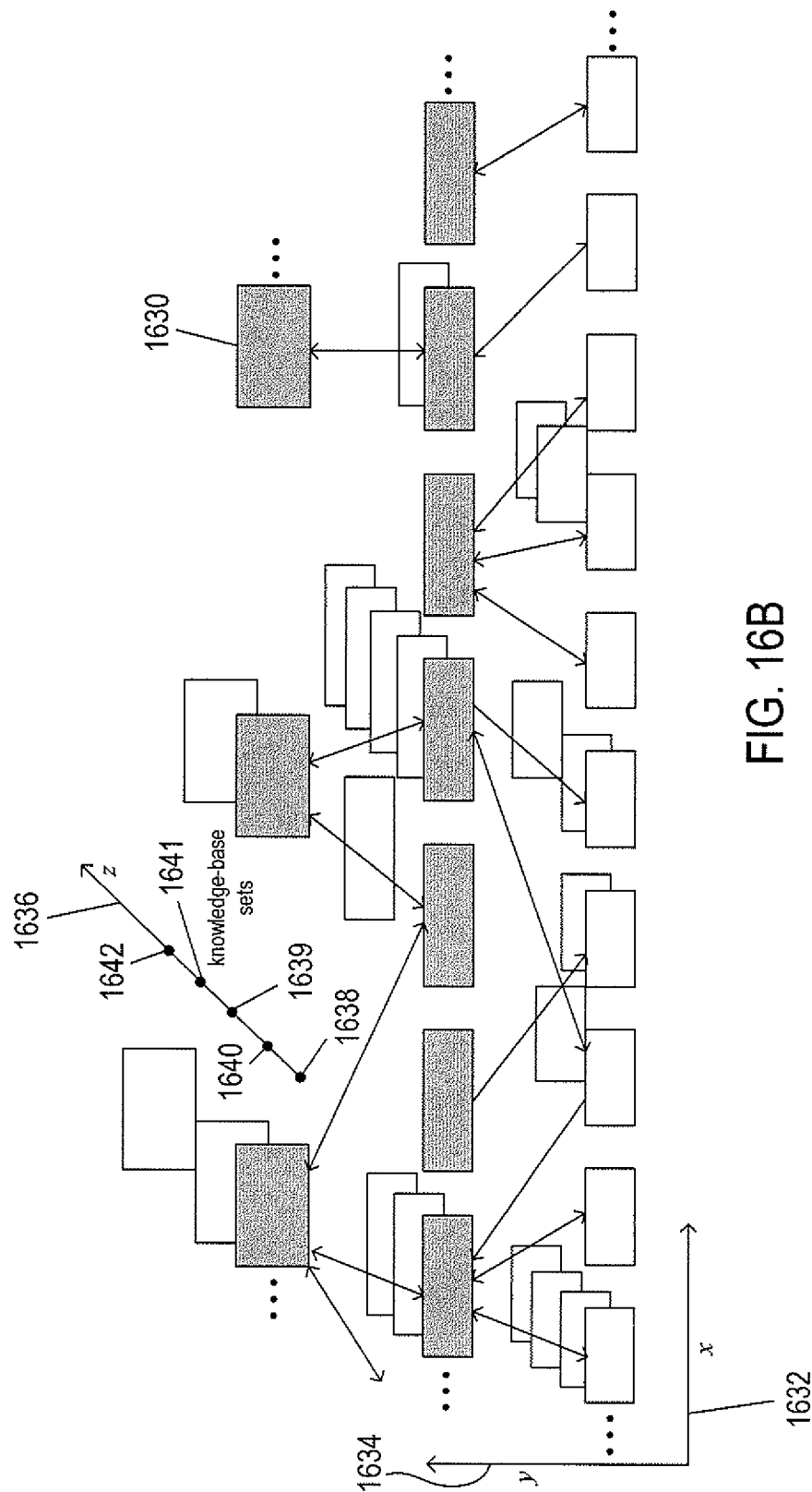

FIGS. 16A-B illustrate, at a high level, the network-like clinical-knowledge data structure that stores clinical knowledge that is used by the cloud-like medical-information service to process queries with respect to individual patients. As mentioned above, the description of the cloud-like medical-information service provided in the current document focuses on the genomics component of clinical knowledge. Other types of clinical knowledge, such as clinical knowledge related to the microbiome, may involve additional types of nodes and links. FIG. 16A shows a small portion of the network-like clinical-knowledge data structure. The data structure is hierarchical, with three different levels, each containing a particular type of node. A top level 1602 contains clinical-action nodes 1604-1606. Details about the information stored within a clinical-action node are discussed below. In general, clinical-action nodes store various types of clinically useful information related to the various types of biological characterizations, such as different gene variants for genes within the human genome. This clinically useful information may include, as one example, information about the effectiveness, metabolism, dosing, and adverse effects of particular pharmaceuticals in individuals having particular gene variants. Other types of clinically useful information represented by clinical-action nodes include information that supports, argues against, and clarifies various types of conditions, symptoms, and diagnoses in patients with particular types of gene variants, information concerning risks for various types of pathologies and conditions associated with particular gene variants and/or combinations of gene variants, information about the generational transmissivity of particular genetic conditions, and other such types of information.

A second level 1610 within the network-like clinical-knowledge data structure includes biological-element nodes, each representing a unit of biological information, such as a gene, protein, particular bacterial or eukaryotic member organism of the intestinal flora, and many other such types of biological elements. A third level 1612 of the network-like clinical-knowledge data structure includes variant nodes, each of which represents a different observed variant in a particular type of biological element. For example, for genomic biological elements which describe genes and other portions of chromosomal DNA, a variant may describe an SNP, insertion, deletion, or other variation in the sequence of a gene or other information-containing region of the chromosomal DNA, as discussed above with reference to FIG. 14B. In FIG. 16A, arrows, such as arrow 1614, represent links between nodes of the network-like data structure. Thus, clinical-action nodes, such as clinical-action node 1604, may refer to one or more biological elements. Clinical-action node 1604, for example, references biological elements 1616, 1618, and another biological element not shown in FIG. 16A but referenced by link 1620. In addition, the biological elements generally include reverse links to the clinical-action nodes that link to them, such as reverse link 1622 corresponding to link 1614. These reverse links allow the network-like data structure to be traversed from second-layer biological-element nodes to clinical-action nodes in addition to being traversed from clinical-action nodes to biological-element nodes. Similarly, biological-element nodes may be linked to one or more variant nodes, and forward links from biological-element nodes to variant nodes may be paired with reverse links from the variant nodes to the biological-element nodes. As further discussed below, while the network-like data structure that stores clinical knowledge is referred to as a "data structure," in practical implementations, this data structure is actually contained within large files and file caches within data-storage facilities of the cloud-like medical-information system, with particular nodes and links instantiated as objects copied to memories within servers in order to carry out various computational activities. The clinical-knowledge database is, in most practical implementations, an enormous collection of mass-storage-resident clinical-action nodes, biological-element nodes, and variant nodes along with the many different associated links. In many cases, the nodes of the clinical-knowledge data structure are not fully interconnected, but instead comprise a large number of tree-like interconnected data structures, each having a clinical-action node as a root node. The network-like clinical-knowledge data structure thus may not be a fully connected, but instead may be a forest-like aggregation of multiple tree-like interconnected data structures, or fully-connected partitions or subsets.

FIG. 16B illustrates a third dimension of the network-like clinical-knowledge data structure. In FIG. 16B, the shaded nodes, such as node 1630, represent a portion of the network-like clinical-knowledge data structure shown in FIG. 16A. The network-like clinical-knowledge data structure is logically a two-dimensional data structure that can be depicted as being coincident with a single Euclidean plane. In FIG. 16B, this plane is described by Cartesian x and y axes 1632 and 1634. However, FIG. 16B also shows a third dimension, represented by the Cartesian z axis 1636. This third dimension represents possible alternative clinical-knowledge network-like data structures formed by addition, deletion, or substitution of nodes, links, and subtrees of the z=0, or reference, clinical-knowledge data structure, shown shaded in FIG. 6B, to form a series of alternative clinical-knowledge data structures, or clinical-knowledge-data-structure sets. In FIG. 16B, the increments 1638-1642 along the z axis indicate that, in addition to the reference clinical-knowledge database represented by z=0 1638, there are four additional alternative clinical-knowledge data structures formed by, in the case shown in FIG. 16B, replacement of various nodes with alternative nodes. In FIG. 16B, it is assumed that, unless a replacement node is explicitly shown for an alternative plane or clinical-knowledge data structure, the alternative clinical-knowledge data structures contain the same nodes and links as contained in the reference clinical-knowledge data structure, indicated by shading in FIG. 16B.

This third dimension of the clinical-knowledge data structure allows a reference clinical-knowledge data structure to be modified by various medical-service-providing organizations and research organizations that use the cloud-like medical-information service. As one example, a medical-service-providing organization may develop an alternative clinical-knowledge-data-structure set from the reference clinical-knowledge data structure provided as a default clinical-knowledge data structure by the medical-information service. This alternative clinical-knowledge-data-structure set may represent a reference clinical-knowledge data structure within the medical-service-providing organization. Individual practitioners within the medical-service-providing organization may, in turn, develop their own personal alternative clinical-knowledge-data-structure sets from the medical-service-providing-organization reference clinical-knowledge data structure. In the majority of cases, the alternative clinical-knowledge data structures generally inherit most of the nodes and links from the reference clinical-knowledge data structure provided as a default by the medical-information system, since the reference clinical-knowledge data structure generally contains a vast amount of carefully curated and annotated medical information obtained from thousands, tens of thousands, hundreds of thousands, or more information sources.

Figure 17:
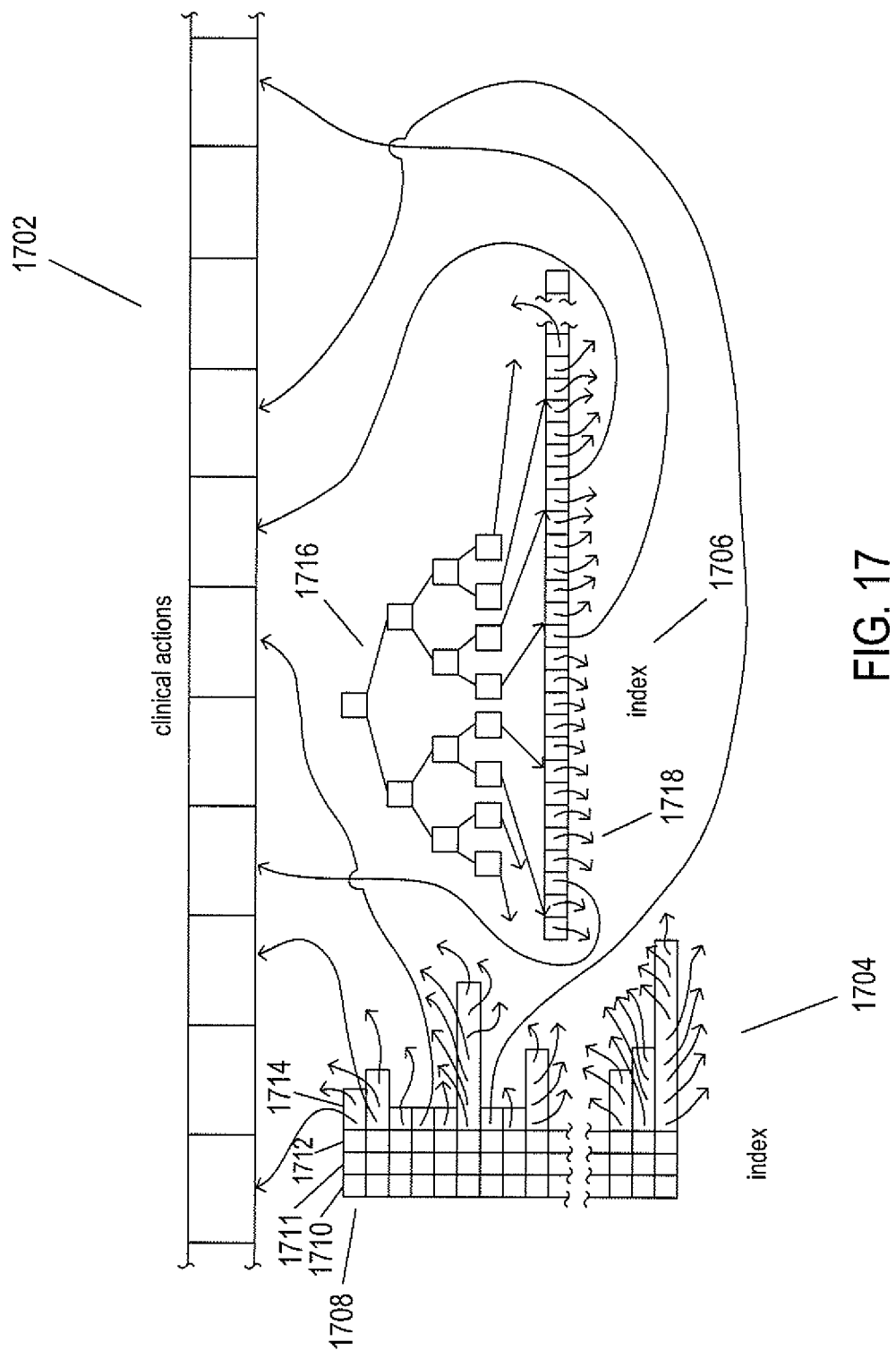
FIG. 17 illustrates an additional feature of the clinical-knowledge data structure.

FIG. 17 illustrates an additional feature of the clinical-knowledge data structure. As shown in FIG. 17, and as mentioned above, clinical-action nodes are stored, in many implementations, as records within one or more very large files that are, in turn, stored on mass-storage devices and caches within the cloud-like medical-information service. In FIG. 17, a portion of a logical file containing records corresponding to clinical-action nodes 1702 is shown at the top of the figure. The clinical-action nodes are directly accessible by file-based record, segment, or block addresses. The clinical-action nodes are also accessible by a variety of different indexes, two of which 1704 and 1706 are shown in FIG. 17. Index 1704 is a compound index, each entry of which, such as the first entry 1708, includes three values 1710-1712 for three different fields within clinical-action nodes and a list of pointers 1714 to clinical-action nodes that have those three values for the three fields. Of course, field values may be specified as discrete values, open-ended value ranges, or closed value ranges. Index 1706 employs a binary tree 1716 of values that allow for identifying one or more references, in an array of references 1718, to clinical-action nodes having a field with a value within a range of one or more values referenced from the binary tree. There are many different types of indexes and indexing methods that can be employed for indexing clinical-action nodes, biological-element nodes, and variant nodes in order to facilitate searching the clinical-knowledge data structure for particular nodes, subtrees, and network-like subsets of the clinical-knowledge data structure.

Figure 18:
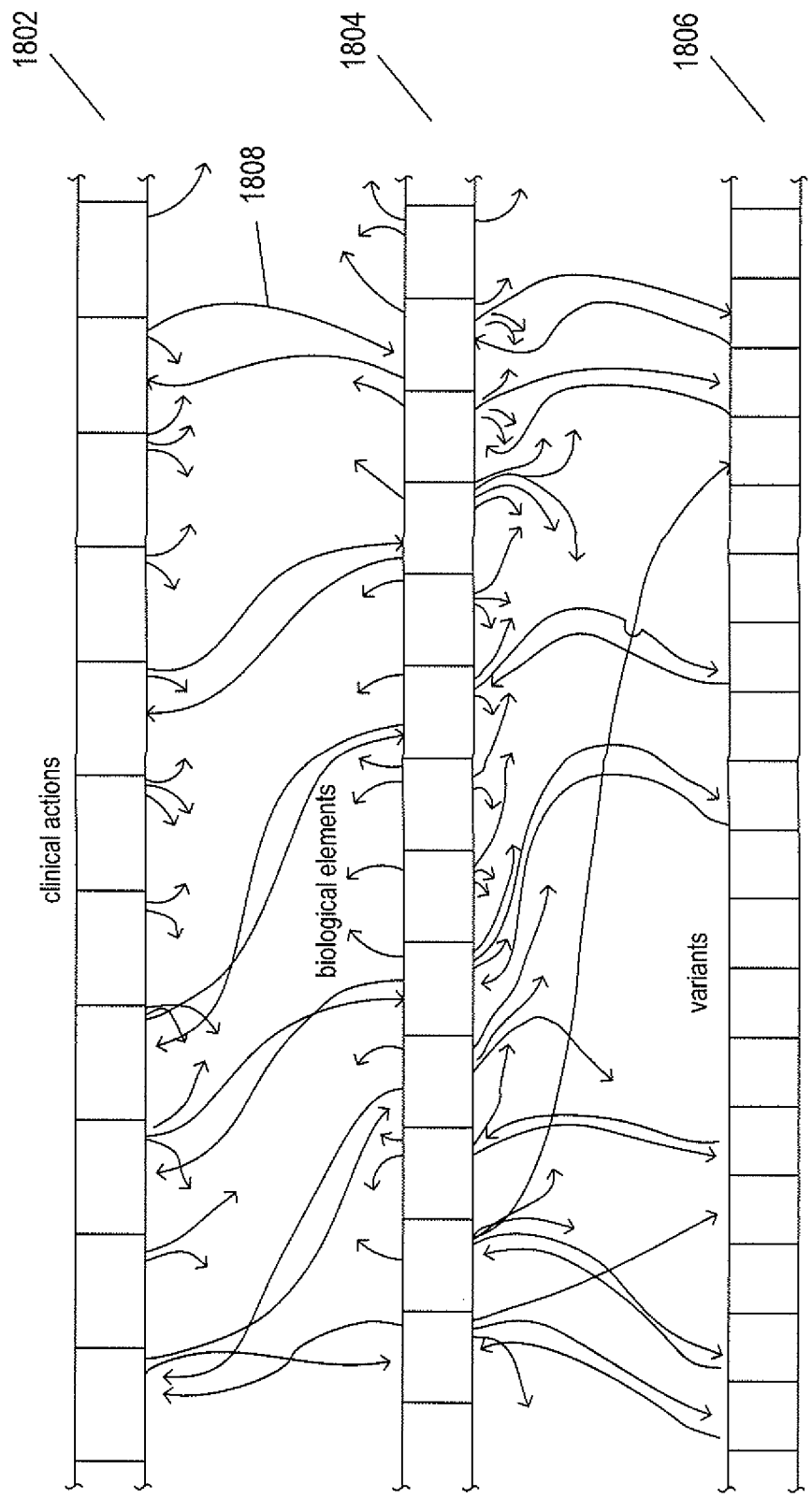
FIG. 18 illustrates the logical storage of clinical-knowledge data structure within data-storage facilities of the cloud-like medical-information service.

FIG. 18 illustrates the logical storage of clinical-knowledge data structure within data-storage facilities of the cloud-like medical-information service. As mentioned above, clinical-action nodes, biological-element nodes, and variant nodes are generally stored as records within one or more files that are maintained within the data-storage facilities. As shown in FIG. 18, one logical file 1802 stores clinical-action nodes, a second logical file 1804 stores biological-element nodes, and a third file 1806 stores variant nodes. In alternative implementations, each of the logical files 1802, 1804, and 1806 may, in fact, comprise multiple mass-storage-device files or even entire virtual address spaces provided by various types of mass-storage systems. The many different links that link the nodes together into a network-like data structure are presented in FIG. 18 by curved arrows, such as curved arrow 1808, are stored in variably sized array fields or other substructures within the nodes. There are many alternative ways for storing large network-like data structures. In one example, such network-like data structures may be stored in relational database tables. Any of many different alternative methods and subsystems can be used for storing the sets of clinical-knowledge data structures within the currently disclosed medical-information service.

Figure 19:
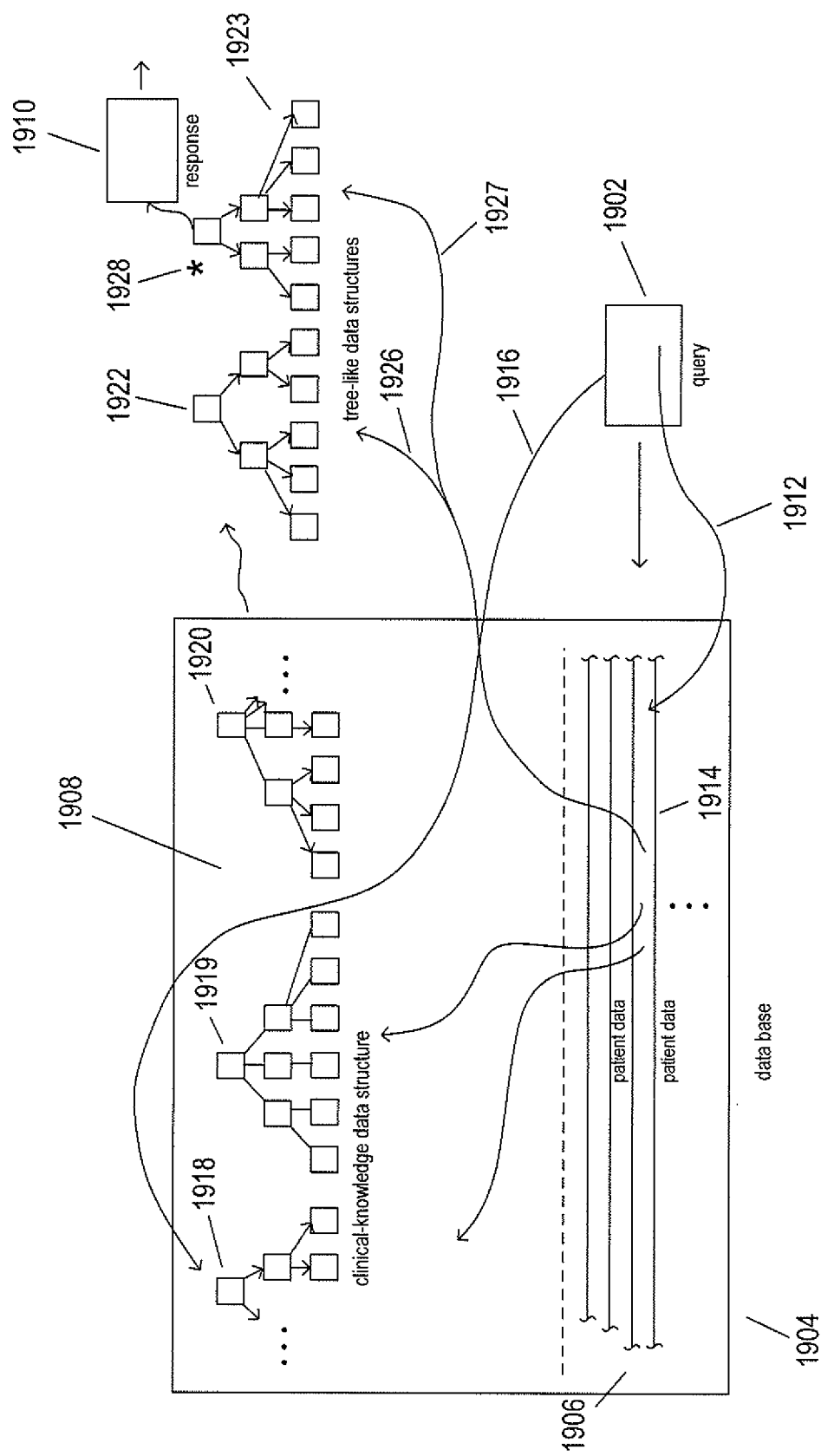
FIG. 19 illustrates use of the clinical-knowledge data structure and patient data by the cloud-like medical-information service in order to process a query received from a user.

FIG. 19 illustrates use of the clinical-knowledge data structure and patient data by the cloud-like medical-information service in order to process a query received from a user. In FIG. 19, the query is represented by rectangle 1902, data stored within the cloud-like medical-information service is represented by larger rectangle 1904, this data including patient data 1906 and the clinical-knowledge data structure 1908. The cloud-like medical-information service generates a response 1910 that is returned to the sender of the query 1902. The query generally contains a JSON encoding of a medical-information query. Queries are often related to information contained in clinical-action nodes, including medication risks and recommendations, information that would support or argue against a diagnosis, information related to risks associated with the biological characterization of a patient, such as a patient's genetic variants, information related to the effectiveness of different types of therapy, carrier status, patient conditions, and other such types of information. A response 1910 is also JSON-encoded information, generally extracted from one or more clinical-action nodes.

In general, the query identifies a particular patient, with this identification allowing for selection, represented by arrow 1912, of the patient data, represented by line segment 1914, for a particular patient. Patient data may be, in the current example, a list of gene variants found in the patient's genome but, as discussed above, may include many different types of information, including information about expressed proteins, the patient's biome, characterizations of other types of biomolecules found in the patient, and many additional types of information. In certain implementations, intermediate files may be created and maintained to store portions of patient data for a particular patient of greatest interest for processing queries during particular time intervals or for processing particular types of queries, and one or more of the intermediate files may therefore be selected, rather than the entire set of data stored for the patient. Information within the query may also indicate one or more clinical-action nodes, as represented by arrow 1916, for selection as candidate clinical-action nodes for query processing. The selected clinical-action nodes may then be extracted along with the biological elements and variants that they directly and indirectly reference as subtrees, such as subtrees 1918-1920. The query may also indicate which of multiple alternative clinical-knowledge data structures from which to gather information for query processing, as discussed above with reference to FIG. 16B. Patient data 1914 selected by information contained in the query may then be used to identify which of the selected subtrees may be pertinent to query processing for the particular patient identified in the query. It should be noted that the cloud-like medical-information service may use various different types of information contained in a query and stored within the cloud-like medical-information service to determine the identity of a patient, and does not require a unique patient identifier be supplied in a query in many implementations, although it may use the unique patient identifier if supplied. As one example, those subtrees that include variant leaf nodes, at least one of which matches a variant contained in the patient data, may be selected as candidate subtrees 1922 and 1923 for query processing. In this example, a subtree lacking a leaf node that matches a genomic variant identified for the patient cannot evaluate to being relevant to the patient, since the variant leaf nodes of the subtree identify those gene variants that contribute to the clinical action represented by the root of the subtree. Then, as represented by arrows 1926-1927, the patient data is again used to evaluate the candidate subtrees 1922 and 1923 to determine those candidate subtrees that represent medical information relevant to the particular patient identified in the query. In the example of FIG. 19, star 1928 represents the fact that candidate subtree 1923 evaluated to being relevant for the patient identified in the query. Finally, information is extracted from those clinical-action nodes that are roots of candidate subtrees that evaluate to relevance and is then included in the response 1910 returned to the user.

The illustration in FIG. 19 provides a general overview of the use of the clinical-knowledge data structure and query processing. There are, however, many different alternative ways in which the clinical-knowledge data structure may be accessed and utilized for processing of different types of queries. For example, a very general query may be directed to identifying all possible clinical actions that might be relevant to a particular patient, in which case patient data is used to select all possible candidate subtrees and to then evaluate the relevance of all of the candidate possible subtrees, without need for selection of particular clinical-action nodes. In many cases, processing may begin by selecting candidate biological elements and then traversing both upward and downward from the biological elements to identify candidate subtrees. Other types of queries may be processed primarily using one or more indexes that index clinical actions and biological elements, discussed above with reference to FIG. 17.

Figure 20:
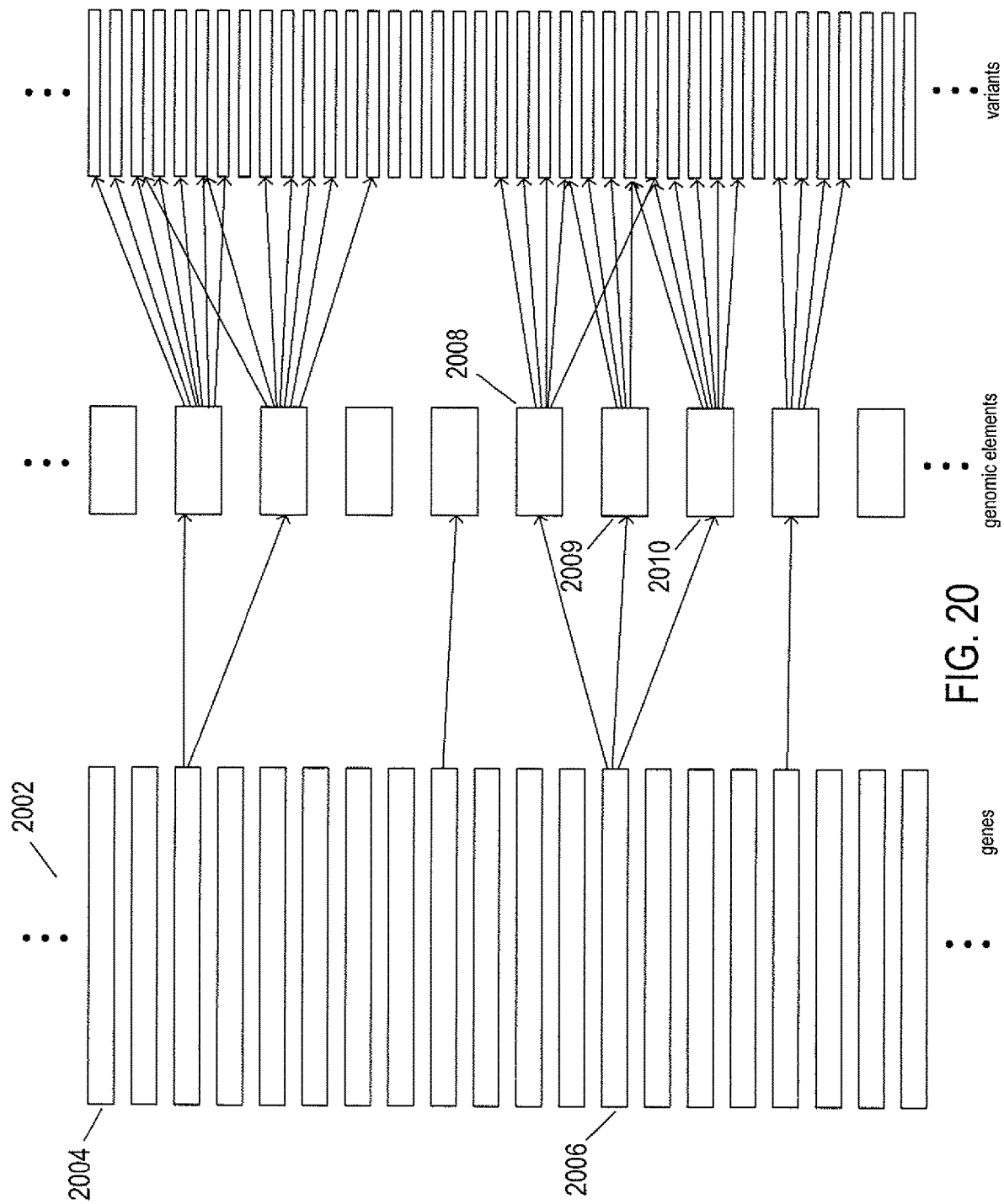
FIG. 20 illustrates the relationship between genes, genomic biological elements, and genomic variants.

FIG. 20 illustrates the relationship between genes, genomic biological elements, and genomic variants. In FIG. 20, each rectangle in the left-hand column 2002, such as rectangle 2004, represents a different gene in the human genome. Each gene may be represented by zero, one, or more genomic biological elements in the clinical-knowledge data structure. For example, gene 2006 is represented by the three genomic biological elements 2008-2010. Each genomic biological element may represent a different constellation of variants within the gene that produces a well-known phenotype associated with the gene. Thus, the relationship between an individual gene and genomic biological elements in the clinical-knowledge data structure is, in general, one-to-many. Consequently, the relationship between genomic biological elements and variants in the clinical-knowledge data structure is many-to-many. Of course, it is possible that, for a particular gene, only a single SNP is known, in which case the gene would be represented in the clinical-knowledge data structure by a single genomic biological element and a single variant. However, in general, each gene may correspond to multiple genomic biological elements which, in turn, may reference multiple variants, with a particular variant referenced by multiple genomic biological elements.

Figure 21:
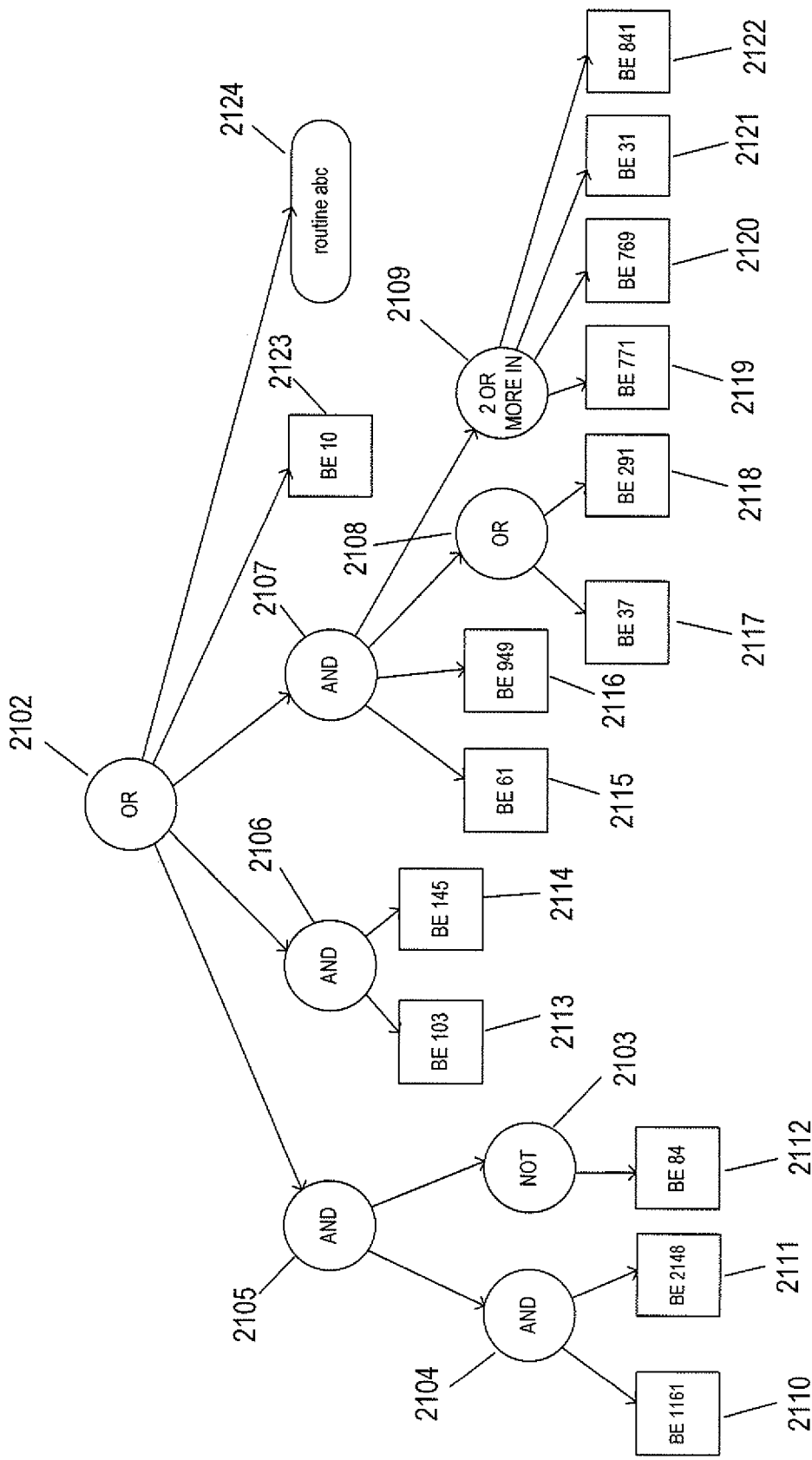
FIG. 21 illustrates a Boolean expression that, in certain implementations, is encoded into one or more fields of a clinical-action node and that is used to evaluate whether or not the clinical action is relevant to a particular patient.

FIG. 21 illustrates a Boolean expression that, in certain implementations, is encoded into one or more fields of a clinical-action node and that is used to evaluate whether or not the clinical action is relevant to a particular patient. The example Boolean expression, illustrated in FIG. 21, is shown as a tree, with operator nodes as the root node and intermediate nodes, represented by circles or disks, and biological elements, represented by squares, and routine calls, represented by sausage-shaped objects, as leaf nodes. In the particular Boolean expression shown in FIG. 21, the root node 2102 represents the Boolean OR operation, intermediate nodes 2104-2107 represent Boolean AND operations, intermediate node 2108 represents the Boolean OR operation, and intermediate node 2109 represents a set-like operation that evaluates to TRUE when two or more of the biological-element leaf nodes of the set-like operation 2109 evaluate to TRUE. Leaf nodes 2110-2123 represent biological-element nodes which may evaluate to TRUE or FALSE and leaf node 2124 is a call to a routine "ABC" that returns either Boolean TRUE or Boolean FALSE. A biological element leaf node evaluates to TRUE when a Boolean expression contained in the biological element evaluates to TRUE and otherwise evaluates to FALSE. Boolean expressions contained in biological elements are discussed below. However, to summarize, a biological element evaluates to TRUE when one or more variant nodes to which the biological element is linked correspond to variants found in the data for a particular patient. In the current example, the clinical-action node containing the Boolean expression illustrated in FIG. 21 may represent some type of syndrome or pathology which can arise when biological elements 2110 and 2111 evaluate to TRUE for the patient, but a biological element 84 evaluates to FALSE, when both biological elements 2113 and 2114 evaluate to TRUE for the patient, when biological elements 2115, 2116, one or both of biological elements 2117 and 2118, and two or more of biological elements 2119-2122, evaluate to TRUE for the patient, when biological element 2123 evaluates to TRUE for the patient, or when routine "ABE" returns a value of TRUE.

Figure 22:
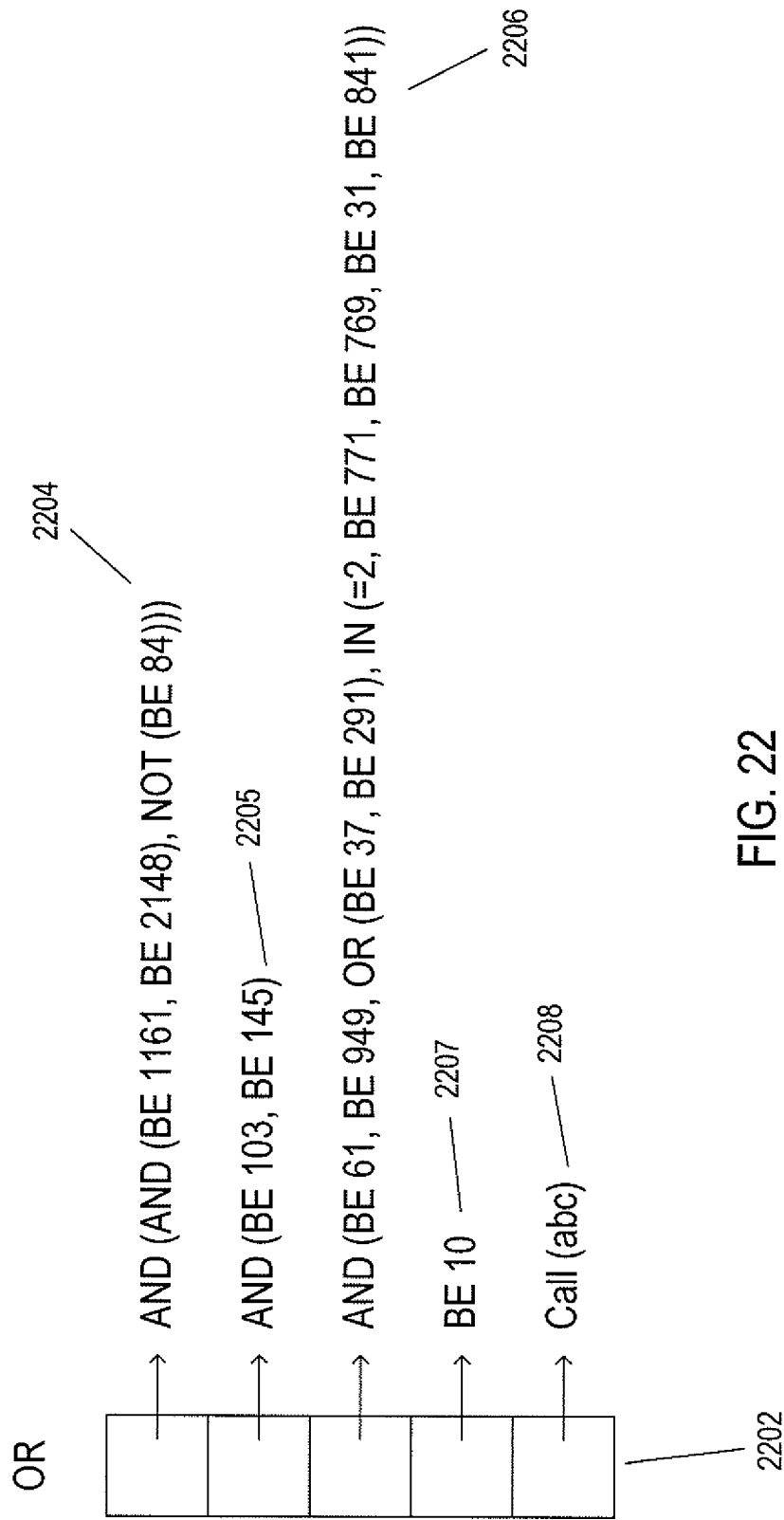
FIG. 22 shows an alternative representation of the Boolean expression shown in FIG. 21.

FIG. 22 shows an alternative representation of the Boolean expression shown in FIG. 21. In this representation, the OR root node (2102 in FIG. 21) is represented by the vertical array 2202, the elements of which reference prefix expressions 2204-2208 that represent subtrees in FIG. 21 rooted by nodes 2105-2107, 2123, and 2124, respectively.

It should be noted that there are a variety of different ways in which to encode logic equivalent to the above-described Boolean expressions. For example, the logic can be encoded in a combination of data substructures and routines that process the data substructures to produce results equivalent to results produced by evaluating Boolean expressions. For example, a Boolean expression comprising a number of references to biological elements with interleaved OR operators may be alternatively represents by an array containing references to the biological elements as a routine or instructions that sequentially evaluate the referenced biological elements until a biological element evaluates to TRUE, in which the routine returns TRUE, or until there are no further references to biological elements in the array, in which the routine returns FALSE. In other implementations, evaluations of logic or expressions may produce values other than Boolean values.

Figure 23:
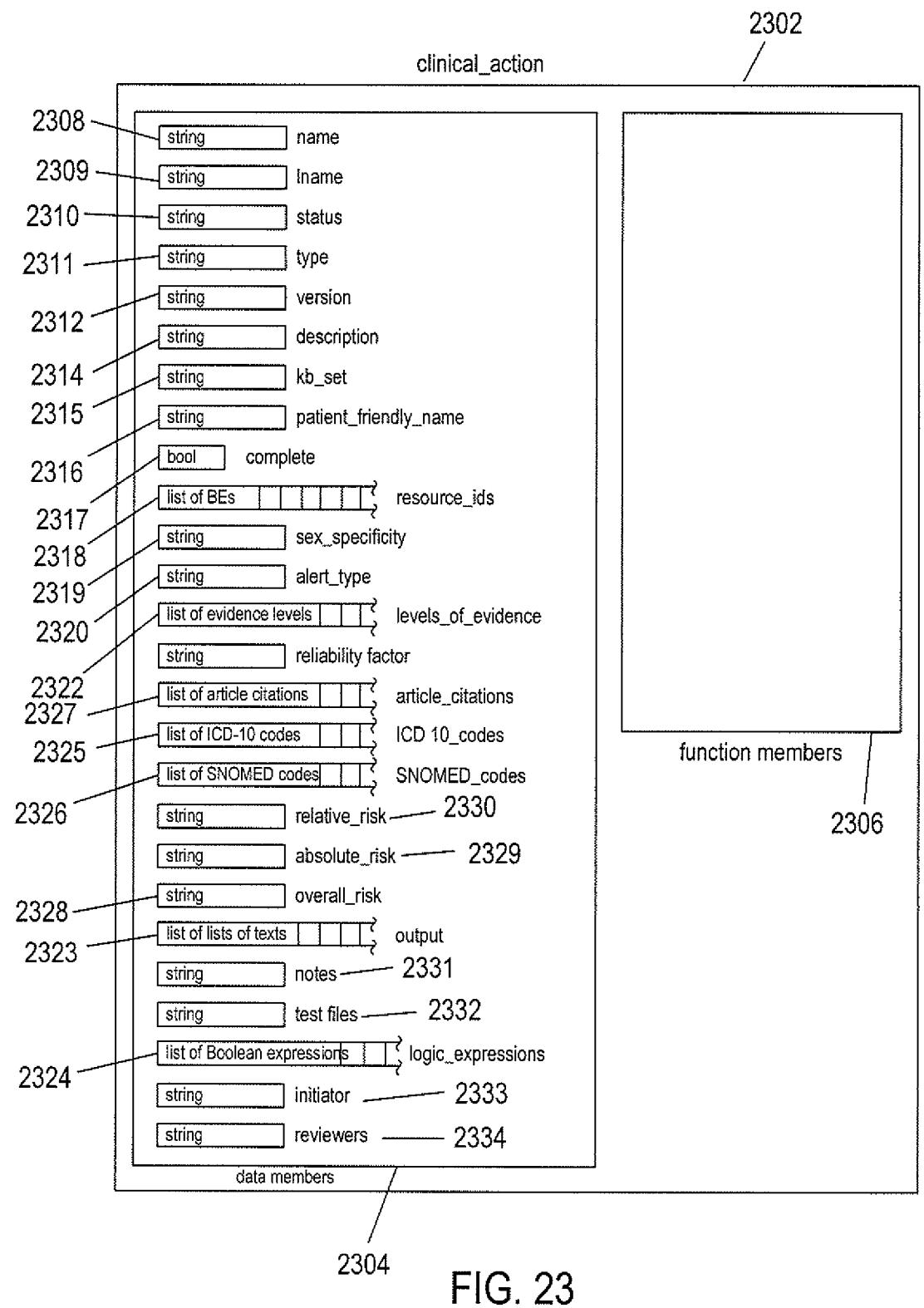
FIG. 23 illustrates a clinical-action node in one implementation of the cloud-like medical-information service.

FIG. 23 illustrates a clinical-action node in one implementation of the cloud-like medical-information service. The clinical-action node is, in this implementation, instantiated as an object 2302 when loaded into a server memory for query processing. As an object, the clinical-action node includes both data members 2304 and function members 2306. The function members primarily consist of "get" and "set" functions that retrieve values stored in data members and write values to data members, respectively. The data member "name" 2308 stores the name for the clinical action and the data member "lname" 2309 stores a lower-case version of the clinical-action-node name. The data member "status" 2310 stores a status for the clinical-action node. The status may indicate any of a number of possible different states for the node, including various states concerning current editing of the node by a scientist or researcher, a state in which the node is under development by programmers or developers, and other such states. The data member "type" 2311 indicates the category of clinical-action nodes to which the clinical-action node belongs. As discussed above, there may be many different possible clinical-action-node categories, including medication-related clinical-action nodes, diagnosis-related clinical-action nodes, risk-related clinical-action nodes, and other such categories of clinical-action nodes. The data member "version" 2312 indicates the version of the node with respect to ongoing creation and maintenance of the clinical-knowledge data structure to which the node belongs. The data member "description" 2314 includes a brief description of the subject matter to which the clinical-action node pertains or which the clinical-action node represents. The data member "kb_set" 2315 indicates to which of various alternative clinical-knowledge-data-structure sets the node belongs, discussed above with reference to FIG. 16B. The data member "patient_friendly_name" 2316 stores an alternative name for the node that may be more understandable or acceptable to a patient reviewing the subject matter of the node in a report prepared for the patient. The data member "complete" 2317 indicates whether or not the clinical-action node contains sufficient information to be considered complete, for query-processing purposes. The data member "resource_ids" 2318 contains a list of the identifiers or addresses for biological elements referenced by the clinical-action node and therefore included in the logic expressions representing subtrees of a general Boolean expression for the clinical-action node, as discussed above with reference to FIGS. 21 and 22. This data member may also be considered to contain the links that link the clinical-action node to biological elements. The data member "sex_specificity" 2319 indicates, for example, by the using the strings "m," "f," and "none," any sex specificity associated with the clinical action. The data member "alert_type" 2320 contains information about any alerts associated with the clinical-action node. These alerts may result in displaying information extracted from the clinical-action node in a way that attracts particular attention to the information or may result in display of the information in cases in which, without the alert, the information would not normally be displayed. The data member "levels of evidence" 2322 includes an indication of the authoritative support for each of multiple different output texts, stored in data member "output" 2323, that are selected for return in response messages to users. In one implementation, a level of evidence may assume one of three different levels, such as "low," "medium," and "high." This authoritative support may also be returned to a requestor for display to the requestor. In general, various types of requests may result in different combinations of information extracted from clinical-action-node fields being returned to users, in addition to the text stored in the variable "output," discussed below. In certain implementations, each of the logic expressions representing subtrees of an overall logic expression for the clinical-action node, stored in the data member "logic expressions" 2324, is associated with a fixed number of outputs, one each for various different audiences for the information, including patients, physicians, and researchers. Thus, during evaluation of a subtree rooted by the clinical-action node to determine whether or not the clinical-action node is relevant to a particular patient, the logic expression stored in the data member "logic_expressions" are evaluated one-by-one, in sequential order, until one of the logic expressions evaluates to TRUE. The output and level of evidence corresponding to the first logic expression that evaluates to TRUE are returned in the response message along with any other information requested by the user. Each of the logic expressions may additionally be associated with one or more medical-claim, diagnosis, or procedure codes, such as ICD-10 and SNOMED CT codes, stored in list-of-list data members "ICD_10_codes" and "SNOMED_codes" 2325-2326. Each of the logic expressions may additionally be associated with a list of article citations, stored in the list-of-lists data member "article_citations" 2327. The data member "overall_risk" 2328 stores an indication of the population risk for the medical condition represented by the clinical-action node, the data member "absolute_risk" 2329 stores an indication of a particular patient's risk for the medical condition, and the data member "relative_risk" 2330 stores an indication of the relative risk for a particular patient. In certain implementations, the data members "overall_risk," "absolute_risk," and "relative_risk" may be lists that store risk indications associated with each of the logic expressions stored in data member "logic_expressions" 2324. Data member "notes" 2331 stores various types of notes and annotations that are associated with the clinical-action node by clinicians, researchers, developers, and other such users. Data member "test files" 2332 stores references to various types of testing and simulation routines that can be used to test the contents of the clinical-action node with respect to various types of queries and operations. The data member "initiator" 2333 stores an indication of the developer or scientist who created the clinical-action node and data member "reviewers" 2334 stores a list of the names of those scientists, clinicians, and/or developers who have reviewed the contents of the clinical-action node.

Figure 24:
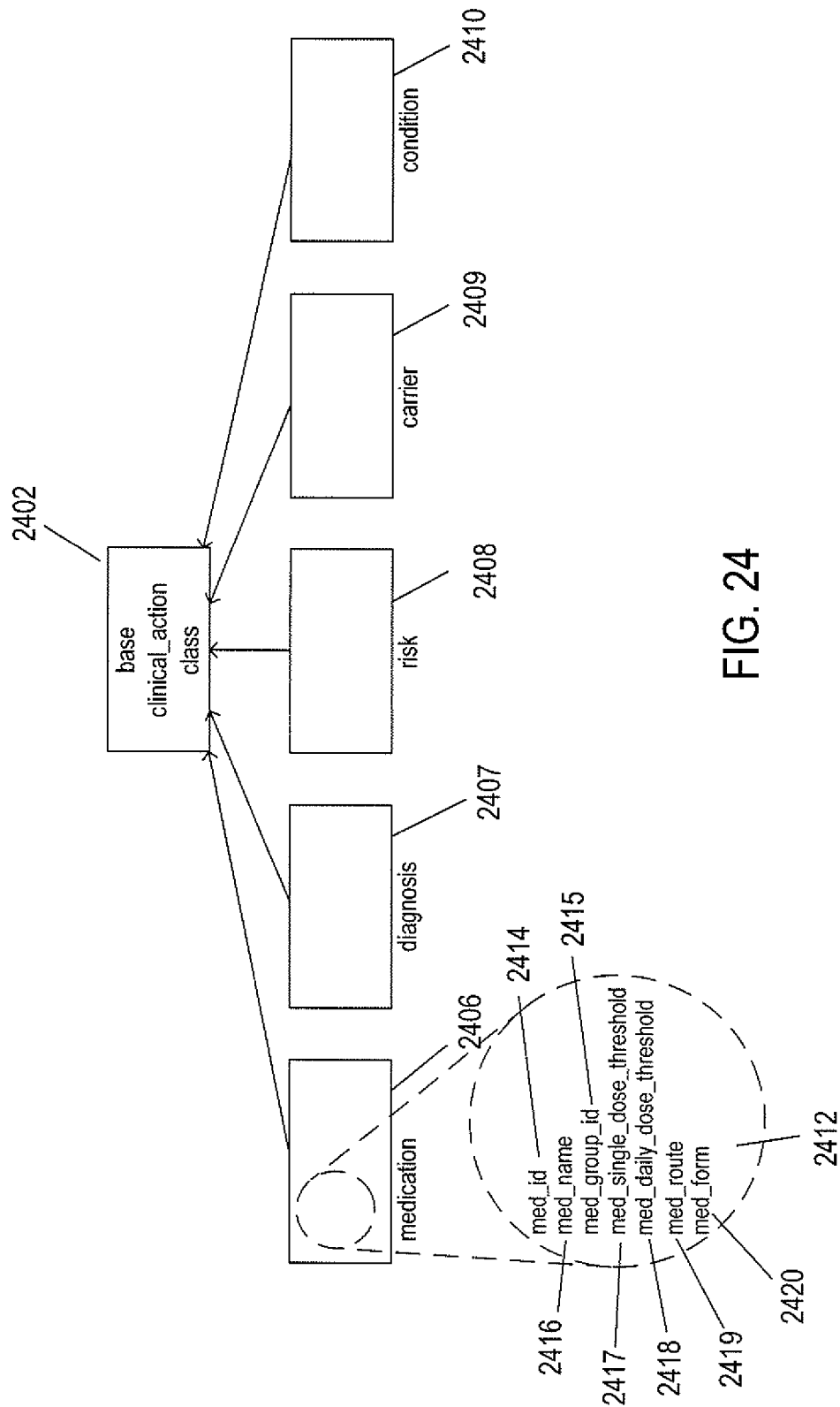
FIG. 24 shows inheritance relationships for clinical-action-node objects.

As mentioned above, a clinical-action node, as well as biological-element and variant nodes, of the clinical-knowledge data structure are instantiated in server memories as objects. FIG. 24 shows inheritance relationships for clinical-action-node objects. In certain implementations, clinical-action-node objects are derived from a base clinical-action-node class 2402. Each derived clinical-action-node class, instantiated as a clinical-action-node object, 2406-2410, represents a different category of clinical-action node. Each of the derived classes may include additional data members and function members. For example, the medication type of clinical-action node 2406 includes the additional data members shown in inset 2412, including identifiers for a particular pharmaceutical 2414 and a family of pharmaceuticals 2415 to which the pharmaceutical belongs, a name for the pharmaceutical 2416, dosage thresholds 2417 and 2418, an indication of the route of delivery of the pharmaceutical 2419, and an indication of the physical form of the pharmaceutical 2420, such as liquid, crystalline, etc.

Figure 25:
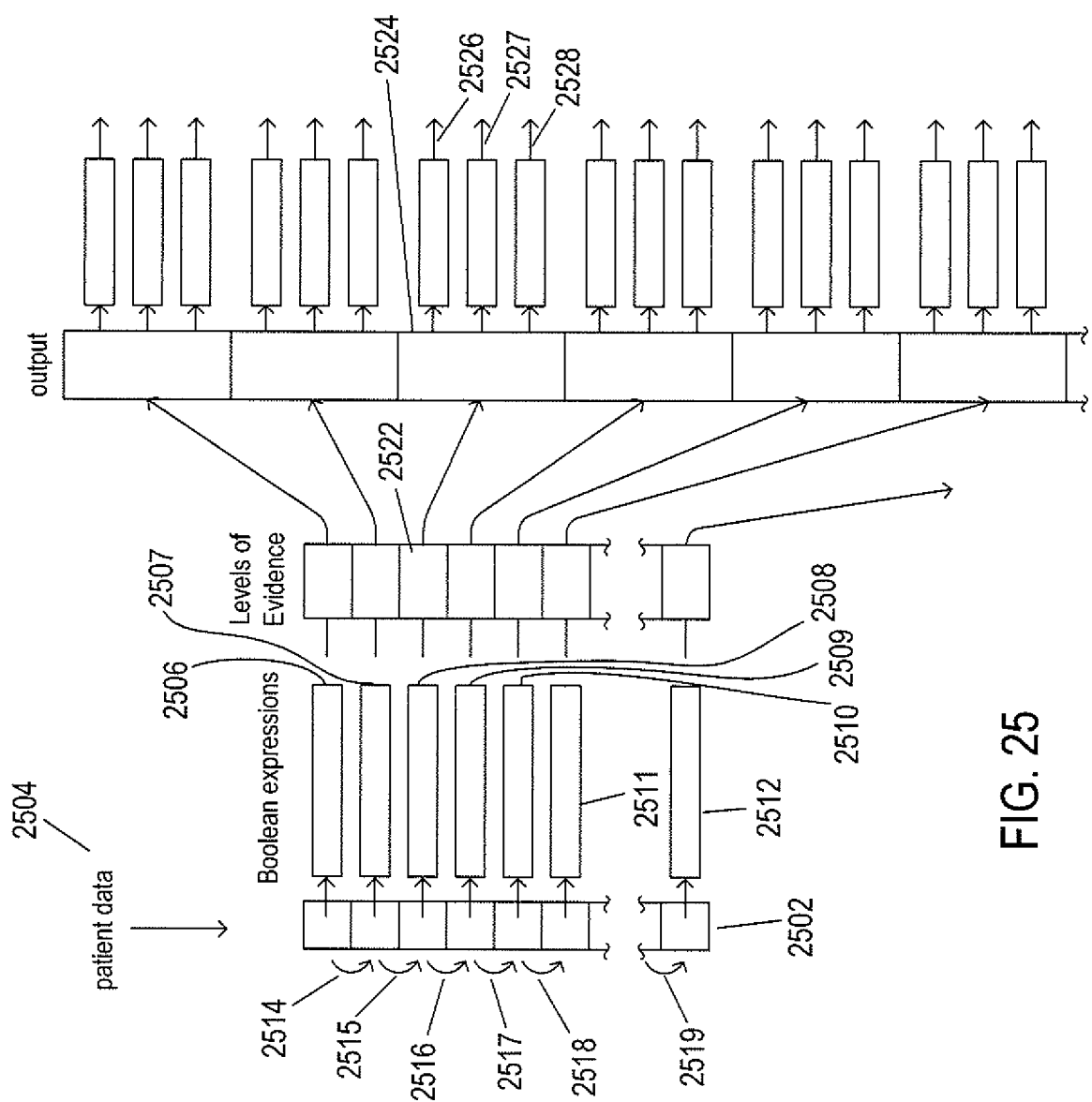
FIG. 25 illustrates the logic of clinical-action-node resolution.

FIG. 25 illustrates the logic of clinical-action-node resolution. In FIG. 25, the column of references to Boolean expressions 2502 is the same column of references to Boolean expressions as shown in column 2202 in FIG. 22. Patient data selected using patient-identification information contained in a query 2504 is used to evaluate each of the Boolean expressions 2506-2512 referenced from a column of Boolean-expression references 2502 in sequence, starting with the first Boolean expression 2506, as represented by curved arrows 2514-2519. The first Boolean expression that evaluates to TRUE, such as, in the current example, Boolean expression 2510, then selects a corresponding level of evidence 2522 and output text 2524. The identity of the recipient of the response selects a particular one of multiple different output texts 2526-2528 that together represent the different possible forms of output text 2524 selected by the first Boolean expression that evaluates to TRUE, in this case Boolean expression 2510. The selected output, level of evidence, and/or other information extracted from the clinical-action node and nodes directly and indirectly referenced by the clinical action node may then be returned to a user. The patient data is used, when a clinical-action node corresponding to genomic information is being evaluated to determine which of the gene variants, referenced through genomic biological elements referenced from the clinical-action node, are present in a patient for which information is being returned, as a result of query processing. The genomic biological elements referenced from the clinical-action node are then evaluated with respect to the referenced variants that are present in the patient, with each genomic biological element evaluating to TRUE or FALSE. These TRUE and FALSE values are then substituted for biological-element leaf nodes in the Boolean expressions in order to evaluate the Boolean expressions.

Certain of the leaf nodes in the Boolean expressions may be function calls, as mentioned with reference to FIG. 21. Routine-call leaf nodes in the Boolean expressions allow for more complex logic to be employed for evaluating clinical-action nodes for relevance to a particular patient than can be expressed using Boolean operators and evaluated biological elements.

Figure 26:
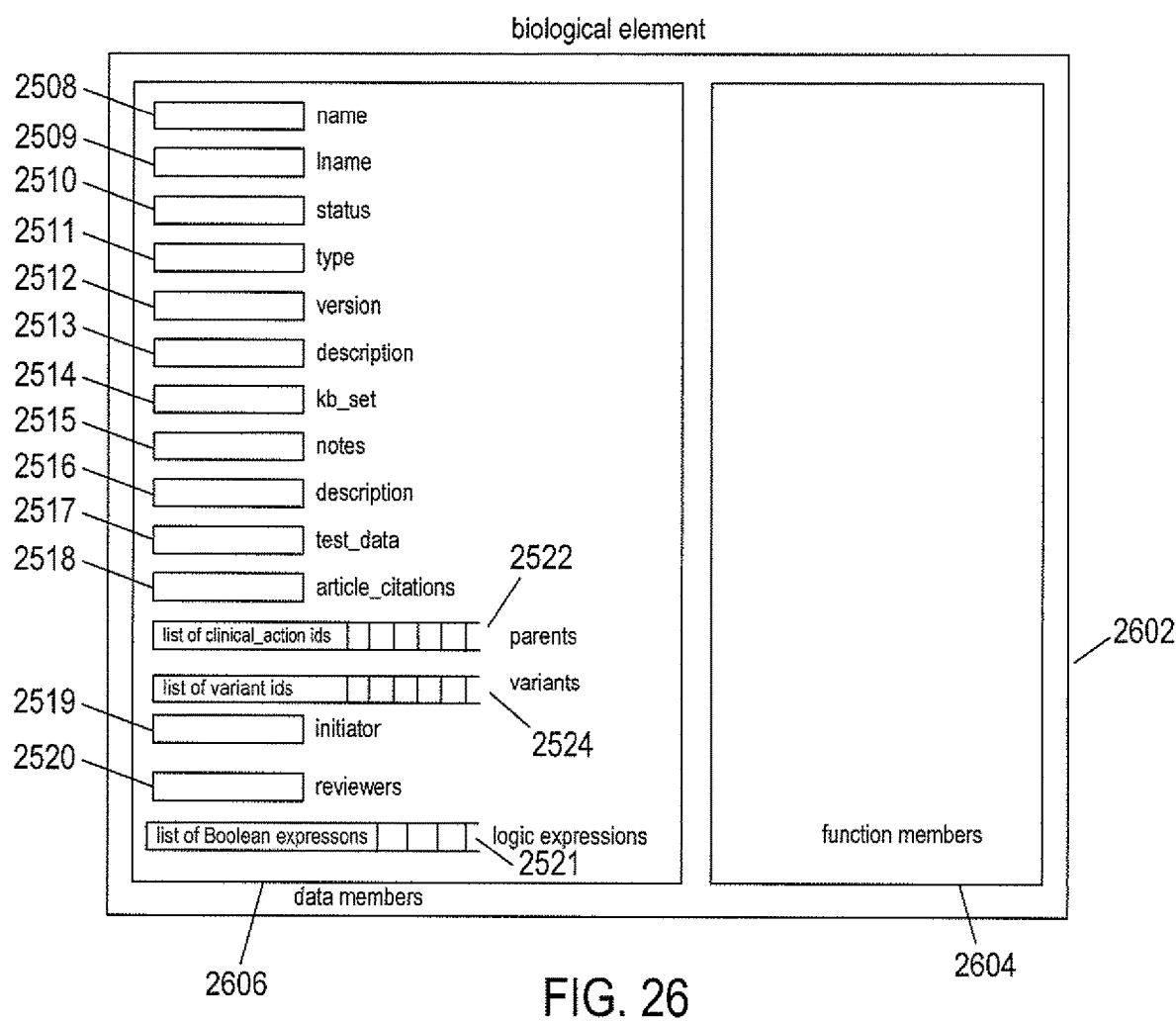
FIG. 26 illustrates, using the same illustration conventions as used in FIG. 23, an instantiated biological-element-node object.

FIG. 26 illustrates, using the same illustration conventions as used in FIG. 23, an instantiated biological-element-node object. As with a clinical-action-node object, shown in FIG. 23, the biological-element-node object 2602 includes both function members 2604 and data members 2606. The function members largely comprise "get" and "set" function members that retrieve values from, and store values into, the data members. The data members "name" 2508, "1name" 2509 "status" 2510, "type" 2511, "version" 2512, "description" 2513, "kb_sets" 2514, "notes" 2515, "description" 2516, "test_data" 2517, "article_citations" 2518, "initiator" 2519, "reviewers" 2520, and "logic_expressions" 2521 all serve equivalent purposes as the identically named data members of the clinical-node object discussed with reference to FIG. 23. Additional data members "parents" 2522 and "variants" 2524 contain references to clinical-action-node objects and to variant-node objects. The references contained in the data member "parents" represent the reverse links that allow second-level-to-first-level traversing of the clinical-knowledge data structure. The references in the data member "variants" represent forward, downward links from the biological-element node to variant nodes.

Figure 27:
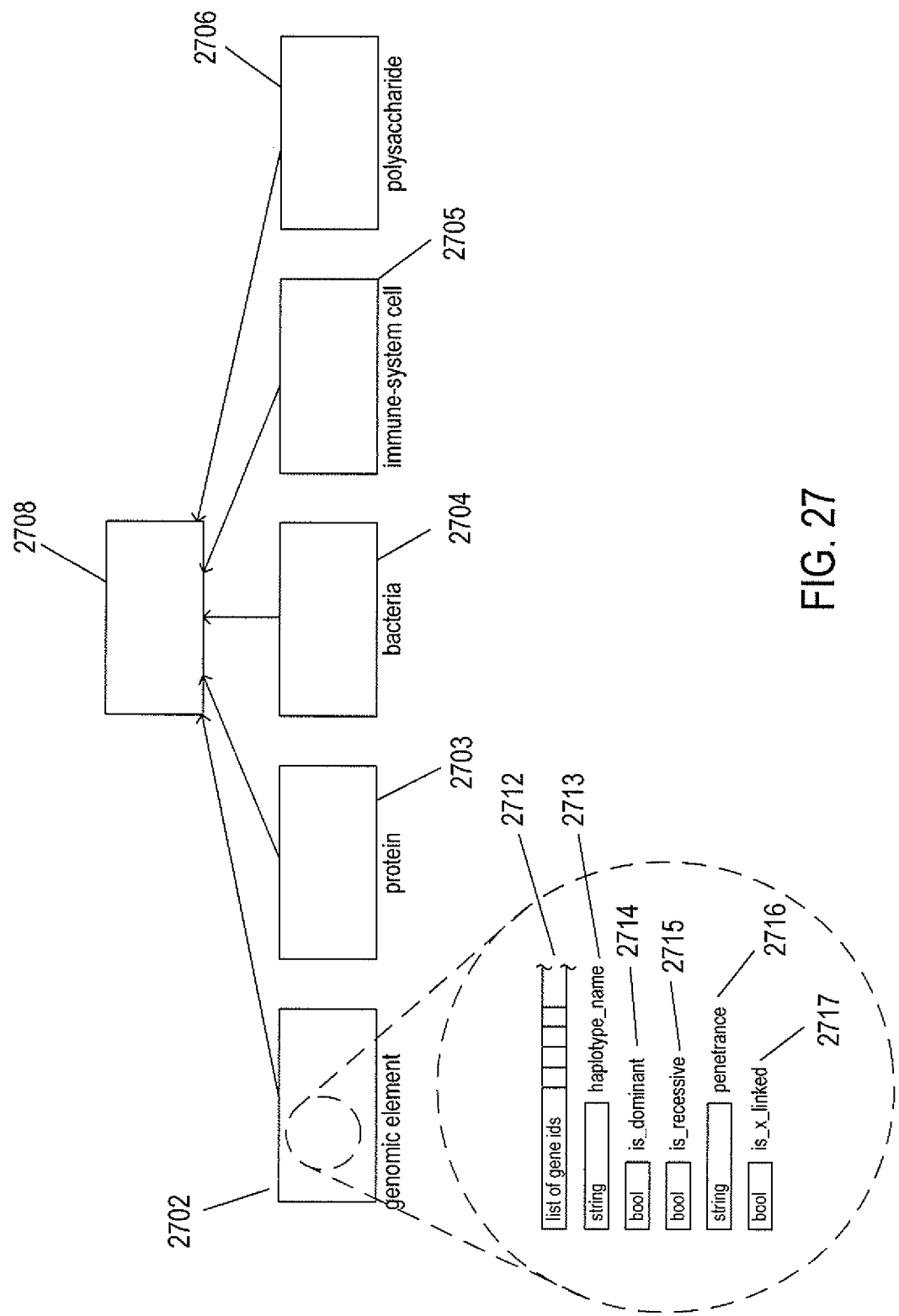
FIG. 27 shows inheritance of different types of biological elements from a base biological-element class.

FIG. 27 shows inheritance of different types of biological elements from a base biological-element class. FIG. 27 uses the same illustration conventions as used in FIG. 24. The various different types of biological elements are represented by classes 2702-2706 derived from the base biological-element-node class 2708. Each derived biological-element-node class may contain additional function members and data members. For example, inset 2710 shows various additional data members contained in a genomic biological-element node. These include a list of unique identifiers for the gene represented by the genomic biological element 2712, an indication of the pattern of variants within the gene represented by the genomic biological element 2713, an indication of whether or not the constellation of variants represented by the genomic biological element is dominant 2714 and a similar indication of whether or not the constellation of variants represented by the genomic biological element is recessive 2715, an indication of the risk of a variant-related syndrome or pathology given the presence of the pattern of variants represented by the genomic biological element in a patient 2716, and an indication of whether the genomic biological element represents an X-chromosome-linked phenomena 2717.

Figure 28A:
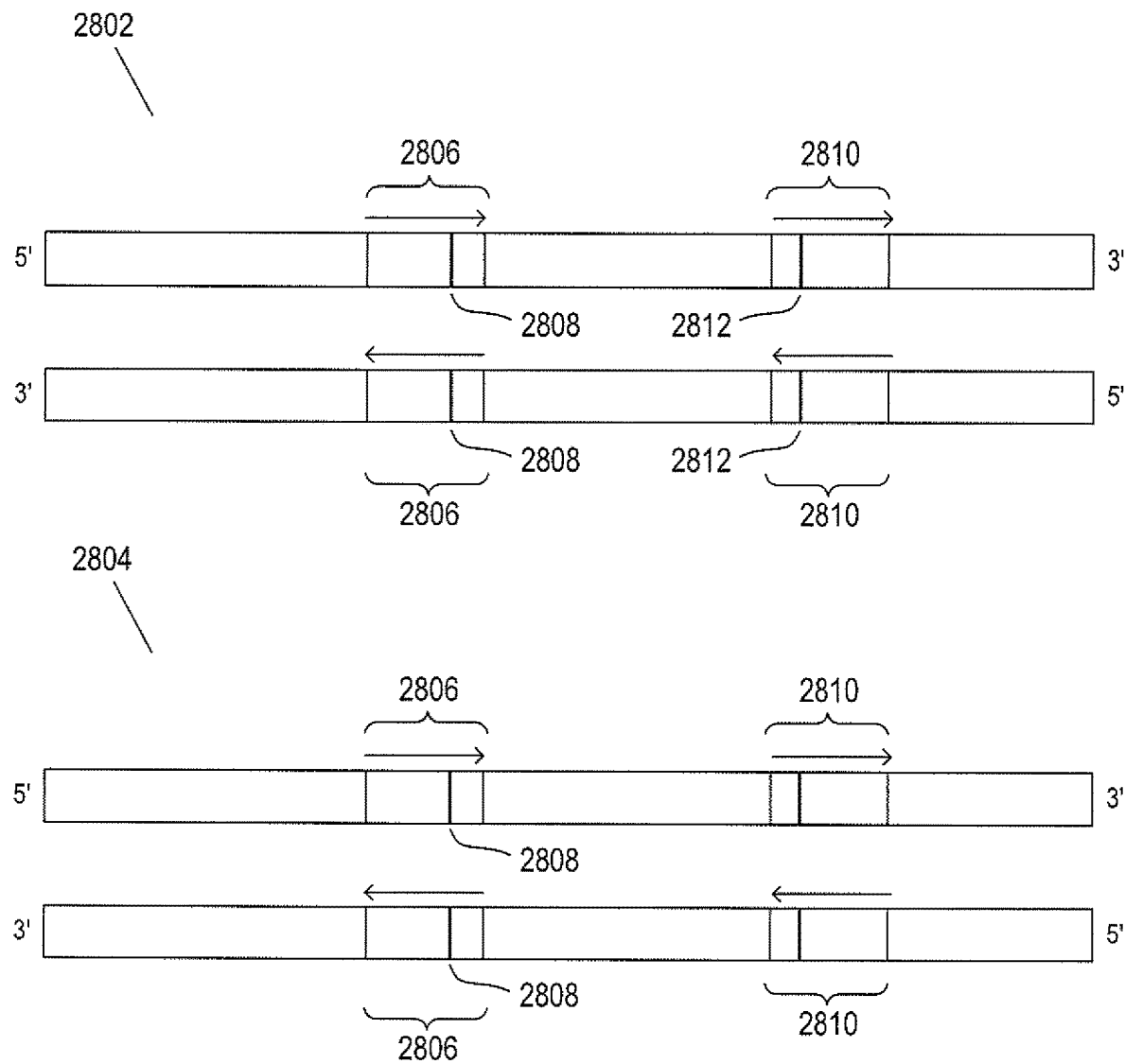
FIG. 28A shows two different genes within a pair of chromosomes.

FIG. 28A shows two different genes within a pair of chromosomes. As discussed above, each chromosome 2802 and 2804 of the chromosome pair includes a double-stranded DNA polymer that encodes genes, regulatory regions, various types of non-coding RNAs, and other information. In FIG. 28A, a first gene 2806 includes a lesion or variant 2808 in both of the paired chromosomes 2802 and 2804. A second gene 2810 includes a lesion or variant 2812 in only the first of the two chromosomes. The first gene is referred to as having a homozygous variant, since the same variant is present on both chromosomes. The second gene 2810 is referred to as having a heterozygous variant since one chromosome includes the variant but the other chromosome does not include the variant. Homozygous variants are generally dominant, in the case that there are only two copies of the gene, one on each chromosome pair, since they affect all of the proteins coded by the gene. Heterozygous variants, by contrast, generally affect only half of the proteins coded by the gene, and may either be dominant or recessive, depending on the biological effect of the variant. Compound heterozygous variants, like homozygous variants, may often be dominant, because a compound heterozygous variant results from two non-wild-type genes at equivalent positions with each chromosome of a chromosome pair.

Figure 28B:
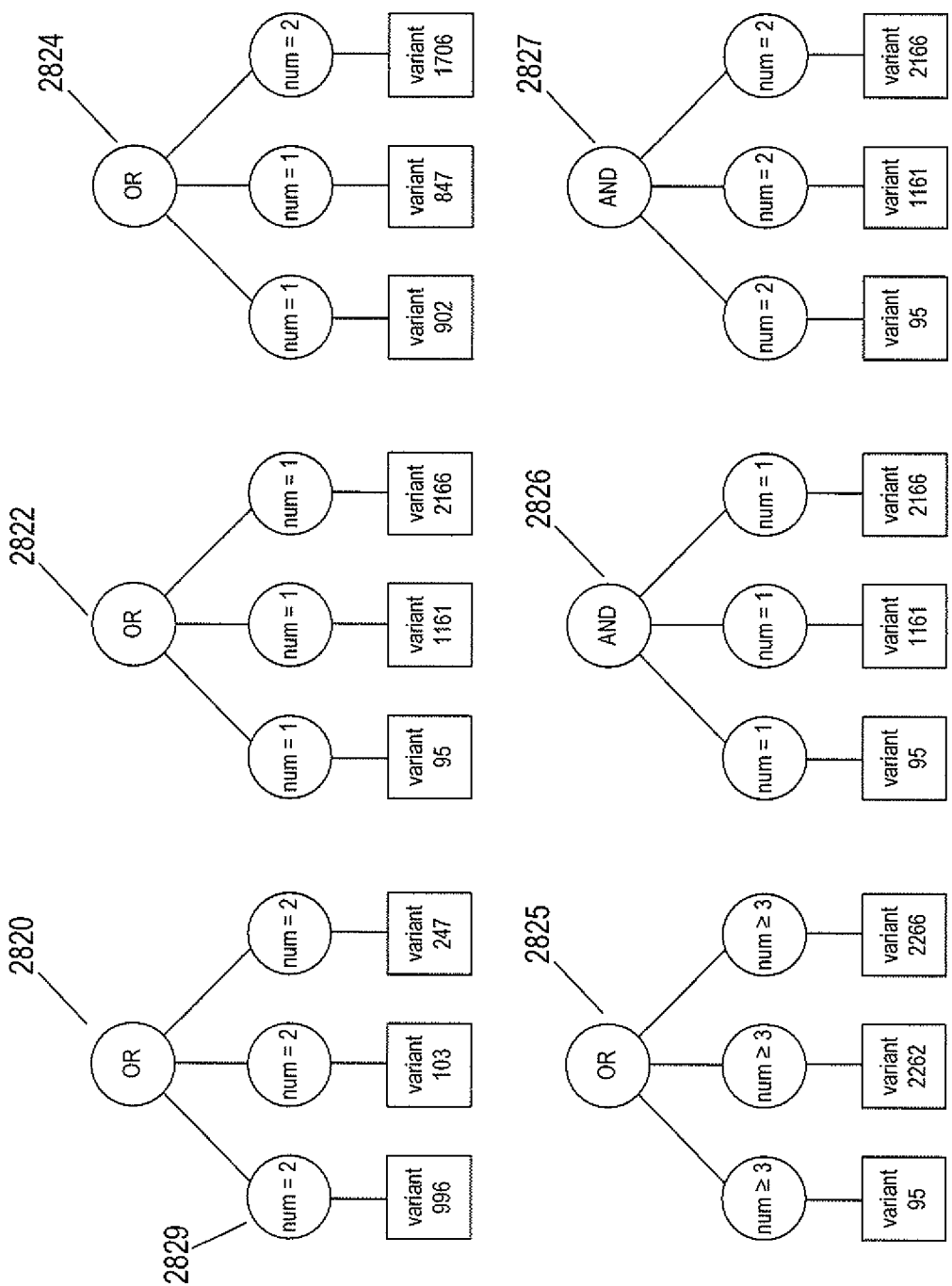
FIG. 28B illustrates the type of logic expressions that can be included in the list of logic expressions contained in a genomic biologic element.

FIG. 28B illustrates the type of logic expressions that can be included in the list of logic expressions contained in the data member "logic_expressions" 2324 that specify the different patterns of variants that need to be present within the gene represented by a genomic biologic element in order for the condition represented by the genomic biological element to occur. In other words, when the expression evaluates to TRUE, then the condition or effect represented by the genomic biological element is present within an individual. As one example, the expression represented by tree 2820 indicates that the condition represented by a genomic biological element that contains this logic expression is present in an individual when that individual is homozygous for any of gene variants 996, 103, and 247, where these numbers are identifiers for the variants. As another example, the logic expression represented by tree 2822 evaluates to true when a patient is heterozygous for any of variants 95, 1161, or 2166. Additional example expressions are represented by trees 2824-2826.

Figure 29:
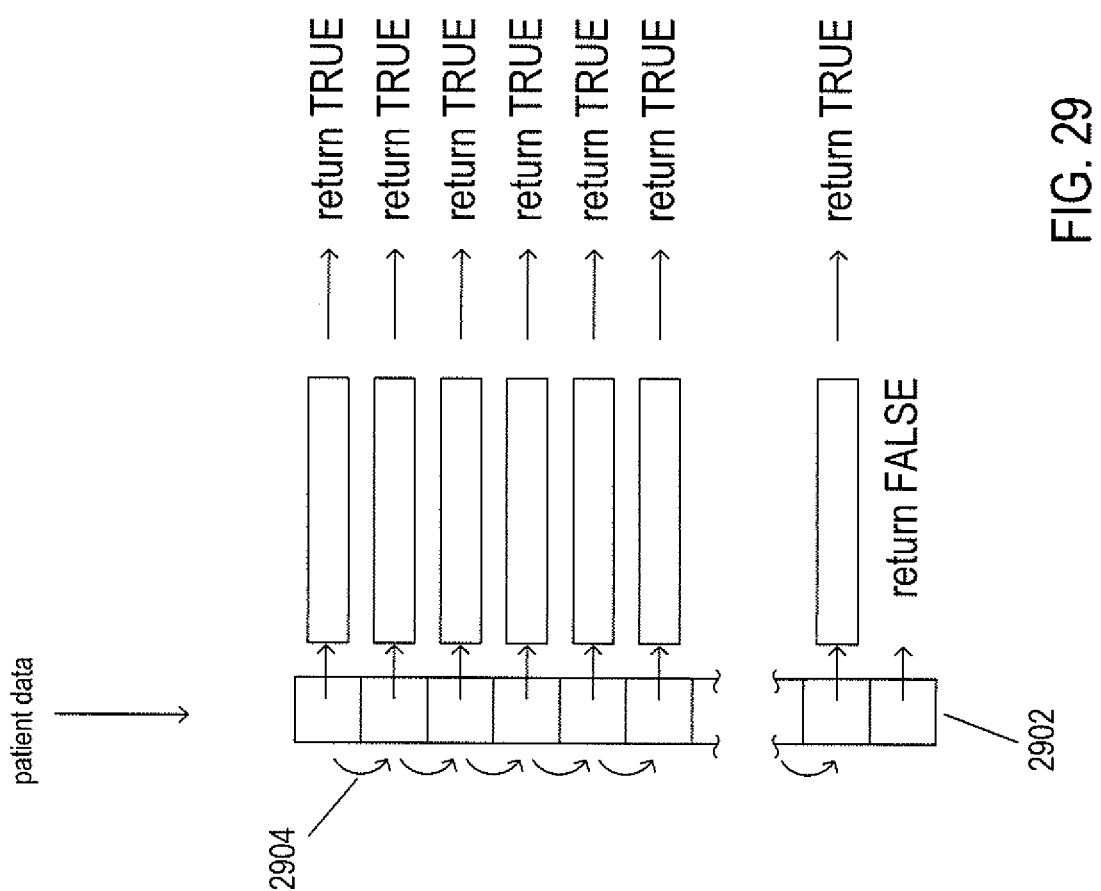
FIG. 29 illustrates, using similar illustration conventions as those used in FIG. 25, evaluation of a genomic biological element.

FIG. 29 illustrates, using similar illustration conventions as those used in FIG. 25, evaluation of a genomic biological element. The column array of references to logic expressions 2902 represents a forest of logic expressions, such as the forest of logic expressions shown in FIG. 28B. Patient data is used to evaluate whether or not a given variant is present in the patient and the number of copies of the variant present in the patient. Thus, the patient data can be used to evaluate each of the first-level copy-number nodes, such as first-level copy-number node 2829 in FIG. 28B, to TRUE or FALSE. Then, the entire Boolean expression, including upper-level operators, can be evaluated from the values of the first-level copy-number nodes. As indicated by curved arrows, including curved arrow 2904, the array of references to logic expressions is traversed, similar to traversal of the array of logic expressions contained in clinical-action nodes, as discussed above with reference to FIG. 25, until an expression evaluates to TRUE. When an expression evaluates to TRUE, then the biological genomic element evaluates to TRUE. Otherwise, when no expressions evaluate to TRUE, the biological genomic element evaluates to FALSE. In certain implementations, the logic expressions can additionally contain routine calls, just as the logic expressions used in clinical-action nodes.

Figure 30A:
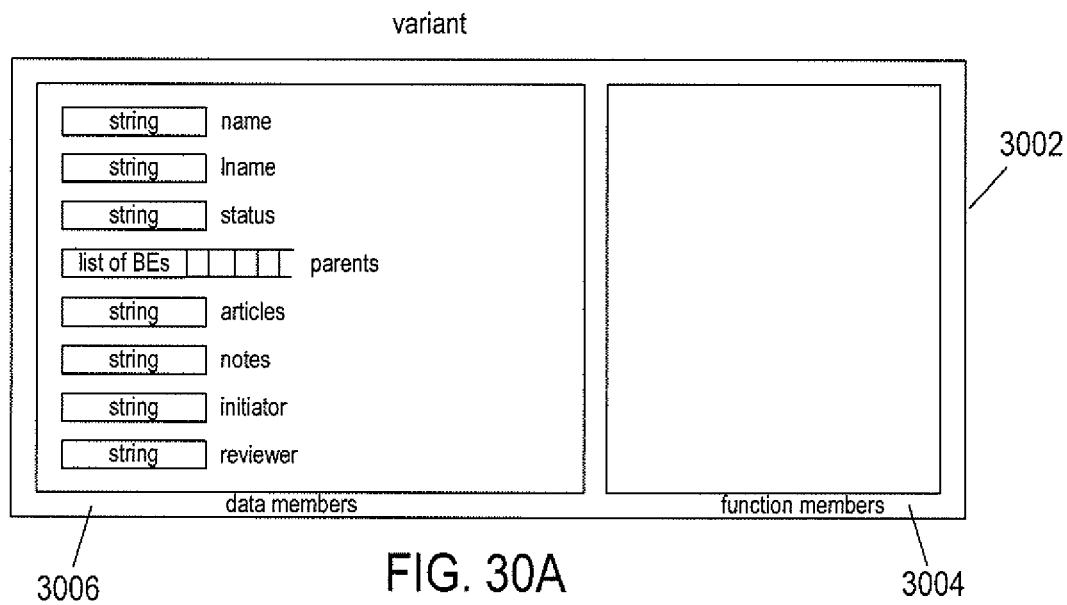
FIGS. 30A-B illustrate variant-node objects and variant-node-object inheritance.
Figure 30B:
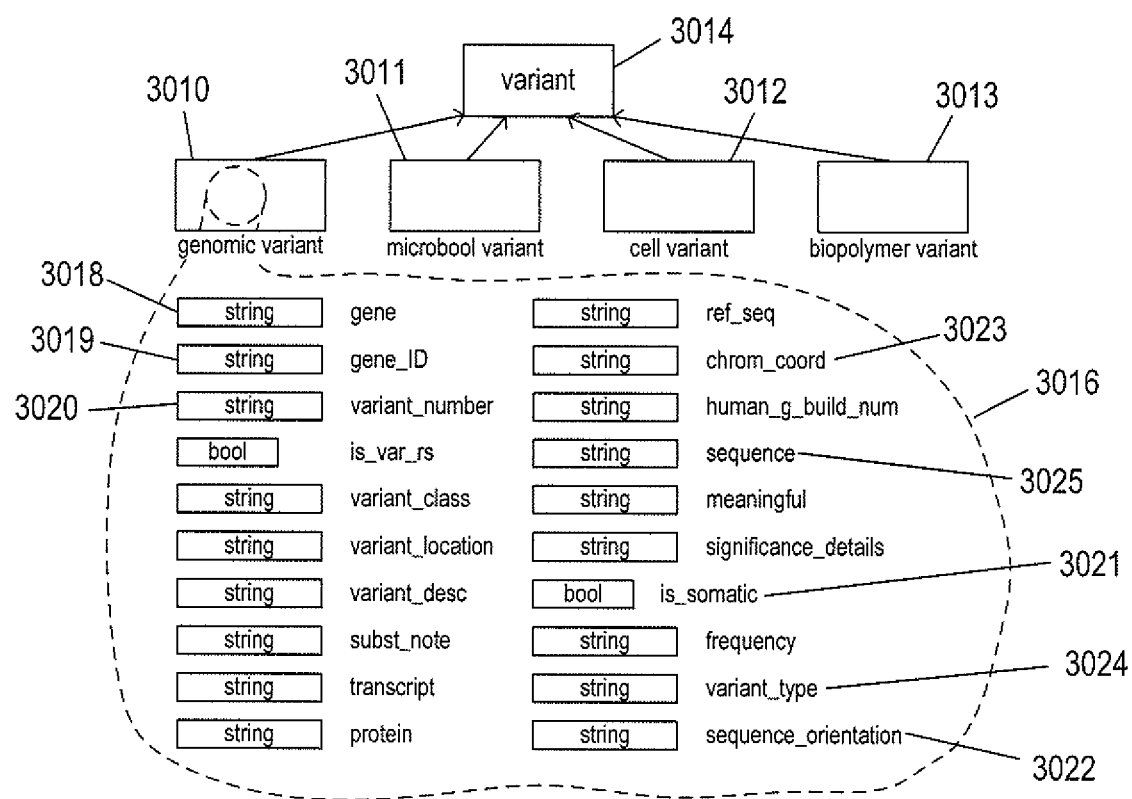

FIGS. 30A-B illustrate variant-node objects and variant-node-object inheritance. FIG. 30A shows the instantiated variant-node object. The variant-node object 3002 includes both function members 3004 and data members 3006, just like the biological-element-node objects and clinical-action-node objects discussed above with reference to FIGS. 23 and 26. All of the data members have equivalent meaning as the identically named data members in the biological-element node. As shown in FIG. 30B, each different type of variant node 3010-3013 is derived from a base variant-node class 3014. Each type of derived variant node includes additional data members, such as the additional data members shown in inset 3016 for the genomic variant node 3010. These include the name and ID of the gene in which the variant occurs 3018 and 3019, an identifier of the variant 3020, an indication of whether or not the variant is a semantic variant 3021, an indication of whether or not the sequence for the variant is 5'-to-3' or 3'-to-5' 3022, a coordinate for the variant 3023, the type of variant 3024, a sequence for an SNP or insertion variant 3025, and various other types of data members that describe the nature, type, and full details of the variant represented by the genomic variant node. Patient data stored within the cloud-like medical-information service generally contains a list of genomic variants identified in the patient by various types of genomic-analysis techniques, rather than the whole genomic sequence of the patient. Thus, the genomic variants listed for a patient can be easily searched to evaluate whether or not a particular genomic variant occurs in the patient and the copy number of the variant in the patient's genome. Thus, genomic-variant-node objects are directly evaluated from patient data.

Secure Information Exchange Within the
Cloud-Like Medical-Information System

Encryption methods transform a digitally encoded sequence of symbols, including text and numerical data, into a corresponding encrypted symbol sequence that cannot be straightforwardly read or interpreted, in general, but that contains the same information that is contained in the original symbol sequence that was encrypted to produce the encrypted symbol sequence. A party possessing a decryption key or other decryption-facilitating information can carry out an inverse transformation to regenerate the original symbol sequence. Encryption is used to transform a clear-text message or symbol string into encrypted form that cannot be interpreted by normal symbol-string interpretation algorithms, such as by reading natural-language statements. Decryption is the inverse process by which encrypted symbol strings are transformed back to clear-text form. An initial natural-language message M is transformed, by encryption 1, to an encrypted message C. In the current discussion, the expression "ENC(M, $k_e$)" stands for encryption of message M using encryption key $k_e$. The meaning of encrypted message C cannot be extracted by normal text-processing means. Instead, an encrypted message C needs to be first reverse-transformed back to a clear-text message by the decryption process. The expression "DEC(C, $k_d$)" stands for decryption of encrypted message C using decryption key $k_d$. This can be alternatively expressed as "$ENC^{-1}$(C, $k_d$)."

FIG. 31 summarizes three different encryption-based techniques referred to in the following discussions. Public-key/private-key encryption is widely used in commercial transactions and information-exchange protocols. One commercially successful public-key/private-key cryptosystem, also referred to as an "asymmetric" cryptosystem because different keys are used by the sender and the receiver, is named the "RSA" cryptosystem. The name RSA comprises the first letters of the last names of the inventors of the method: Ron Rivest, Adi Shamir, and Leonard Adleman. In this asymmetric cryptosystem, pairs of encryption/decryption keys are generated. In general, the encryption key is publically distributed, and referred to as the "public key," while the decryption key is held in secret solely by the key-pair-owning, encrypted-message-receiving party, and is referred to as the "private key" or "secret key." In normal usage, anyone can access the public key and encrypt a message using the public key, but only the receiving party in possession of the private key can decrypt and read the encrypted message.

For secure communications, two parties exchange their public encryption keys so that each party can encrypt a message and transmit the encrypted message to the other party for decryption and reading solely by the other party. However, because of the relatively high computational overhead for asymmetric cryptography, protocols such as the transport layer security ("TLS") protocol and the secure socket layer ("SSL") protocol usually begin a session with a handshake step in which public/private cryptography is used initially to establish a symmetric key that can be used more computationally efficiently for message encryption and decryption. Both parties use the symmetric key for the remainder of the session. The symmetric key is referred to as a "session key."

To generate an encryption/decryption key pair for the RSA cryptosystem, two prime numbers p and q are first selected, and the product n=pq is computed and saved. Next, the function $\varphi(n)$ is computed as (p−1)(q−1). Then, an integer e in the range (1, $\varphi(n)$) is selected such that the greatest common divisor of e and $\varphi(n)$ is 1. A corresponding integer d is computed such that (d*e) mod $\varphi(n)$=1. The public encryption key $k_e$ is the pair of integers (e, n) and the private, or secret, decryption key $k_d$ can be the four-tuple (d, n, p, q), the three-tuple (d, p, q), or the pair (d, n). To encrypt a message M, M is first transformed to an integer m in the range (0, n), the integer m is then subjected to the Optimal Asymmetric Encryption Padding (OAEP) randomized padding scheme, and the result is then raised to the power e modulo n or, as shown in FIG. 31:

$$C = (OAEP(m))^e \bmod n.$$

To decrypt the encrypted message C, the integer in is recovered by applying the inverse of the randomized padding scheme to the result of decrypting the message C by raising C to the power d modulo n, as shown in FIG. 31:

$$m OAEP^-(C^d \bmod n)$$

Finally, the integer m is transformed back into message M by the inverse of the forward transformation of M to m, performed as the first step of the encryption method. In certain cases, the initial transformation and final inverse transformations are omitted.

The RSA encryption/decryption method can also be used to digitally sign a message to provide authentication of the integrity of a transmitted message. Digital signing relies on the fact that, for a given initial value less than n, encryption is the inverse operation of the decryption operation, and vice versa. Digital signing proceeds as follows. First, a one-way cryptographic hash function is applied to the message M to produce a hash value, referred to as a "hash digest" of the message. Then, an optional transform may be applied to mHash to generate a further encoded message EM. Alternatively, the hash digest can be directly used as EM. Next, a signature for the message is generated by raising EM to the power d modulo n, equivalent to applying the RSA decryption method to EM using secret key $k_d$. This signature is appended to message M, along with the public encryption key, $k_e$, to be used to recover EM from the signature. A recipient of the message can verify the message by first generating mHash by applying the same one-way cryptographic hash function to the message M. The recipient next applies the RSA encryption method to the signature to generate a value EM' or, as expressed in FIG. 31:

$$EM = \text{signature}^e (\bmod\ n) = ENC(\text{signature}, k_s).$$

Next, in the case that the optional transform was applied to generate the signature, a corresponding reverse transform is applied to EM' to generate mHash'. When mHash' is equal to mHash, the hash value initially generated by applying the one-way cryptographic hash function to message M, the signature is verified. Note that the signer of the message uses the signer's private key, while the message can be verified by anyone with access to the signer's corresponding public key. Verification proves that the text of a received message M is identical to the text in the original message M that was signed by a party possessing the secret key $k_d$.

A digitally signed message comprises three elements: message contents M, a signature, and a public key used to recover a hash digest from the signature that is compared to a hash digest computed for M in order to verify M by a recipient of the message. A digitally signed message is vulnerable to a type of man-in-the-middle attack referred to as an "intercept/resign" attack. The attacker first intercepts a transmitted message. The attacker then alters the contents of the message M to produce new, different message contents M* and uses the attacker's own private key to generate a new signature for the new message contents M*, appending the new signature and the attacker's public key to the new message contents M* to generate a fraudulent digitally signed message. The sender information associated with the fraudulent digitally signed message is not altered by the attacker, so that the fraudulent digitally signed message appears, to a recipient, to have been received from the original sender. The fraudulent digitally signed message is then accepted and deemed to be valid by an unsuspecting recipient, because the verification method, discussed above, generates an mHash and mHash' that are equal to one another, despite the fact that the fraudulent digitally signed message includes altered message contents M*.

Other types of encryption/decryption methods employ a single key for both encryption and decryption. These methods are referred to as "symmetric key" cryptosystems. In this case:

$$C \leftarrow ENC(M, k)$$

$$M \leftarrow DEC(C, k).$$

Symmetric-key encryption uses a single key k for both encryption and decryption. There are many different cryptosystems for symmetric key encryption. One example is the Advanced Encryption Standard ("AES"). In general, symmetric-key encryption employs a series of deterministic operations for encryption that can be inverted for decryption. For symmetric-key encryption, the encryption key k is held in secret by both communicating parties since, once revealed, a message encrypted using the key k can be readily decrypted when k becomes known and when the particular symmetric-key-encryption method is also known.

At the bottom of FIG. 31, computation of a hash-based message authentication code ("HMAC"). Computation of an HMAC is carried out using a cryptographic hash function H, such as the MD5 and SHA-1 cryptographic hash functions. Computation of the HMAC involves use of a secret key K. As shown in FIG. 31, the HMAC is computed as a cryptographic hash of essentially two constants appended to the message. The HMAC can be re-computed, by a party knowing the secret key K and the two constants opad and ipad to check the authenticity of a received message m, and thus operates as a digital signature.

Figure 32:
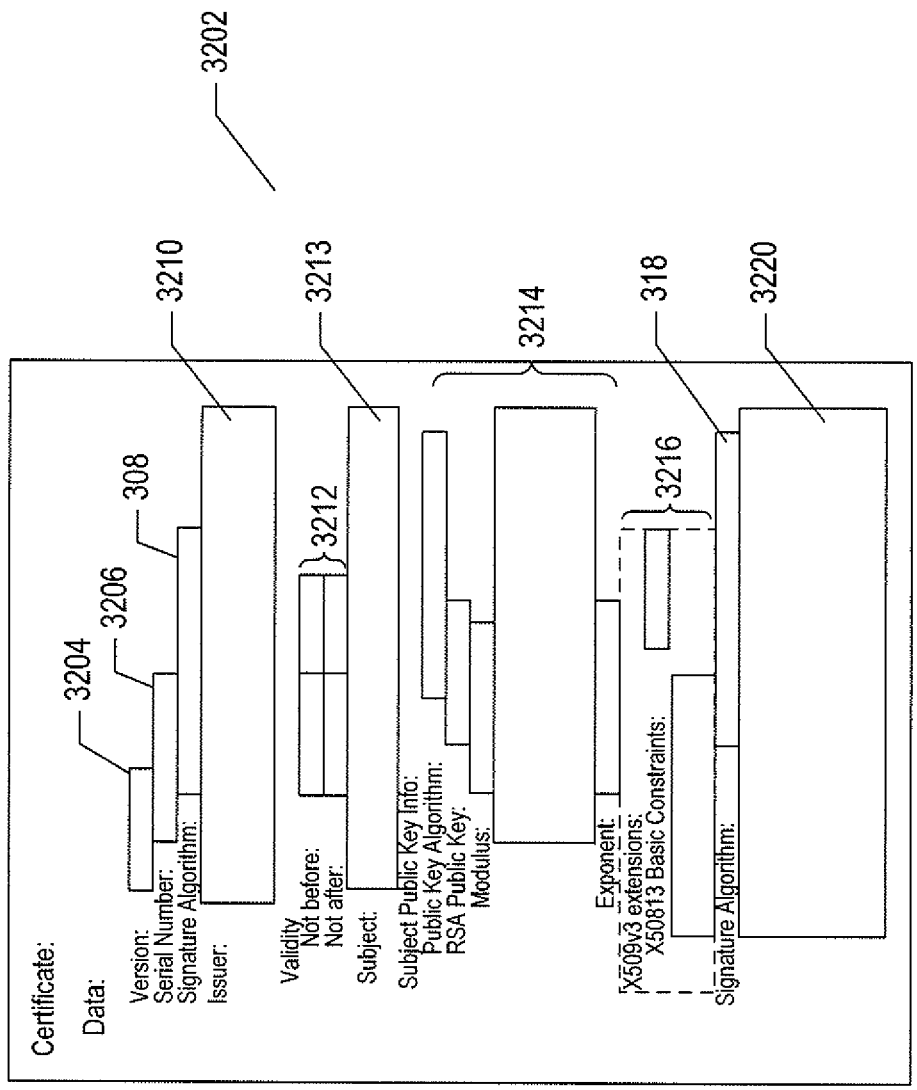
FIG. 32 illustrates the structure of an RSA X.509 public-key certificate.

Public-key certificates, including certificates that follow the X.509 ITU-T standard, are frequently used in secure communications for verifiably binding a public key to a name or identifier, such as a business entity name or a business or personal email address. FIG. 32 illustrates the structure of an X.509 public-key certificate. The X.509 certificate 3202 is essentially a data record that contains a sequence of standard fields that contain information needed to employ the certificate for verifying the binding, or association, of a user identifier or system identifier with a public key. These fields include a certificate version number 3204, a serial number 3206 that is unique with respect to a particular certificate authority that issues public-key certificates, an encoding of an identifier for the cryptographic method used to compute a signature over the certificate 3208, information that identifies the issuer of the certificate 3210, two date and time values 3212 that indicate the beginning date and time at which the certificate becomes valid and the ending date and time at which the validity of the certificate ends, identifying information for the user or system that is bound by the certificate to a public key 3213, a group of fields that indicate the cryptographic algorithm for which the public key is used and that include the public key 3214, optional fields 3216, referred to as extensions, that include additional information, an indication of the signature algorithm 3218, and the signature, computed by the issuing entity over the remaining fields of the certificate 3220. In some cases, the additional information section can contain indications of a security protocol to be used when establishing a secure connection.

In general, public-key certificates are issued by trusted computer systems within entrusted organizations known as "Certificate Authorities" ("CAs"). CAs are well-known certificate-issuing organizations that issue public/private key pairs, including corresponding public-key certificates, as a commercial service. These organizations employ various due-diligence information-gathering techniques to verify the identity of a requesting entity prior to issuing a key pair and public-key certificate. Large organizations, such as universities or big companies, may perform the function of a CA in order to generate public-key certificates for their use, referred to as "self-signing."

A public-key certificate is transmitted, by a first entity possessing the public-key certificate and the corresponding private key, to other entities in order to enable the other entities to securely transmit information to the first entity and to enable the first entity to digitally sign information that can then be verified by use of the public key by the other entities. For email, a sender transmits the sender's public key to other entities by signing emails transmitted to the other entities. The public key component of the digital signature can be saved for further use by those who receive the emails. Public-key distribution by this method generally involves public-key management, including procedures for public-key revocation, expiration, and replacement. Public-key management may be a burdensome overhead, often resulting in complexity that hinders use of encryption for communications.

FIGS. 33A-F illustrate a basic, public/private-key-based secure information exchange between a user and a remote responder. This type of secure information exchange is implemented in various protocols, including the HTTPS secure protocol. FIGS. 33A-F all use the same illustration conventions, next described with reference to FIG. 33A. The various computer systems are represented in FIGS. 33A-F by rectangles, such as rectangle 3302 representing a user computer, rectangle 3304 representing a responder computer, rectangle 3306 representing one or more intermediate computers that interconnect the user computer to remote computers via the Internet or another public network, rectangle 3308 that represents intermediate computers that interconnect the responder computer 3304 with the Internet or another public network, and one or more computer systems 3310 within an organization that serves as a certificate authority. Arrows, such as arrow 3312, indicate transmission of information as one or more messages or packets from one computer to another, with certain of the arrows labeled with indications of the type of message being sent. Finally, the figures include numerically labeled indications of the steps involved in the information exchange, the numerical labels indicating the order of the steps in the sequence, such as circled numerical label "1" 3314 indicating the first step in the process.

In a first step, the browser on the user's computer, in certain cases in response to certain user inputs, and, in other cases, in response to internal events, generates a new public/private key pair $k_e/k_d$ and then requests a public-key certificate from the certificate authority 3310 via a request message 3316. The request message is sent through various severs and routers 3306 and intermediate routing systems within the public network to the certificate authority 3310. In general, although not shown in FIG. 33A, the certificate authority would undertake information exchange with the browser on behalf of the user in order to obtain sufficient information to verify the user's identity and IP and email addresses. Upon verification, a certificate authority 3310 returns a public-key certificate, such as the X.509 certificate discussed above with reference to FIG. 3, in a message 3318 to the user. Similarly, the responder computer, in certain cases through a browser or application program, also generates a public/private key pair $k'_e/k'_d$, requests a certificate for the public key $k'_e$ from the certificate authority in a request message 3320 and, upon verification, receives a public-key certificate from a certificate authority in a response message 3322. Note that the responder may use a different certificate authority than the certificate authority used by the user, or be a self-signer, although, in FIG. 33A, the same certificate authority 3310 is shown as being used by both the user and responder.

Figure 33A:
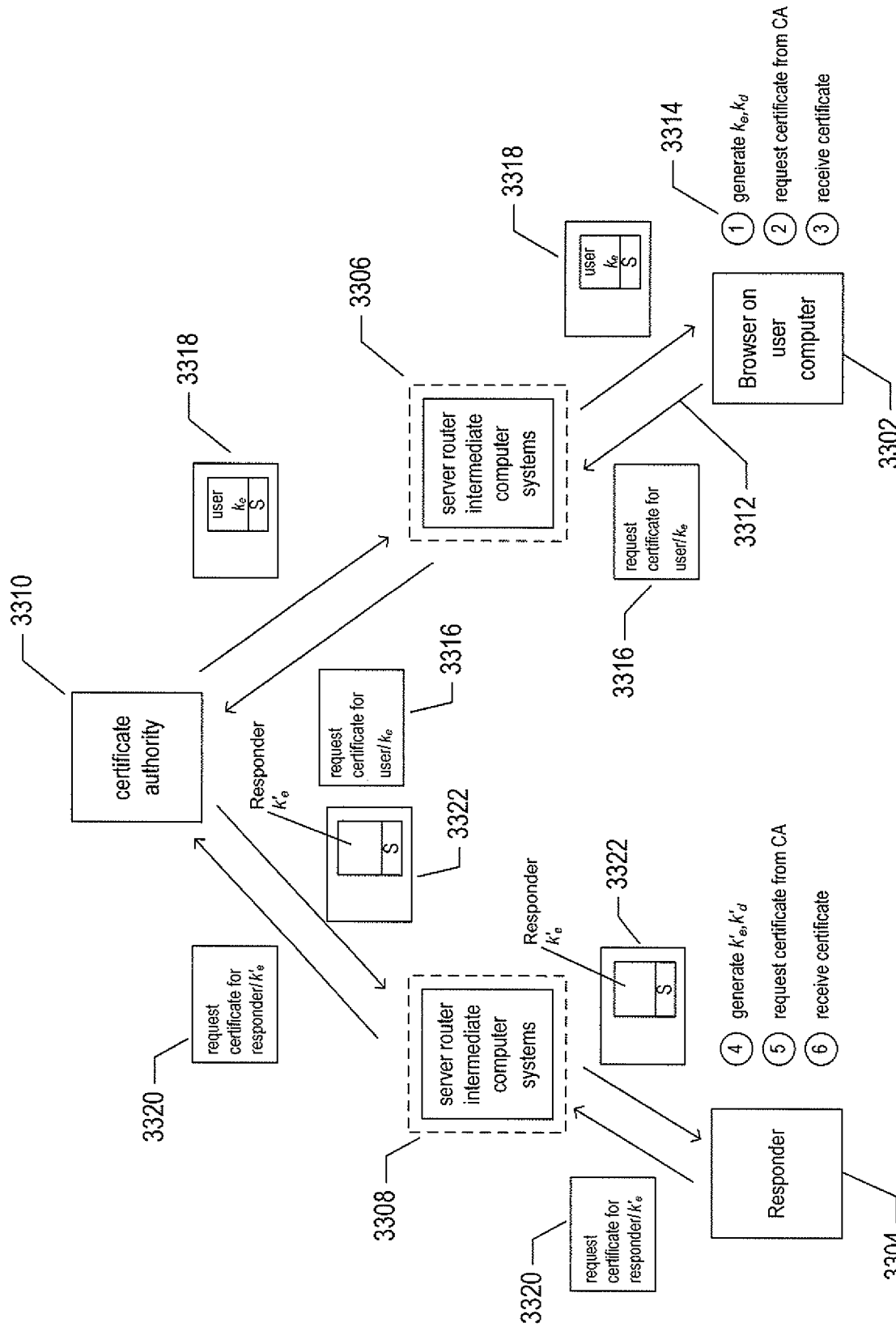
FIGS. 33A-F illustrate a basic, public/private-key-based secure information exchange between a user and a remote responder.
Figure 33B:
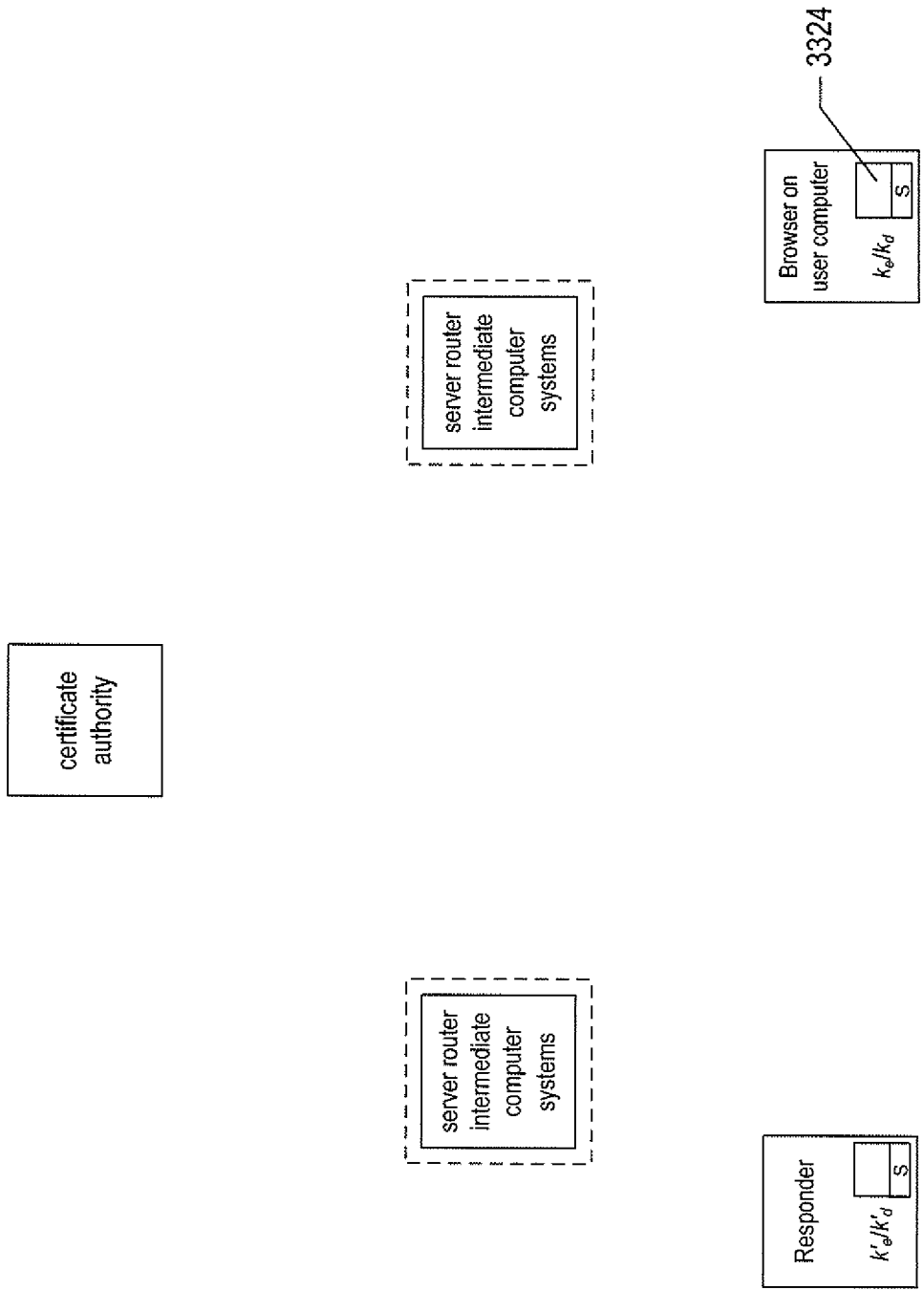

Thus, as a result of the certificate requests and responses illustrated in FIG. 33A, both the user computer and responder computer have stored public/private keys as well as certificates for their respective public keys. FIG. 33B illustrates this state of the user computer and responder computer prior to initialization of an information exchange. In FIG. 33B, as in other figures of FIGS. 33A-F, the public-key certificates are represented by rectangles, such as rectangle 3324, with the lower section labeled "S" representing the signature over the certificate generated by the certificate authority using the certificate authority's private key.

Figure 33C:
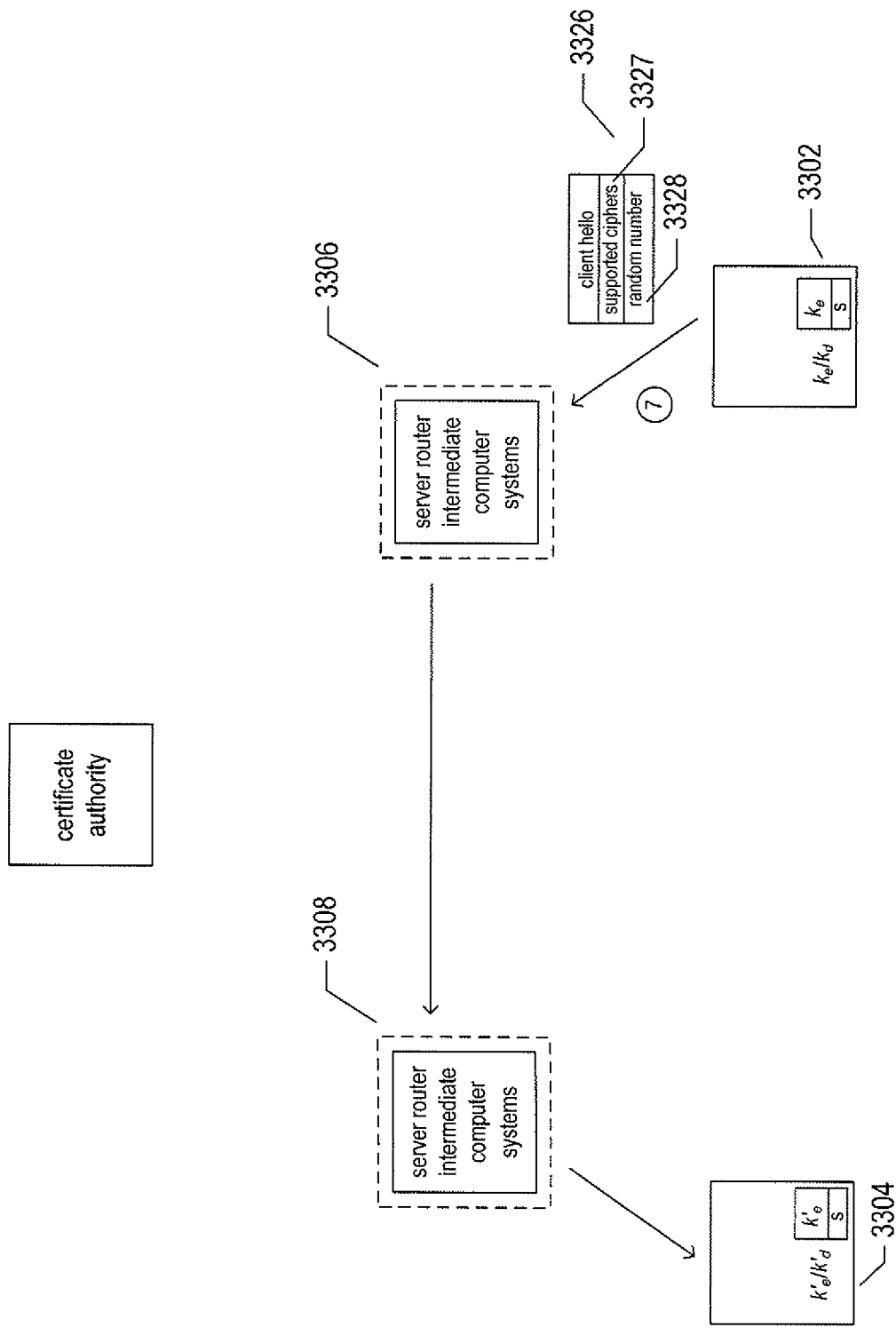

Next, as shown in FIG. 33C, the browser on the user computer, generally in response to user input, generates a request for initial information from the responder and transmits that request to the responder, shown as step 7. For establishing a secure-communication session, the initial request is referred to as a "client-hello" message and is a first step of a multi-step handshake carried out between a user, also referred to as the "client" or the "requestor," and a responder, also referred to as the "server." The client-hello message 3326 includes indications 3327 of the ciphers supported by the user's browser and a random number selected by the user's browser. The multi-step handshake establishes: (1) the cryptography methods used during the session; (2) particular cryptographic keys used during the session; and (3) mutual authentication. There are many protocols used for establishing secure communications. The current discussion assumes use of an SSL RSA handshake. The currently disclosed methods and systems may employ many other types of protocols used for establishing secure communications.

Figure 33D:
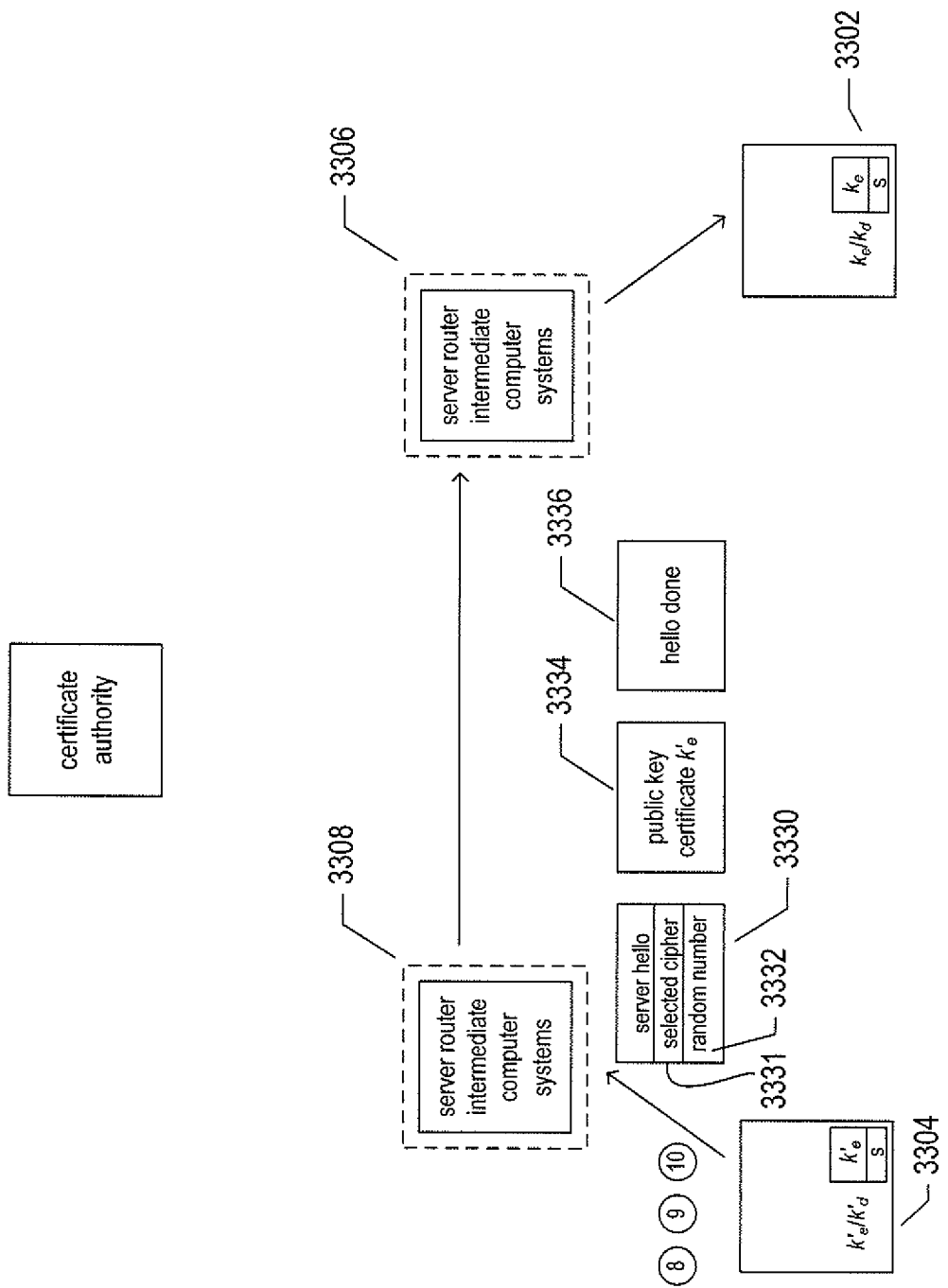

Next, as shown in FIG. 33D, the responder responds to receipt of the client-hello message by, in step 8, returning to the user a server-hello message 3330 that includes an indication of a selected cipher 3331 and a random number generated by the server 3332. In step 9, the responder sends the responder's public-key certificate 3334 to the user. In step 10, the responder sends a hello-done message 3336 to the user. In certain protocols and implementations of protocols, multiple messages may be combined together in fewer transmitted messages.

Figure 33E:
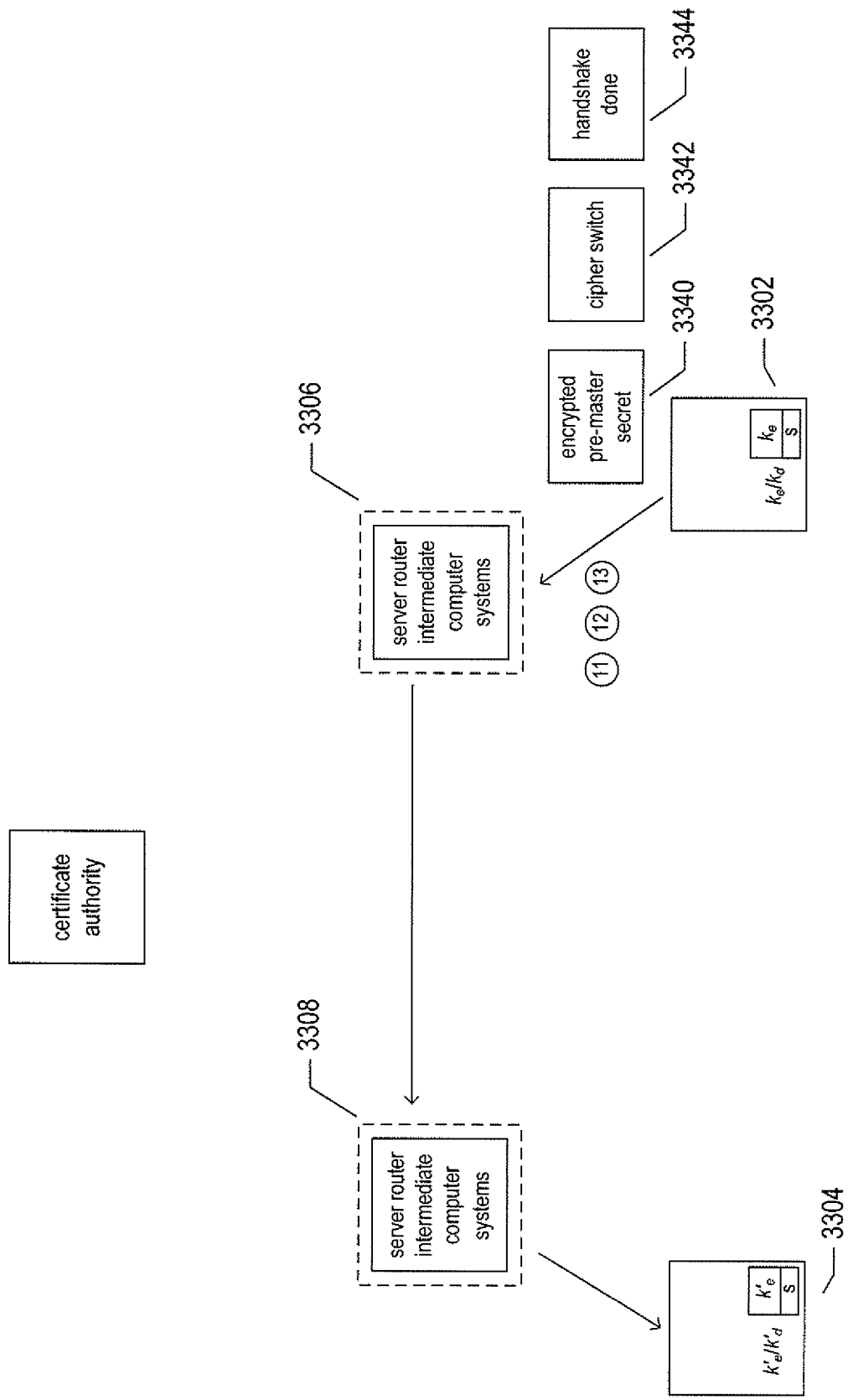

Next, in step 11, as shown in FIG. 33E, the user, in response to receiving the server-hello message, public-key certificate, and hello-done messages from the responder, transmits an encrypted pre-master secret 3340 to the responder, encrypting the pre-master secret using the responder's public key. The pre-master secret is generated as a function of the random numbers exchanged by the user and responder. Then, in step 12, the user transmits a cipher-switch message 3342 to the responder. Finally, in step 13, the user transmits a handshake-done message 3344 to the responder.

Figure 33F:
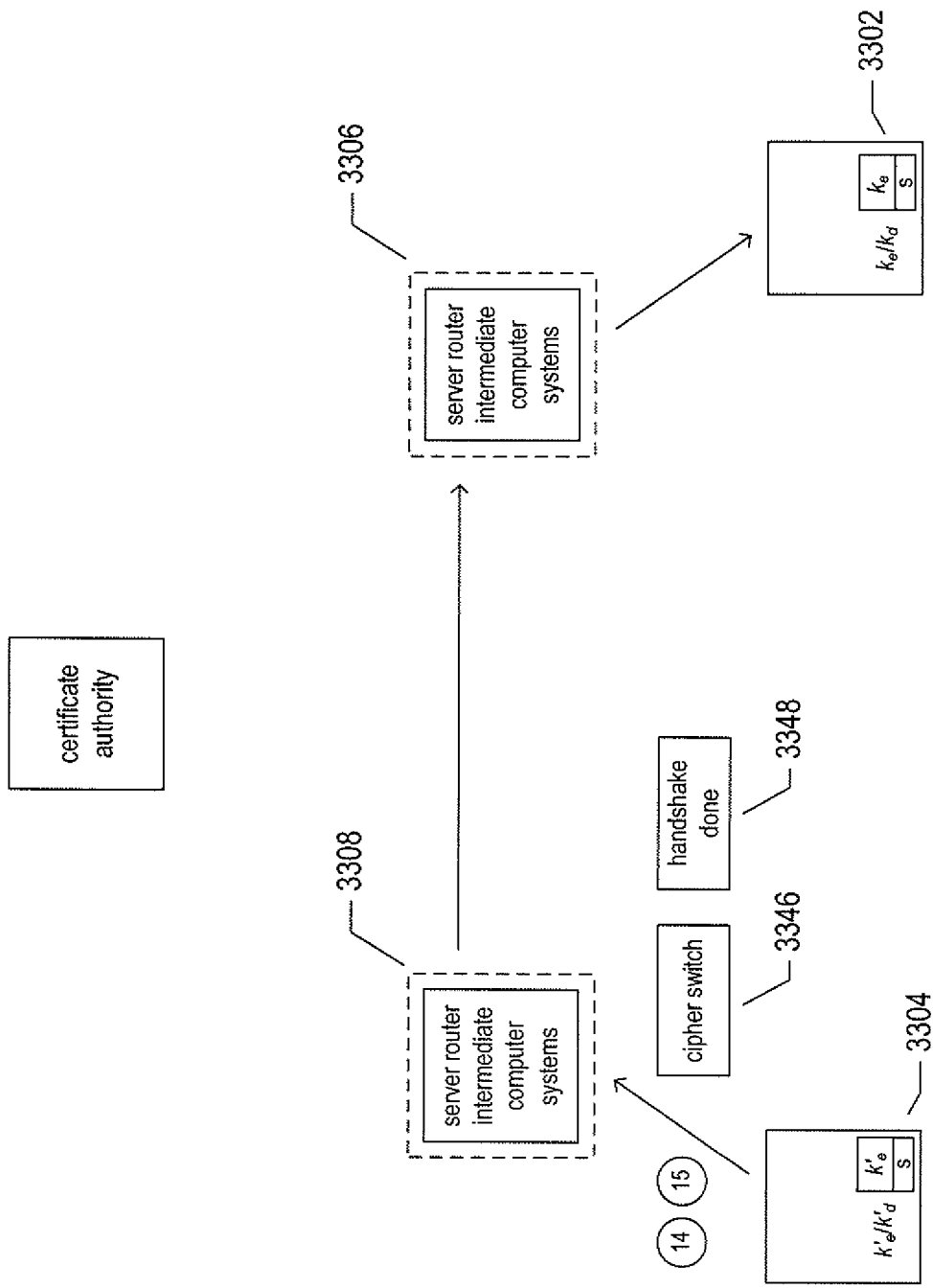

As shown in FIG. 33F, the responder responds to receipt of the encrypted pre-master secret, cipher-switch message, and handshake-done message by, in steps 14 and 15, returning to the user a cipher-switch message 3346 and a handshake-done message 3348. At this point, the user and responder can continue to exchange encrypted messages using the selected cipher and a symmetric encryption key generated from the pre-master secret.

After transmission of the encrypted pre-master secret by the user to the responder, in step 11 shown in FIG. 33E, the user and responder compute the symmetric session key that is used to encrypt transmissions following completion of the handshake, in both directions, for the remainder of the session. At this same point in the process, the user and responder also compute a key used to compute message authentication codes ("MACs") for the handshake messages. Such MACs can then be compared for additional validation of the integrity of a completed handshake. A secure successful conclusion of the handshake protocol relies on: (1) correct and unaltered transmission of the random numbers in steps 7 and 8; (2) correct and unaltered transmission of the supported-cipher and cipher-selection information; and (3) successful authentication, by the user, of the responder's public-key certificate and determination, by the user, that the responder's public-key certificate is valid and unrevoked, which may involve access of a database of revoked certificates.

FIGS. 34A-F illustrate security methods employed in one implementation of the cloud-like medical-information system. An external client 3402 communicates through the Internet 3406 with the cloud-like medical-information system 3408 via the HTTPS secure protocol 3408. Within the cloud-like medical-information system, communications between data-storage facilities 3410 and various service-providing servers 3412 and 3414 are also carried out using the HTTPS secure protocol 3416-3420. In addition, all of the clinical-knowledge information stored within the clinical-knowledge data structure and patient data are fully encrypted when stored in the data-storage facility 3410 within the cloud-like medical-information system. Thus, in no case is clear-text information accessible externally from the various components of the cloud-like medical-information system and the user computers.

Figure 34A:
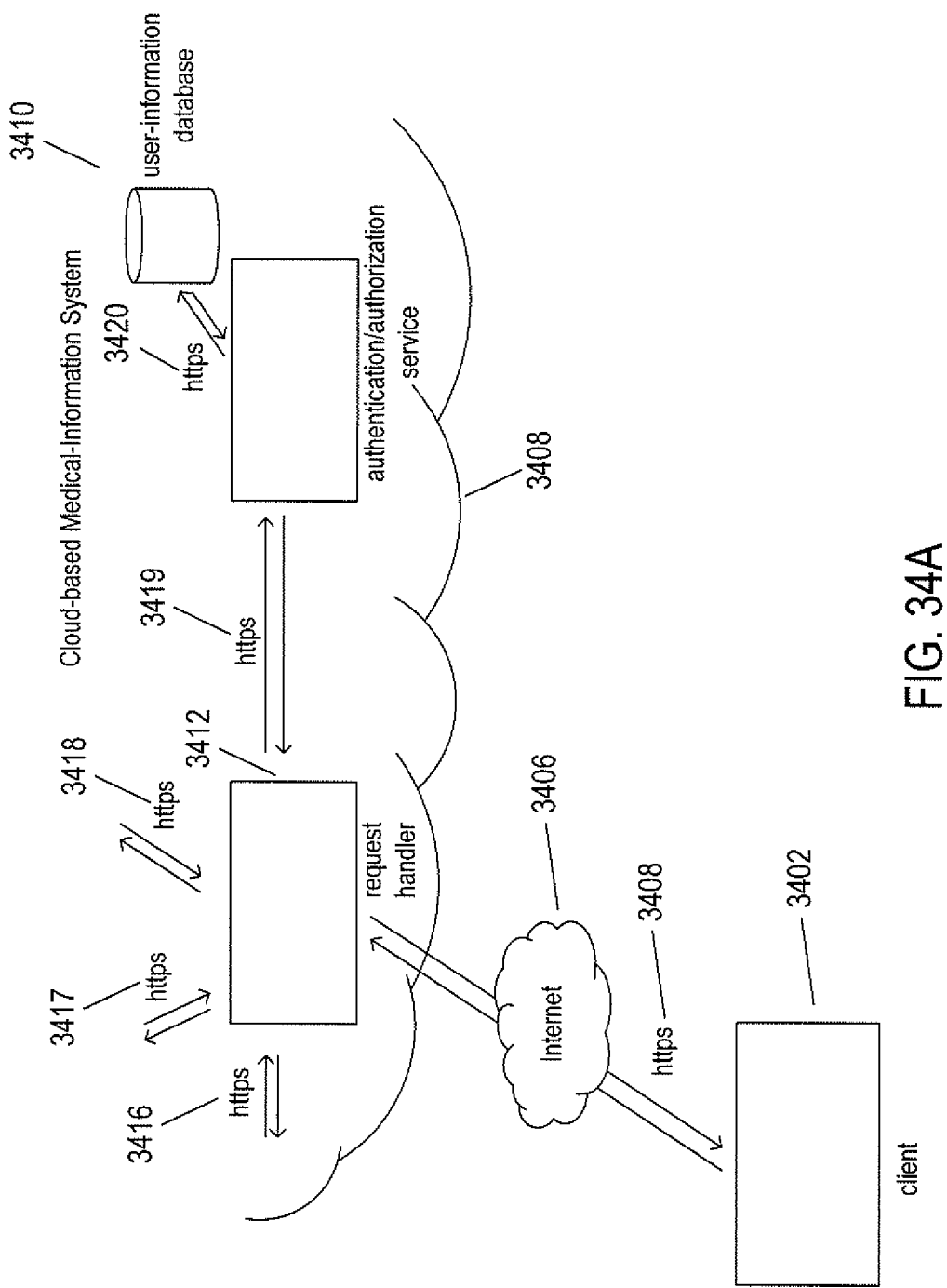
FIGS. 34A-F illustrate security methods employed in one implementation of the cloud-like medical-information system.
Figure 34B:
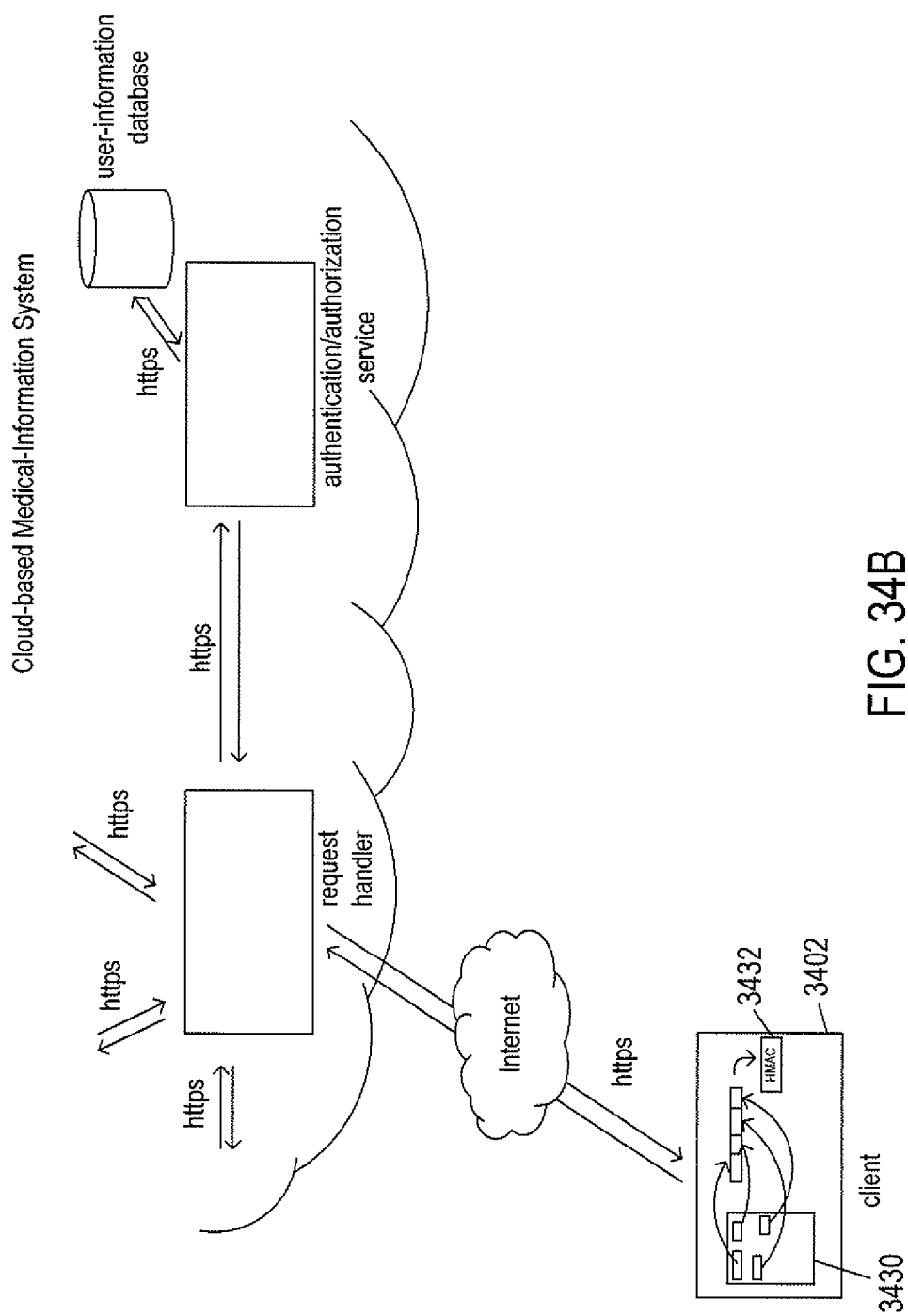
Figure 34C:
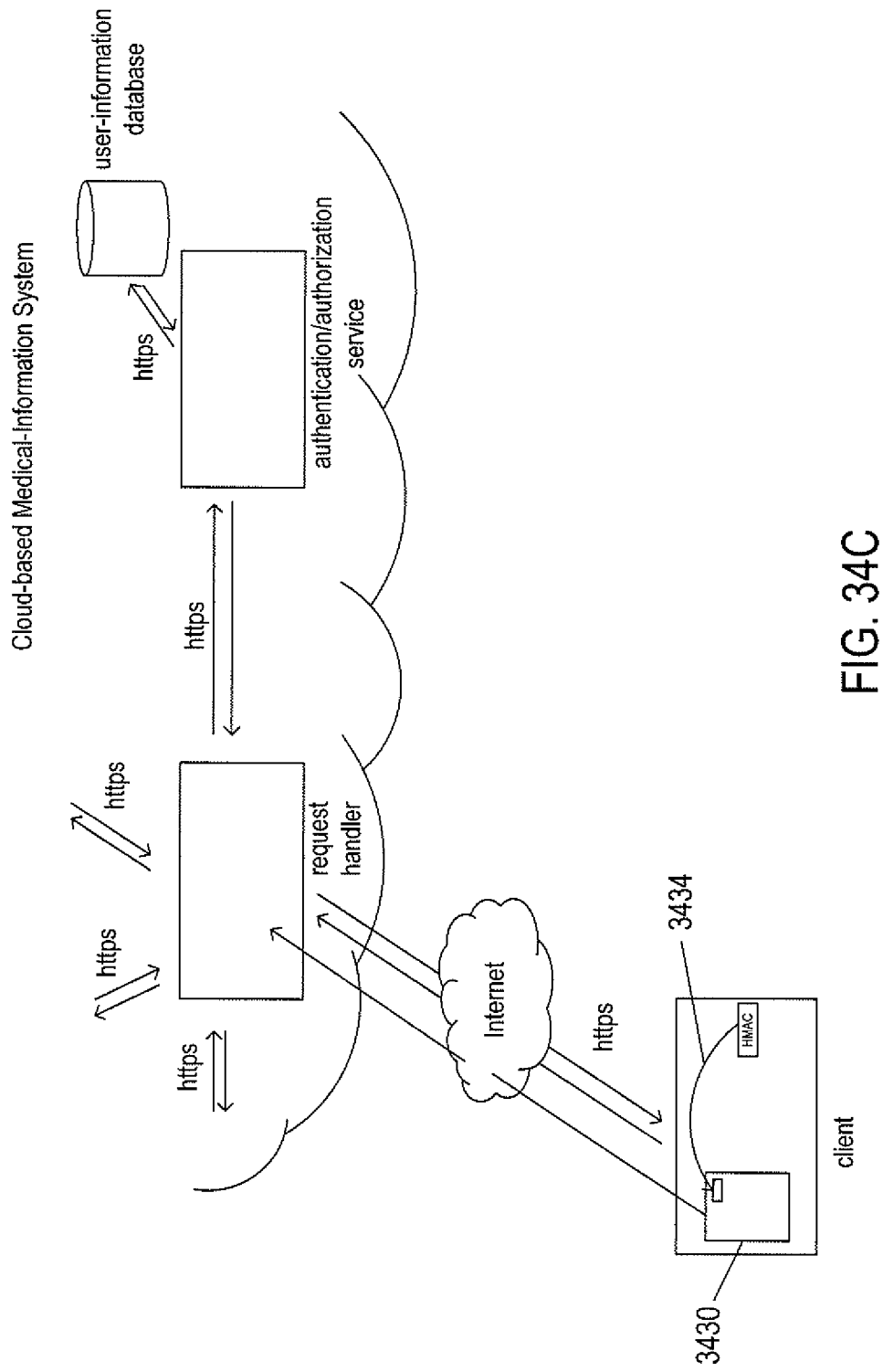
Figure 34D:
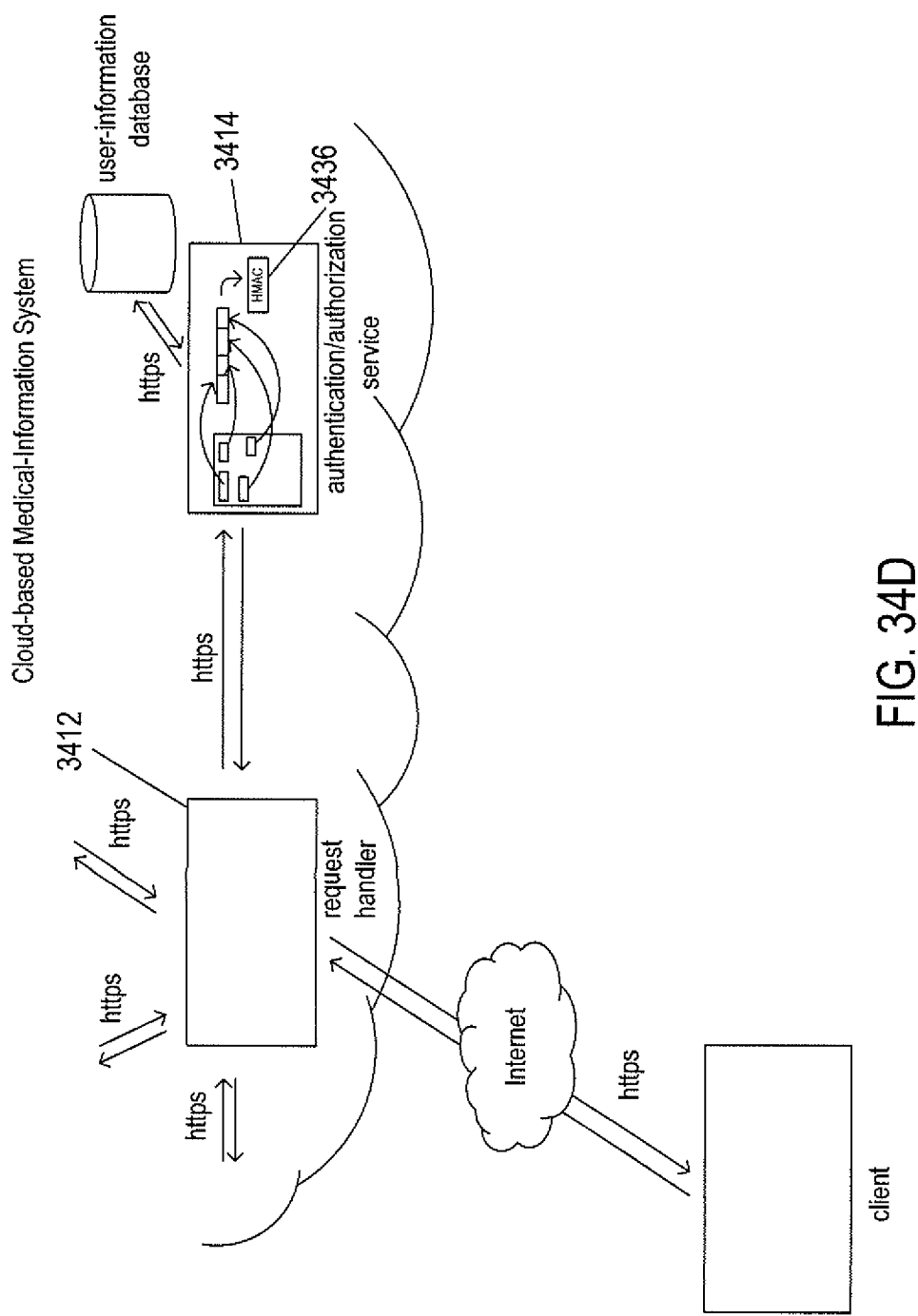
Figure 34E:
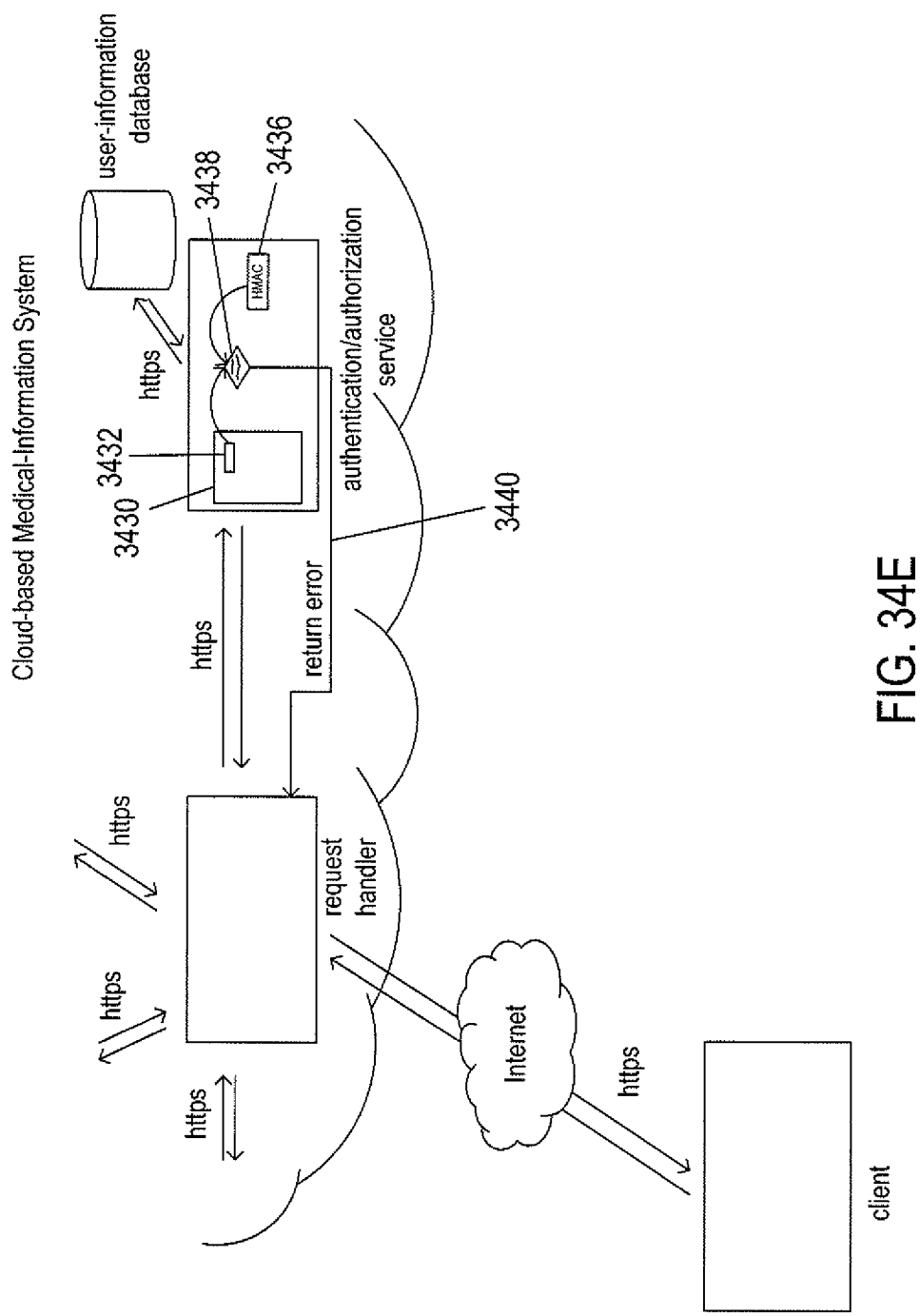
Figure 34F:
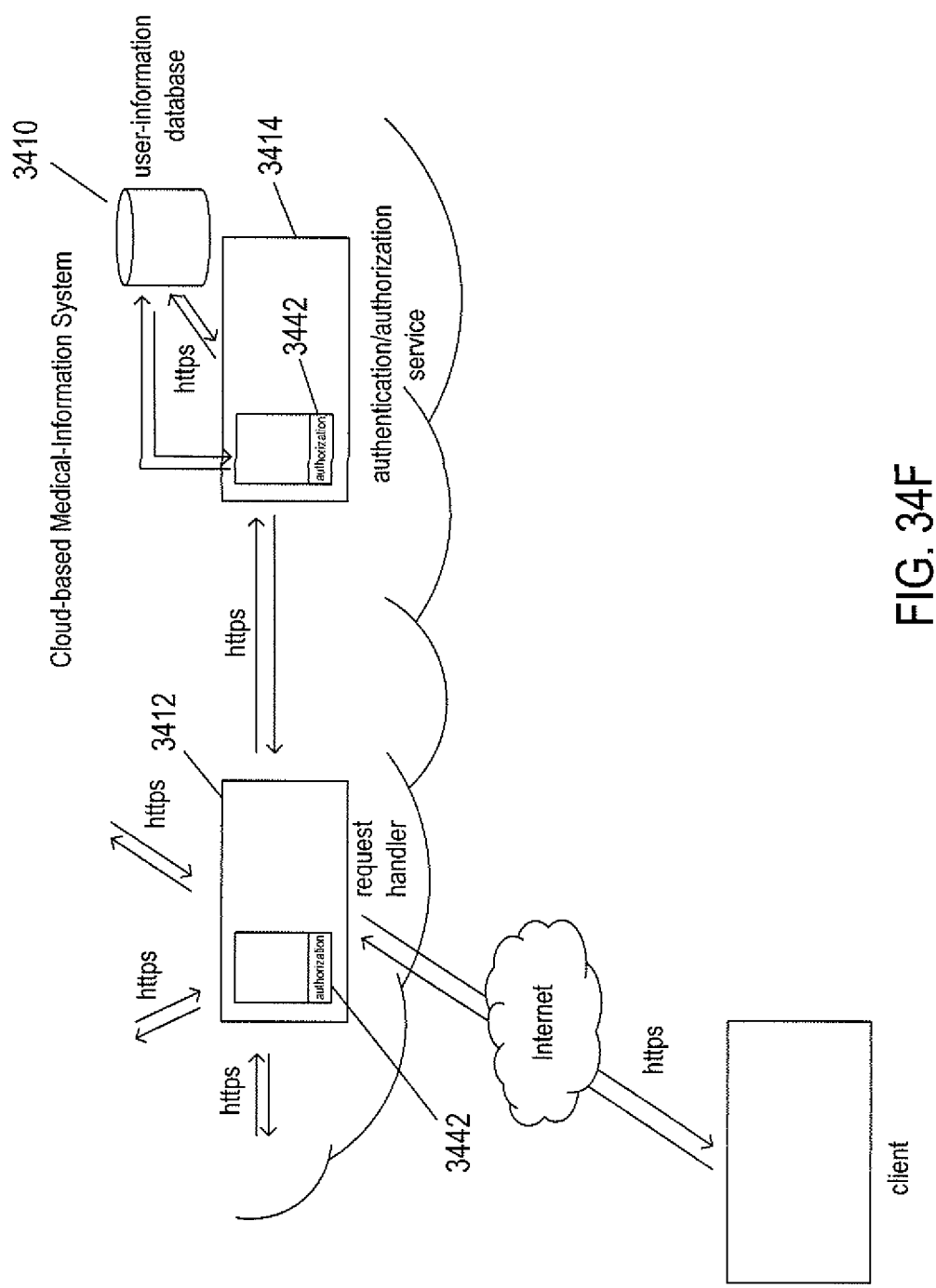

In FIG. 34B, a user interfacing to a client computer 3402 enters input that results in preparation of a request, or query, to be sent to the cloud-like medical-information system in a message for transmission to the cloud-like medical-information system via the HTTPS protocol. When the message has been prepared, with request information encoded within a JSON body of an HTTP GET or POST message 3430, the client-side functionality of the cloud-like medical-information system prepares an HMAC digital signature 3432 for the message and, as shown in FIG. 34C, places the HMAC digital signature 3434 into the header of the message 3430. In certain implementations, the HMAC is computed from one or more selected portions of the message, rather than from the entire message. The request message is received by a request-handler server 3412 and forwarded to an authentication/authorization-service-providing server 3414 for authentication and authorization. First, as shown in FIG. 34D, the authentication/authorization service re-computes the HMAC 3436 and then compares 3438 to the computed HMAC 3436 with the HMAC 3432 included in the received message 3430, as shown in FIG. 34E. When the two HMACs are identical, the message is authenticated. Otherwise, the authentication/authorization service returns an error 3440 to the request handler, which may undertake any of various error-handling procedures. Then, as shown in FIG. 34F, the authentication/authorization service 3414 accesses the data-storage facility 3410 within the cloud-like medical-information service in order to determine whether or not the user identified in the message is authorized to receive a response to the request contained within the message. An indication of the user's authorizations, or roles, 3442 are appended to the message and the message is returned to the request-handler service 3412 which can then access the authorization information 3442 in the returned message to determine whether or not to process the user's request.

Many other types of security measures may be undertaken within the cloud-like medical-information system in addition to, or in place of, the above-described security methods. For example, fine-grain authorization control of patient data may be implemented to ensure that patients may protect their data and authorize access to patient data at relatively fine granularity, such as allowing access to particular gene-variant information and particular fields within patient-describing records and determining which practices/institutions or individual clinicians can access the data. Various types of user-identification techniques may be employed to ensure that a user identified within a request is associated with the computational device from which the request was transmitted and that the computational device is currently controlled by the identified user. Keys for computing HMACs and other such secret information are generally distributed by secure means, and may be updated periodically by the cloud-like medical-information service to enhance overall security of the system.

Figure 35:
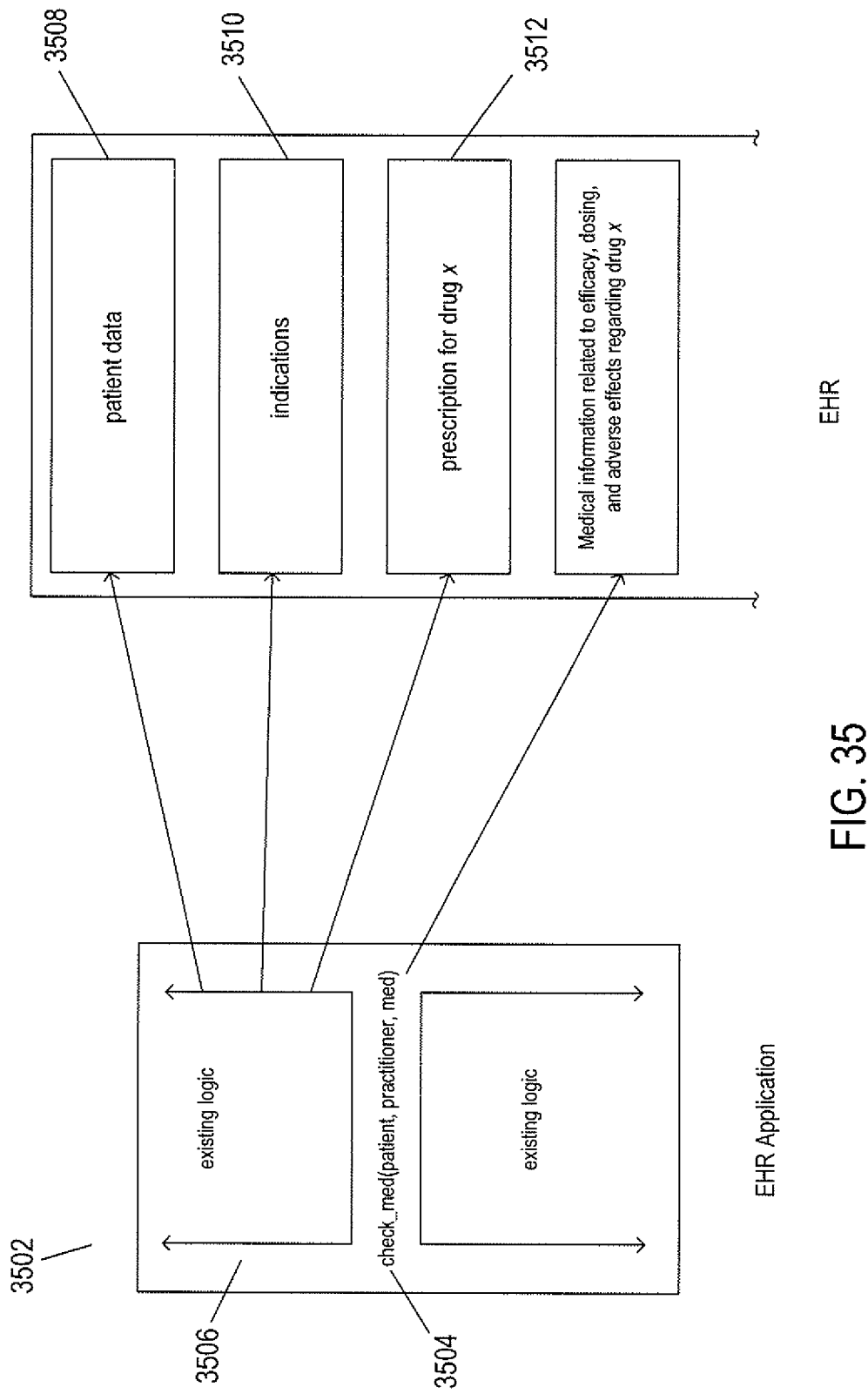
FIG. 35 illustrates the context in which a request is generated, from a user computer, for processing by the cloud-like medical-information service.

An Example Request/Response Transaction Carried
Out by the Described Implementation of the
Cloud-Like Medical-Information System FIG. 35 illustrates the context in which a request is generated, from a user computer, for processing by the cloud-like medical-information service. The user computer, in this example, is currently executing an EHR application 3502. A routine call 3504 has been placed into the EHR application in order to check for any patient-specific genomic indications with respect to a prescribed medication. In previously executed logic 3506 within the EHR application, the EHR application has collected various types of data, including patient data 3508, medical indications 3510, data regarding prescription, by a medical-services provider, of medications to treat the patient 3512, laboratory data, vital signs data, procedures data, and family-history data. The existing EHR application has been enhanced with the routine call 3504 in order for the cloud-like medical-information system to compare stored genomic information for the patient with any medication-related clinical-action nodes within the clinical-knowledge data structure stored in the cloud-like medical-information system in order to identify any relevant clinical-action nodes, as discussed above with reference to FIG. 19, and to display output information from any relevant clinical-action nodes to the medical-service provider, allowing the medical-service provider to perhaps reconsider prescription of the particular medication. Note that existing EHR applications can be easily enhanced, by the addition of calls to various library routines made accessible to the existing EHR application, in order to access any of a wide variety of different types of information stored within the clinical-knowledge data structure in the cloud-like medical-information system as well as data for the particular patient stored within the cloud-like medical-information system. Costly redevelopment of existing EHR applications can be avoided while enhancing existing EHR applications to access enormous amounts of carefully curated and aggregated medical information and specific patient data.

Figure 36A:
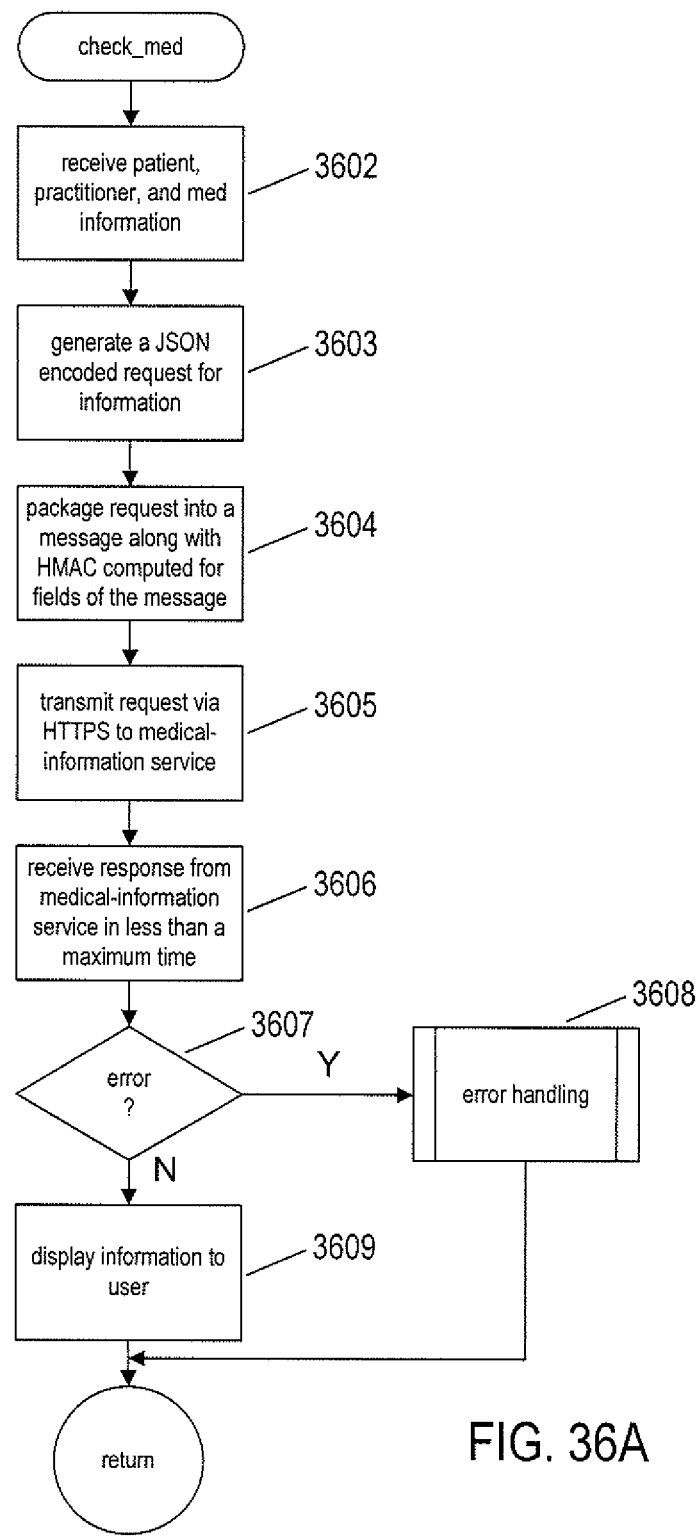
FIGS. 36A-E provide control-flow diagrams that describe how the routine call made from the EHR application in the example illustrated in FIG. 35 is carried out, both on the client side and within the cloud-like medical-information service.

FIGS. 36A-E provide control-flow diagrams that describe how the routine call 3504 made from the EHR application in the example illustrated in FIG. 35 is carried out, both on the client side and within the cloud-like medical-information service. FIG. 36A provides a control-flow diagram for the routine "check_med" called from the existing EHR application in the example shown in FIG. 35. In step 3602, the routine "check_med" receives patient, practitioner, and pharmaceutical information provided in arguments included in the routine call. In step 3603, the routine "check_med" generates a JSON-encoded request for genomic indications with respect to the medicine identified in the arguments supplied in step 3602. In step 3604, the routine "check_med" packages the request into a message along with an HMAC computed for fields of the message and, in step 3605, transmits the request via the secure HTTPS protocol to the cloud-like medical-information service. In step 3606, after waiting for a response to be returned, the routine "check_med" receives the response from the medical-information service in less than a maximum turnaround time that is a designed parameter of the cloud-like medical-information service. In the disclosed implementation, the maximum turnaround time is one second. In alternative implementations, this maximum turnaround time may be reduced to one-half of a second, one-tenth of a second, or to even smaller maximum turnaround times. When the received response indicates that some type of error has occurred, as determined in step 3607, then the routine "check_med" undertakes appropriate error handling, in step 3608. Error handling may involve resubmitting a request, querying the user for additional or different information to include in a subsequent attempt to submit the request, display of an informational message regarding the error, or other types of error handling. Otherwise, in step 3609, the routine "check_med" displays any medical indications returned in the response message to the routine "check_med" by the cloud-like medical-information service.

Figure 36B:
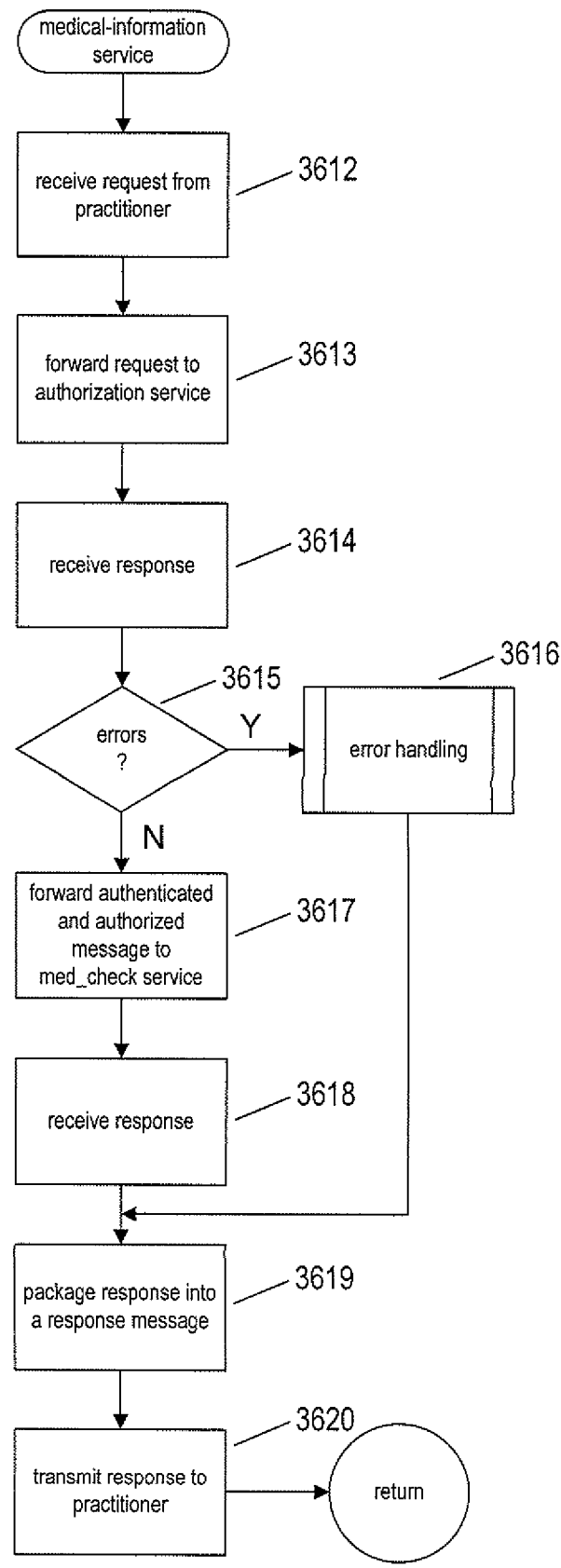

FIG. 36B illustrates initial and final handling of the request by a request-handling service within the cloud-like medical-information service. In step 3612, the request is received from the practitioner or medical-service organization for genomic indication information with respect to a particular patient. In step 3613, the request is forwarded by the request-handling service to an authorization service within the cloud-like medical-information system. After waiting for the authorization service to respond, the request-handling service, in step 3614, receives a response. If the response indicates any of various types of errors, as determined in step 3615, then the request-handling service undertakes error handling, in step 3616. Error handling may involve returning an error message to the requestor, retrying authorization after a dialog with the user, or other types of error handling. In step 3617, the request, now including authorization information, is forwarded by the request-handling service to a medicine-check service. The request-handling service waits for a response to be received from the medicine-check service and, in step 3618, receives a response from the medical-check service. In step 3619, the response is packaged into a response message which, in step 3620, is transmitted to the practitioner or medical-service organization that initially submitted the request.

Figure 36C:
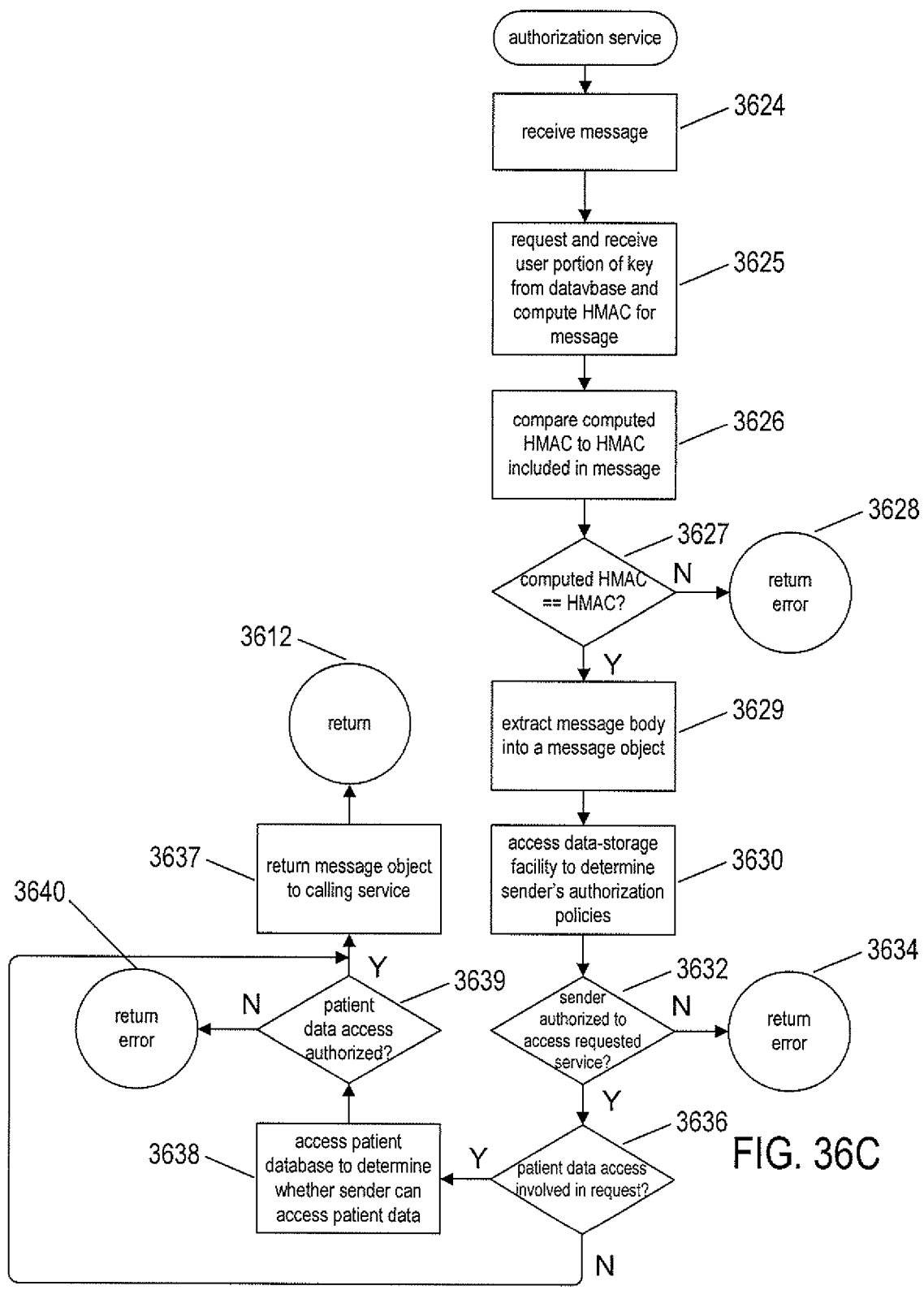

FIG. 36C illustrates the handling of the message by the authorization service, after the request-handling service forwards the message to the authorization service in step 3613 in FIG. 36B. In step 3624, the authorization service receives the message. In step 3625, the authorization service either accesses a key for the user stored in a local cache or requests and receives the key from a database and then computes an HMAC for the message. In step 3626, the newly computed HMAC is compared to the HMAC included in the message by the client-side "check_med" routine, in step 3604 in FIG. 36A. When the newly computed HMAC is not identical to the HMAC included in the message, as determined in step 3627, the authorization service returns an error to the request-handling service in step 3628. Otherwise, the authorization service extracts the message body from the request message into a message object, in step 3629. In step 3630, the authorization service accesses a data-storage facility to determine the authorization policies associated with the user or sender of the message. When the sender is not authorized to access a requested service, as determined in step 3632, an error is returned in step 3634. Otherwise, when no patient data is involved and processed in the request, as determined in step 3636, then the message object created in step 3629 is returned to the request-handling service in step 3637. Otherwise, in step 3638, the authorization service accesses a patient database to determine whether or not the sender can access the particular patient data needed to process the request, or query. When access to the patient data is authorized for the request sender, or user, as determined in step 3639, then the message object is returned to the request-handling service in step 3637. Otherwise, an error is returned in step 3640.

Figure 36D:
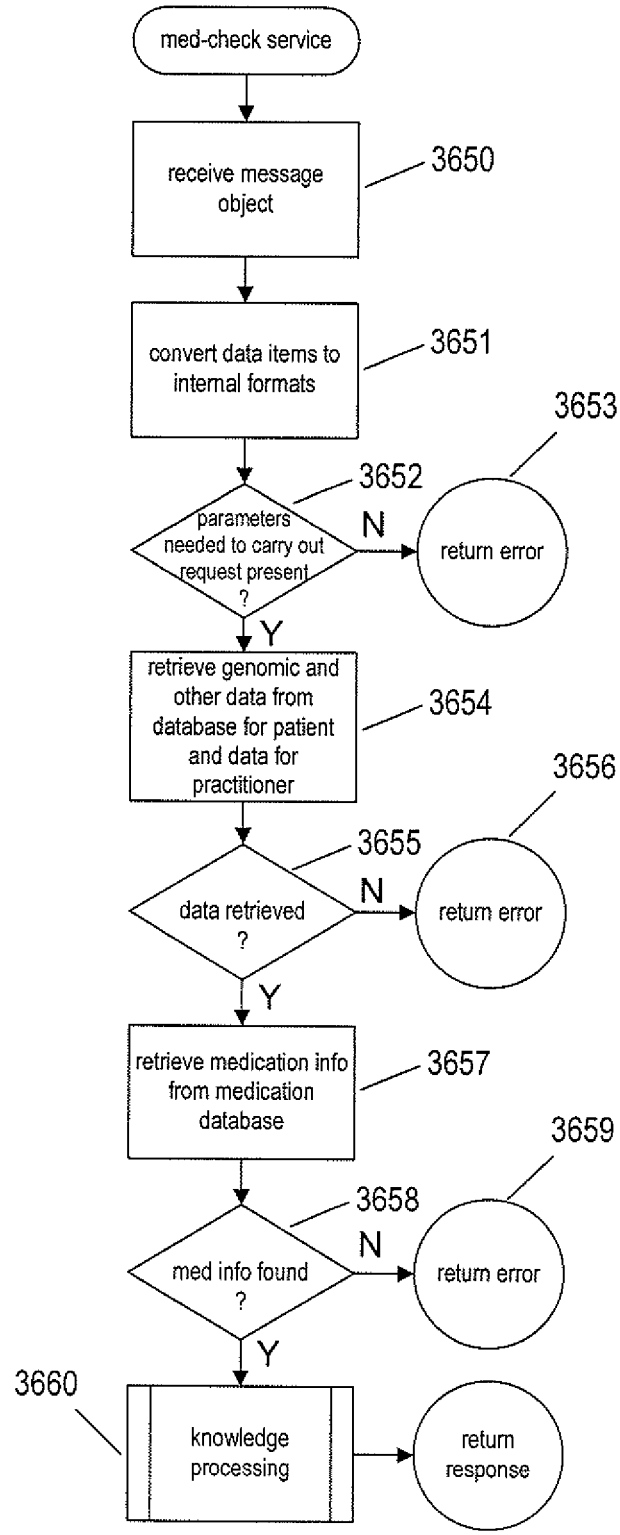
Figure 36E:
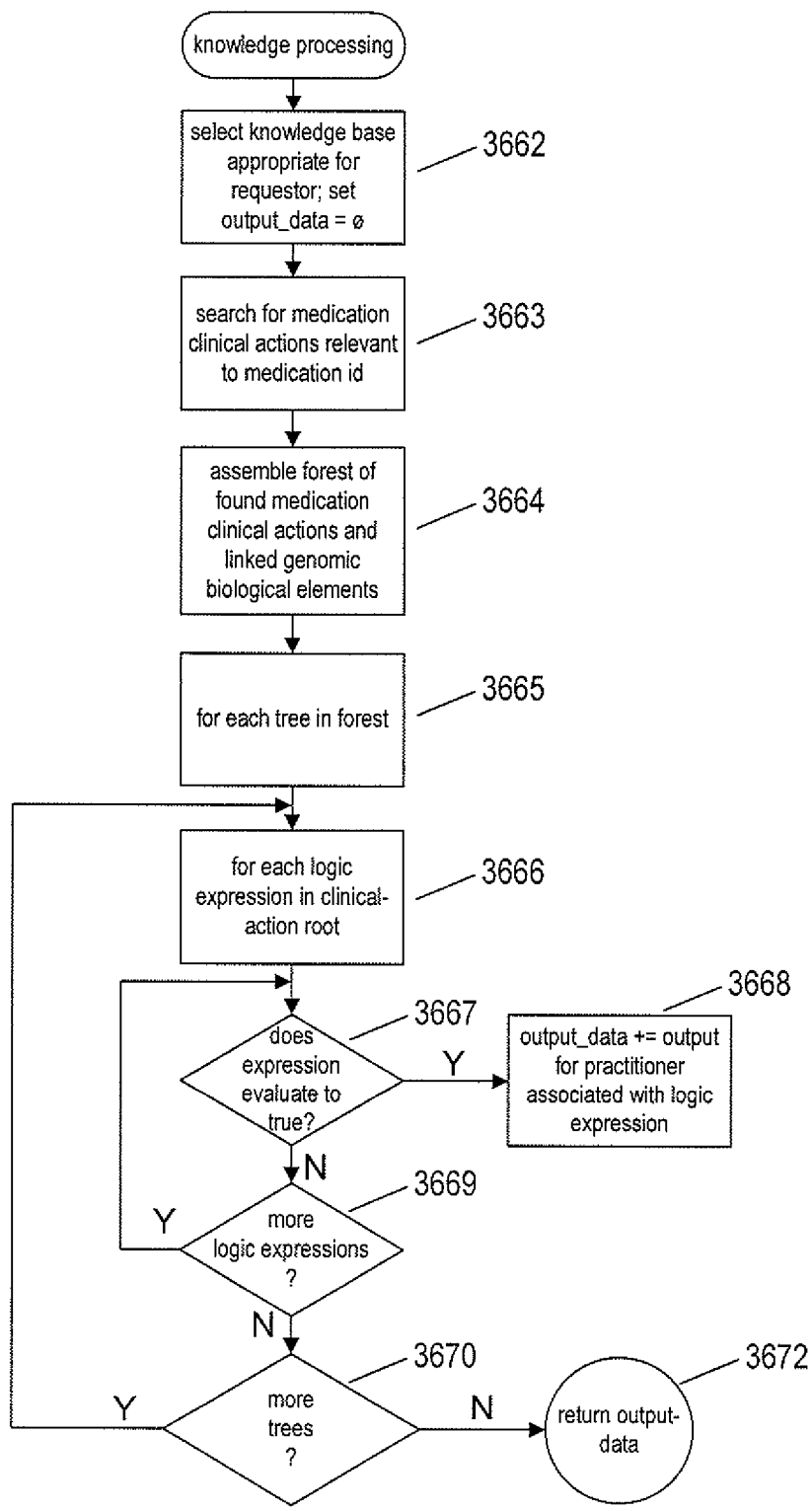

FIGS. 36D-E illustrate the handling of the authenticated and authorized message by the medicine-check service to which the message body returned by the authorization service is forwarded by the request-handling service, in step 3605 of FIG. 36A. In step 3650, the medicine-check service receives the message object. In step 3651, the medicine-check service converts data items in the message object to internal, standard or normalized formats. In step 3652, the medicine-check service determines whether or not there are sufficient parameters included in the message object to carry out the request. When there are not sufficient parameters included in the message object, an error is returned in step 3653. Otherwise, in step 3654, the medicine-check service retrieves genomic and other data for the patient from a data-storage facility as well as data for the practitioner. When the data is not successfully retrieved, as determined in step 3655, then an error is returned in step 3656. Otherwise, the medicine-check service retrieves medication information from a medication database for the medicine identified in the request in step 3657. When the information is not found, as determined in step 3658, then an error is returned in step 3659. Otherwise, the medicine-check service carries out knowledge processing, in step 3660, as previously described with reference to FIG. 19 and other figures. FIG. 36E illustrates the knowledge processing carried out in step 3660 in FIG. 36D. In step 3662, the appropriate knowledge base for the requester is selected, as discussed above with reference to FIG. 16B, and a local variable output_data is set to null, or empty. In step 3663, the clinical-knowledge data structure is searched, using indices, to find clinical-action nodes relevant to the identifier for the medication. In step 3664, a forest of subtrees, each rooted by a clinical-action node found in step 3663, is assembled from the clinical-knowledge data structure generally stored within a data-storage facility and the portions of which may be locally cached. Finally, in nested for-loops 3665-3670, the logic expressions in the clinical-action-node roots of each tree in the forest are evaluated and, for each clinical-action-root node, when a logic expression evaluates to TRUE, output from the clinical-action node is added to local variable output_data. The contents of local variable output_data are returned, in step 3672.

The above-described example is but one example of many different possible types of requests and request processing carried out by the cloud-like medical-information service. Generic requests can be made by patients, for example, to view their data, including output data related to any gene variants detected in the patient's genome. Similarly, medical practitioners can review biological characterizations, including genomic variants, of patients. Medical researchers and clinicians can access the clinical-knowledge data structure to retrieve enormous quantities of information, including information about populations of patients, with patient identities removed, in order to carry out various types of medical research. Practitioners can obtain information related to symptoms and diagnoses, pathophysiology, risks of individual patients for various types of pathologies and symptoms, treatment choices and effectiveness, risks for transmission of genetic variants and related problems to offspring, medical conditions, carrier status, and many other types of information requests.

Although the current invention has been described in terms of particular embodiments, it is not intended that the invention be limited to these embodiments. Modifications within the spirit of the invention will be apparent to those skilled in the art. For example, any of many different design and implementation parameters, including hardware platform, operating system, virtualization methods, cloud-computing-facility selection, modular organization, control structures, data structures, programming languages, communications protocols, security techniques and procedures, and other such parameters may be varied to produce many different alternative implementations of the cloud-like medical-information service. The cloud-like medical-information service has been deliberately designed to be extensible in many dimensions. The system is designed to accommodate new types of clinical-action nodes and corresponding medical information, new types of biological-element nodes corresponding to new types of characterizations of patients' biology, chemistry, and biome, and new types of variant nodes that describe variations in a wide variety of different types of patient-biology characterizations. The cloud-like medical-information service can accommodate many different types of annotations and expert-supplied information, as well as references to the scientific literature, in order to continuously update the medical information stored in the clinical-knowledge data structure. The cloud-like medical-information service can be easily enhanced to allow for receiving requests and transmitting responses to any of many different types of user devices via many different types of communications media. While information returned to users by the cloud-like medical-information service may be computed information, the cloud-like medical-information service may also return stored information or aggregated stored information that is not produced by real-time computation.

It is appreciated that the previous description of the disclosed embodiments is provided to enable any person skilled in the art to make or use the current disclosure. Various modifications to these embodiments will be readily apparent to those skilled in the art, and the generic principles defined herein may be applied to other embodiments without departing from the spirit or scope of the disclosure. Thus, the current disclosure is not intended to be limited to the embodiments shown herein but is to be accorded the widest scope consistent with the principles and novel features disclosed herein.

The invention claimed is:

1. A cloud-like medical-information system comprising:
physical servers and data-storage facilities within a cloud-computing facility;
virtual servers and data-storage facilities implemented within the physical servers and data-storage facilities; and
computer instructions executed by the virtual servers that control the cloud-like medical-information system to
receive a request message from a user device through a secure communications medium, the request message containing a query,
authenticate and authorize the request,
access a network-like clinical-knowledge data structure stored in the virtual data-storage facilities, the clinical-knowledge data structure including clinical-action nodes, biological-element nodes, and variant nodes linked together in a network-like data structure,
select candidate tree-like substructures from the network-like data structure, each candidate tree-like substructure having a clinical-action-node root node,
evaluate the candidate tree-like substructures for relevance to the query,
prepare a response message from information extracted from one or more relevant tree-like substructures, and
return the response message to the user device through the secure communications medium in less than a maximum response time.

2. The cloud-like medical-information system of claim 1 wherein the request message includes a first hash-based message authentication code computed from a portion of the query using a secret key; and
wherein the cloud-like medical-information system, as part of an authentication process, similarly computes a second hash-based message authentication code computed from the portion of the query using the secret key and rejects the request message when the first and second hash-based message authentication codes are not identical.

3. The cloud-like medical-information system of claim 1 wherein the cloud-like medical-information system determines, by accessing encrypted authorization data stored in one or more data-storage facilities within the cloud-computing facility, whether a user identified by a user identifier in the query is authorized to submit the query to the cloud-like medical-information system and rejects the request message when the identified user is not authorized to submit the query.

4. The cloud-like medical-information system of claim 1
wherein the network-like clinical-knowledge data structure is stored in one or more data-storage facilities within the cloud-computing facility; and
wherein the selected candidate tree-like substructures are instantiated as objects in one or more server memories.

5. The cloud-like medical-information system of claim 1 wherein each clinical-action node in the network-like data structure includes:
references to one or more biological-element nodes in the network-like data structure;
one or more expressions or data substructures that include one or more of
references to biological-element nodes, and
routines that access biological-element nodes referenced by the clinical-action node;
and medical information related to those patients for which evaluation of at least one of the one or more expressions or data substructures with respect to patient data stored in one or more data-storage facilities within the cloud-computing facility indicates that the patient described by the patient data has a biology characterized by the expression or data substructure.

6. The cloud-like medical-information system of claim 5 wherein each biological-element node in the network-like data structure includes:
references to one or more clinical-action nodes;
references to one or more variant nodes; and
one or more expressions or data substructures that include one or more references to variant nodes.

7. The cloud-like medical-information system of claim 6 wherein each variant node in the network-like data structure includes:
references to one or more biological-element nodes; and
information that described a variation in a biopolymer, biome organism, or other biological component.

8. The cloud-like medical-information system of claim 1 wherein the cloud-like medical-information system selects candidate tree-like substructures from the network-like data structure by selecting those substructures from the network-like data structure for which at least one leaf node represents one or more biological variants identified in a patient and stored in data for the patient in one or more data-storage facilities within the cloud-computing facility.

9. The cloud-like medical-information system of claim 1 wherein the cloud-like medical-information system evaluates a candidate tree-like substructure for relevance to the query by:
sequentially evaluating each expression or data substructure stored in the clinical-action-node root node of the candidate tree-like substructure, substituting, for each reference in the expression or data substructure to a biological-element node, an evaluation result for the biological-element node, the evaluation result for the biological element obtained by evaluating variant nodes referenced by the biological-element node for occurrence within in a patient identified in the query using patient data that identifies variants in the patient stored in one or more data-storage facilities within the cloud-computing facility; and
when an expression or data substructure evaluates to an indication that indicates that the patient described by the patient data has a biology characterized by the expression or data substructure, determining the candidate tree-like substructure to be relevant.

10. The cloud-like medical-information system of claim 1 wherein the maximum response time is one of:
1 second;
0.5 seconds;
0.1 seconds; and
less than 0.1 seconds.

11. A cloud-like medical-information system comprising:
physical servers and data-storage facilities within a cloud-computing facility;
virtual servers and data-storage facilities implemented within the physical servers and data-storage facilities;
human-genome-related medical information and other medical information stored in one or more of the one or more data-storage facilities within a cloud-computing facility;
genomic-variant-data for one or more patients stored in one or more of the one or more data-storage facilities within a cloud-computing facility;

computer instructions executed by the virtual servers that control the cloud-like medical-information system to
receive a request message from an electronic-health-record application through a secure communications medium, the request message containing a query for medical information related to an identified patient relevant to genomic variants identified in the patient and described by the genomic-variant-data for the patient, the request message generated and transmitted by a routine call inserted into the electronic-health-record application,
authenticate and authorize the request,
prepare a response message from information extracted from the human-genome-related medical information and other medical information, and
return the response message to the electronic-health-record application through the secure communications medium.

12. The cloud-like medical-information system of claim 11 wherein the human-genome-related medical information is stored in a network-like clinical-knowledge data structure that is stored in the one or more of the one or more data-storage facilities within a cloud-computing facility, the clinical-knowledge data structure including clinical-action nodes, biological-element nodes, and variant nodes linked together in the network-like data structure.

13. The cloud-like medical-information system of claim 12 wherein each clinical-action node in the network-like data structure includes:
references to one or more biological-element nodes in the network-like data structure;
one or more expressions or data substructures that include one or more of
references to biological-element nodes, and
routines that access biological-element nodes referenced by the clinical-action node;
and medical information related to those patients for which evaluation of at least one of the one or more expressions or data substructures with respect to the genomic-variant-data indicates that the patients have a biology characterized by the expression or data substructure.

14. The cloud-like medical-information system of claim 13 wherein each biological-element node in the network-like data structure includes:
references to one or more clinical-action nodes;
references to one or more variant nodes; and
one or more expressions or data substructures that include one or more references to variant nodes.

15. The cloud-like medical-information system of claim 14 wherein each variant node in the network-like data structure includes:
references to one or more biological-element nodes; and
information that described a genomic variant.

16. A cloud-like medical-information system comprising:
physical servers and data-storage facilities within a cloud-computing facility;
virtual servers and data-storage facilities implemented within the physical servers and data-storage facilities;
human-genome-related medical information and other medical information stored in one or more of the one or more data-storage facilities within a cloud-computing facility;
genomic-variant-data for one or more patients stored in one or more of the one or more data-storage facilities within a cloud-computing facility;
computer instructions executed by the virtual servers that control the cloud-like medical-information system to
receive a request message from a user device through a secure communications medium, the request message containing a query for medical information related to an identified patient relevant to genomic variants identified in the patient and described by the genomic-variant-data for the patient, the request message generated,
authenticate and authorize the request,
prepare a response message from information extracted from the human-genome-related medical information and other medical information, and
return the response message to the user device through the secure communications medium in less than a maximum response time.

17. The cloud-like medical-information system of claim 16 wherein the human-genome-related medical information is stored in a network-like clinical-knowledge data structure that is stored in the one or more of the one or more data-storage facilities within a cloud-computing facility, the clinical-knowledge data structure including clinical-action nodes, biological-element nodes, and variant nodes linked together in the network-like data structure.

18. The cloud-like medical-information system of claim 17 wherein each clinical-action node in the network-like data structure includes:
references to one or more biological-element nodes in the network-like data structure;
one or more expressions or data substructures that include one or more of
references to biological-element nodes, and
routines that access biological-element nodes referenced by the clinical-action node;
and medical information related to those patients for which evaluation of at least one of the one or more expressions or data substructures with respect to the genomic-variant-data indicates that the patients have a biology characterized by the expression or data substructure.

19. The cloud-like medical-information system of claim 18 wherein each biological-element node in the network-like data structure includes:
references to one or more clinical-action nodes;
references to one or more variant nodes; and
one or more expressions or data substructures that include one or more references to variant nodes.

20. The cloud-like medical-information system of claim 14 wherein each variant node in the network-like data structure includes:
references to one or more biological-element nodes; and
information that described a genomic variant.

21. The cloud-like medical-information system of claim 16 wherein the maximum response time is one of:
1 second;
0.5 seconds;
0.1 seconds; and
less than 0.1 seconds.

* * * * *